(12) United States Patent
Sun et al.

(10) Patent No.: US 10,995,061 B2
(45) Date of Patent: May 4, 2021

(54) SPAK KINASE INHIBITORS AS NEUROPROTECTIVE AGENTS

(71) Applicants: United States Government as represented by the Department of Veterans Affairs, Washington, DC (US); The University of Pittsburgh—of the Commonwealth of Higher Education, Pittsburgh, PA (US); Xiamen University, Fujian (CN); University of Exeter, Exeter (GB)

(72) Inventors: Dandan Sun, Pittsburgh, PA (US); Xianming Deng, Fujian (CN); Jinwei Zhang, Exeter (GB); Mohammad Iqbal Hossain Bhuiyan, Pittsburgh, PA (US); Bradley J. Molyneaux, Pittsburgh, PA (US)

(73) Assignees: United States Government as Represented by the Department of Veterans Affairs, Washington, DC (US); The University of Pittsburgh—of the Commonwealth of Higher Education, Pittsburgh, PA (US); Xiamen University, Xiamen (CN); University of Exeter, Exeter (GB)

( * ) Notice: Subject to any disclaimer, the term of this patent is extended or adjusted under 35 U.S.C. 154(b) by 0 days.

(21) Appl. No.: 16/588,751

(22) Filed: Sep. 30, 2019

(65) Prior Publication Data

US 2020/0102266 A1    Apr. 2, 2020

Related U.S. Application Data

(60) Provisional application No. 62/740,336, filed on Oct. 2, 2018.

(51) Int. Cl.
C07C 255/44 (2006.01)
A61P 25/28 (2006.01)
(52) U.S. Cl.
CPC ............ *C07C 255/44* (2013.01); *A61P 25/28* (2018.01)
(58) Field of Classification Search
CPC ................................................ C07C 255/44
See application file for complete search history.

(56) References Cited

U.S. PATENT DOCUMENTS

2017/0326160 A1    11/2017    Delavenne et al.

FOREIGN PATENT DOCUMENTS

WO    WO-2020/072386 A1    4/2020

OTHER PUBLICATIONS

Janssen, et al. Document No. 86:55186, retrieved from STN; entered in STN on May 12, 1984.*
Ellsworth, et al. Document No. 131:295129, retrieved from STN; 1999.*
Jakobsen, et al. Document No. 150:555798, retrieved from STN; entered in STN on May 22, 2009.*
Gojon-Zorrilla, et al. Document No. 164:159252, retrieved from STN; entered in STN on Jan. 8, 2016.*
No new references.*
U.S. Appl. No. 62/740,336, filed Oct. 2, 2018, Dandan Sun.
PCT, PCT/US2019/053887 (WO/2020/072386), Sep. 30, 2019 (Apr. 9, 2020), The United States Government as represented by the Department of Veterans Affairs.
Kikuchi et al. "Discovery of Novel SPAK Inhibitors That Block WNK Kinase Signaling to Cation Chloride Transporters" Basic Research. Jun. 30, 2015 (Jun. 30, 2015), vol. 26, p. 1525-1536.
Pubchem CID 97289639 Create Date: Dec. 11, 2015 (Dec. 11, 2015) Date Accessed: Jan. 2020 (Jan. 20, 2020); p. 2.
Zhang et al. "Modulation of brain cation-Cl-cotransport via the SPAK kinase inhibitor ZT-la", Nature Communications. Jan. 7, 2020 (Jan. 7, 2020) vol. 11, p. 1-17.
International Search Report and Written Opinion dated Feb. 10, 2020 by the International Searching Authority for International Application No. PCT/US2019/053887, filed on Sep. 30, 2019 and published as WO 2020/072386 dated Apr. 9, 2020 (Applicant—The United States Government As Represented by the Department of Veterans Affairs) (8 Pages).

\* cited by examiner

*Primary Examiner* — Shawquia Jackson
(74) *Attorney, Agent, or Firm* — Ballard Spahr LLP

(57) ABSTRACT

The present disclosure is concerned with N-(5-chloro-4-((4-chlorophenyl)(cyano)methyl)-2-methylphenyl)benzamide compounds that are capable of inhibiting SPAK kinase function, methods of treating hypoxic brain injuries due to, for example, ischemic stroke. This abstract is intended as a scanning tool for purposes of searching in the particular art and is not intended to be limiting of the present invention.

18 Claims, 38 Drawing Sheets
Specification includes a Sequence Listing.

SEQUENCE LISTING

<160> NUMBER OF SEQ ID NOS: 4

<210> SEQ ID NO 1
<211> LENGTH: 24
<212> TYPE: PRT
<213> ORGANISM: Artificial Construct
<220> FEATURE:
<223> OTHER INFORMATION: Synthetic Construct

<400> SEQUENCE: 1

```
Arg Arg His Tyr Tyr Tyr Asp Thr His Thr Asn Thr Tyr Tyr Leu Arg
1               5                   10                  15

Thr Phe Gly His Asn Thr Arg Arg
            20
```

<210> SEQ ID NO 2
<211> LENGTH: 18
<212> TYPE: PRT
<213> ORGANISM: Artificial Construct
<220> FEATURE:
<223> OTHER INFORMATION: Synthetic Construct

<400> SEQUENCE: 2

```
Ser Glu Glu Gly Lys Pro Gln Leu Val Gly Arg Phe Gln Val Thr Ser
1               5                   10                  15

Ser Lys
```

<210> SEQ ID NO 3
<211> LENGTH: 18
<212> TYPE: PRT
<213> ORGANISM: Artificial Construct
<220> FEATURE:
<223> OTHER INFORMATION: Synthetic Construct

<400> SEQUENCE: 3

```
Ser Glu Glu Gly Lys Pro Gln Leu Val Gly Ala Phe Gln Val Thr Ser
1               5                   10                  15

Ser Lys
```

<210> SEQ ID NO 4
<211> LENGTH: 10
<212> TYPE: PRT
<213> ORGANISM: Artificial Construct
<220> FEATURE:
<223> OTHER INFORMATION: Synthetic Construct

<400> SEQUENCE: 4

```
Cys Cys Pro Gly Cys Cys Gly Gly Gly Gly
1               5                   10
```

SPAK KINASE INHIBITORS AS NEUROPROTECTIVE AGENTS

CROSS-REFERENCE TO RELATED APPLICATIONS

This application claims the benefit of U.S. Application No. 62/740,336, filed on Oct. 2, 2018, which is incorporated herein by reference in its entirety.

STATEMENT REGARDING FEDERALLY SPONSORED RESEARCH

This invention was made with government support under grant number VA I01BX002891 awarded by the U.S. Department of Veterans Affairs and grant number R01 NS038118 awarded by the National Institutes of Health. The government has certain rights in the invention.

REFERENCE TO SEQUENCE LISTING

The Sequence Listing submitted Oct. 2, 2019 as a text file named "37759_0067U2_ST25.txt," created on Sep. 16, 2019, and having a size of 1,421 bytes is hereby incorporated by reference pursuant to 37 C.F.R. § 1.52(e)(5).

BACKGROUND

Regulation of cellular ion transport is critical for brain water homeostasis. Vectorial ion transport across the apical and basolateral membranes of choroid plexus epithelium (CPe), accompanied by osmotic transport of water, results in daily cerebrospinal fluid (CSF) secretion of >500 cc/day into brain ventricular spaces (Steffensen et al. (2018) Nat Commun 9, 2167). Impaired ionic homeostasis in the CPe can result in hydrocephalus (accumulation of excess CSF in the brain ventricles), as seen in the context of intraventricular hemorrhage (IVH) (Cherian et al. (2004) Brain Pathol 14, 305-311; Strahle et al. (2012) Transl Stroke Res 3, 25-38). Coordinated transmembrane influx and efflux of ions and water is also necessary for cell volume maintenance in neurons and glia. Impaired cell volume homeostasis can result in cytotoxic cell swelling and cerebral edema, as occurs after ischemic stroke (Kahle et al. (2009b) Physiology 24, 257-265; Simard et al. (2007) Lancet Neurol 6, 258-268). Ischemic cerebral edema and hydrocephalus are neurosurgical diseases, which can treated by decompressive hemicraniectomy or permanent, catheter-based CSF shunting, respectively (Stochetti and Maas (2014) The New England journal of medicine 371, 972). However, these morbid operative procedures have been used for decades with minimal further innovation or reduction in failure rates (Wang et al. (1990) Chemotherapy 36, 177-184; Warf et al. (2011) J Neurosurg Pediatr 8, 502-508; Wu et al. (2007) Neurosurgery 61, 557-562; discussion 562-553). Thus, novel pharmacological modulators of brain salt and water homeostasis are urgently needed to provide a non-surgical alternative to current treatments of these neurological disorders.

The electroneutral cation-$Cl^-$ cotransporters (CCCs) are secondary-active plasmalemmal ion transporters that utilize electrochemically favorable trans-membrane gradients of $Na^+$ and/or $K^+$, established by primary active transport via the ouabain-sensitive $Na^+,K^+$-ATPase, to drive the transport of $Cl^-$ (and $K^+$) into or out of cells. The two CCC subtypes include the $Cl^-$-importing, $Na^+$-driven CCCs (NCC, NKCC1, and NKCC2; to be referred to as "N[K]CCs"), and the $Cl^-$-exporting, $K^+$-driven CCCs (KCC1-4; the "KCCs") (Arroyo et al. (2013) Molecular aspects of medicine 34, 288-298). These evolutionarily conserved transporters are among the most important mediators of ion transport in multicellular organisms (Gama (2005) Physiological reviews 85, 423-493), with particular importance in mammalian CNS regulation of ionic and water homeostasis (Gagnon and Delpire (2013) Nature medicine 19, 1524-1528; Kahle et al. (2008) Nat Clin Pract Neurol 4, 490-503). The coordinated regulation of CCC function is important for cell volume regulation in most brain cells, preventing excessive cell swelling or shrinkage in response to osmotic or ischemic stress (Kahle et al. (2015) Trends Mol Med 21, 513-523; Zhang et al. (2016) Scientific reports 6, 35986). The central importance of CCCs to CSF homeostasis by choroid plexus has been recently recognized (Karimy et al. (2017) Nature medicine 23, 997-1003; Steffensen et al. (2018) Nat Commun 9, 2167).

SPAK (SPS1-related proline/alanine-rich kinase) and OSR1 (oxidative stress-responsive kinase 1) are closely related Ste20-type serine-threonine protein kinases considered master regulators of the CCCs (Zhang et al. (2017) Expert Opin Ther Targets 21, 795-804). SPAK and OSR1 are activated by phosphorylation of the regulatory "T-loop" residue (SPAK Thr233 and OSR1 Thr185) by one of the four WNK ["with no lysine" (K)] protein kinases (Moriguchi et al. (2005) The Journal of biological chemistry 280, 42685-42693; Vitari et al. (2005) The Biochemical journal 391, 17-24). WNKs-SPAK/OSR1 protein kinases drive chloride influx by phosphorylation and activation of the $Na^+$-driven CCC members (NCC, NKCC1, and NKCC2) (Piechotta et al. (2002) The Journal of biological chemistry 277, 50812-50819; Richardson et al. (2008) Journal of cell science 121, 675-684; Richardson et al. (2011) Journal of cell science 124, 789-800) while inhibiting chloride efflux via phosphorylation and inactivation of KCC1-4 (de Los Heros et al. (2014) The Biochemical journal 458, 559-573; Zhang et al. (2016) Scientific reports 6, 35986). This reciprocal regulation of the $Na^+$- and $K^+$-driven CCCs by SPAK/OSR1 ensures that cellular $Cl^-$ influx and efflux is tightly coordinated (Arroyo et al. (2013) Molecular aspects of medicine 34, 288-298; Kahle et al. (2010) Biochimica et biophysica acta 1802, 1150-1158), and is essential for regulation of normal cell volume and epithelial transport in multiple tissues (Damkier et al. (2013) Physiological reviews 93, 1847-1892).

Recent work has highlighted the importance of SPAK-regulated CCC-mediated ion transport in brain pathologies associated with deranged ionic and brain water homeostasis. Experimental ischemic cerebral edema is associated with up-regulated phosphorylation of the SPAK/OSR1 T-loop and NKCC1 ($Thr^{203}/Thr^{207}/Thr^{212}$) in both neurons and oligodendrocytes (Begum et al. (2015) Stroke 46, 1956-1965). Mouse germline SPAK knockout significantly reduces ischemia-induced NKCC1 phosphorylation, infarct volume, axonal demyelination, and cerebral edema following ischemic stroke (Begum et al. (2015) Stroke 46, 1956-1965; Zhao et al. (2017) Journal of cerebral blood flow and metabolism: official journal of the International Society of Cerebral Blood Flow and Metabolism 37, 550-563). Choroid plexus NKCC1 is an essential mediator of ion transport in the CSF hypersecretory response that drives development of post-hemorrhagic hydrocephalus (Karimy et al. (2017) Nature medicine 23, 997-1003). The 3.5-fold increase in CSF secretion accompanying the hydrocephalus caused by experimental IVH is associated with similarly up-regulated phosphorylation of SPAK/OSR1-NKCC1 at the choroid plexus apical membrane (Karimy et al. (2017) Nature medicine 23, 997-1003), the site of highest SPAK abundance among all epithelial tissues (Piechotta et al. (2003) The Journal of biological chemistry 278, 52848-52856). Genetic inhibition of choroid plexus SPAK by intracerebroventricular siRNAs normalized CSF secretion rates and reversed post-IVH ventriculomegaly (Karimy et al. (2017) Nature medicine 23, 997-1003). Despite the importance of CCCs to CNS physiology, successful development of drugs directly targeting CNS CCCs either by inhibiting NKCC1 (Jantzie et al. (2015) Pediatric research 77, 554-562; Kahle and Staley (2008) Neurosurgical focus 25, E22) or activating the KCCs (Gagnon et al. (2013) Cell physiology 304, C693-714) has proven elusive (Cardarelli et al. (2017) Nature medicine 23, 1394-1396). Thus, there remains a need for compounds that are capable of modulating CCCs via inhibition of NKCC1 and/or activation of KCCs for reducing ischemic cerebral edema and/or stimulated CSF recresion.

SUMMARY

In accordance with the purpose(s) of the invention, as embodied and broadly described herein, the invention, in one aspect, relates to N-(5-chloro-4-((4-chlorophenyl)(cyano)methyl)-2-methylphenyl)benzamide compounds useful in the treatment of conditions or disorders associated with a dysregulation of SPAK kinase function including, but not limited to, hypoxic brain injuries due to, for example, traumatic brain injury, ischemic stroke, carbon monoxide poisoning, drowning, choking, suffocating, or cardiac arrest.

Disclosed are compounds having a structure represented by a formula:

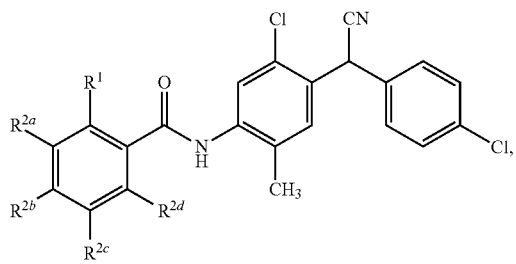

wherein $R^1$ is selected from —OH, —$SR^{20}$, and —$NR^{21a}R^{21b}$; wherein $R^{20}$, when present, is selected from hydrogen and C1-C4 alkyl; wherein each of $R^{21a}$ and $R^{21b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH then $R^{2c}$ is hydrogen, and provided that when $R^{20}$ is C1-C4 alkyl then at least two of $R^{2a}$, $R^{2b}$, $R^{2c}$, and $R^{2d}$ are not hydrogen, or a pharmaceutically acceptable salt thereof.

Also disclosed are compounds selected from:

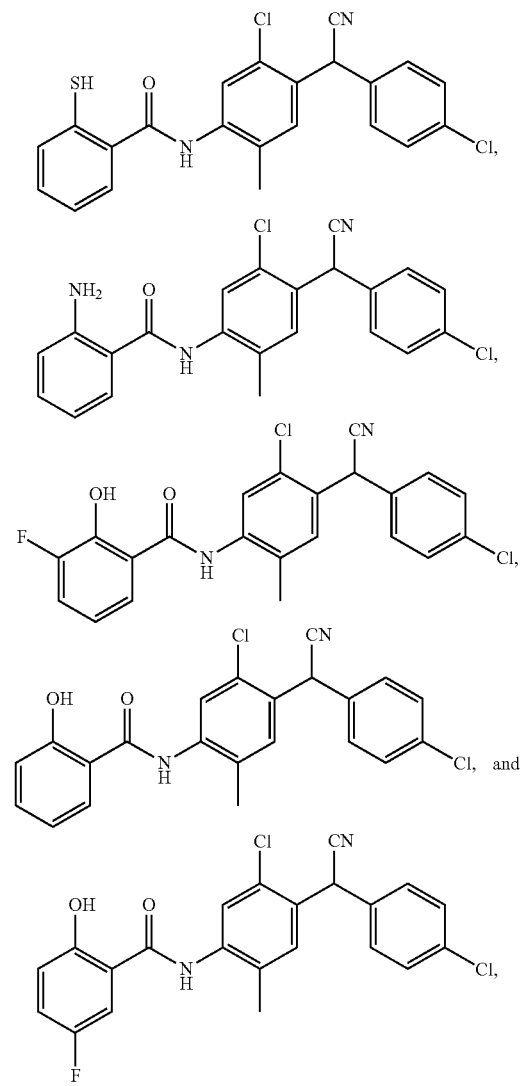

or a pharmaceutically acceptable salt thereof.

Also disclosed are pharmaceutical compositions comprising a therapeutically effective amount of at least one disclosed compound and a pharmaceutically acceptable carrier.

Also disclosed are methods for treating a hypoxic brain injury in a subject, the method comprising the step of administering to the subject an effective amount of at least one compound having a structure represented by a formula:

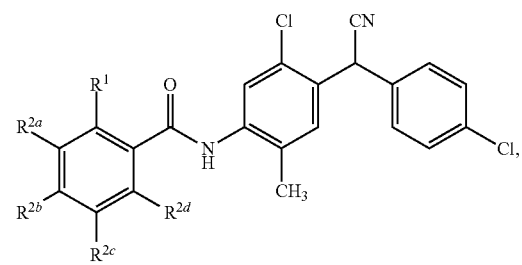

wherein $R^1$ is selected from —OH, —$SR^{20}$, and —$NR^{21a}R^{21b}$; wherein $R^{20}$, when present, is selected from hydrogen and C1-C4 alkyl; wherein each of $R^{21a}$ and $R^{21b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH and each of $R^{2b}$ and $R^{2d}$ is hydrogen then neither of $R^{2a}$ and $R^{2c}$ is halogen, or a pharmaceutically acceptable salt thereof.

Also disclosed are methods for modifying SPAK kinase function in a subject, the method comprising the step of administering to the subject an effective amount of a compound having a structure represented by a formula:

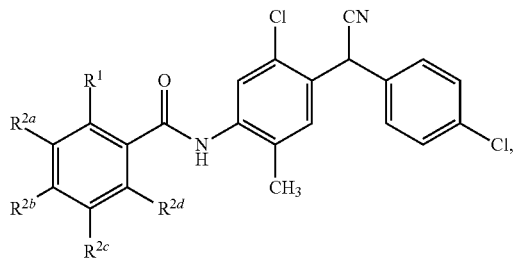

wherein $R^1$ is selected from —OH, —$SR^{20}$, and —$NR^{21a}R^{21b}$; wherein $R^{20}$, when present, is selected from hydrogen and C1-C4 alkyl; wherein each of $R^{21a}$ and $R^{21b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH and each of $R^{2b}$ and $R^{2d}$ is hydrogen then neither of $R^{2a}$ and $R^{2c}$ is halogen, or a pharmaceutically acceptable salt thereof.

Also disclosed are methods for modifying SPAK kinase function in at least one cell, the method comprising the step of administering to the subject an effective amount of a compound having a structure represented by a formula:

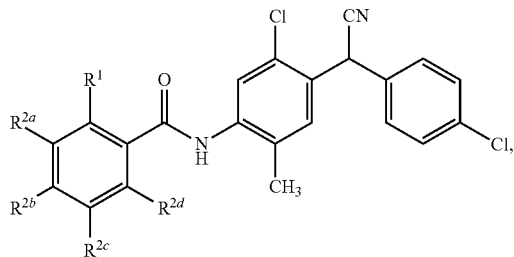

wherein $R^1$ is selected from —OH, —$SR^{20}$, and —$NR^{21a}R^{21b}$; wherein $R^{20}$, when present, is selected from hydrogen and C1-C4 alkyl; wherein each of $R^{21a}$ and $R^{21b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH and each of $R^{2b}$ and $R^{2d}$ is hydrogen then neither of $R^{2a}$ and $R^{2c}$ is halogen, or a pharmaceutically acceptable salt thereof.

Also disclosed are kits comprising a compound having a structure represented by a formula:

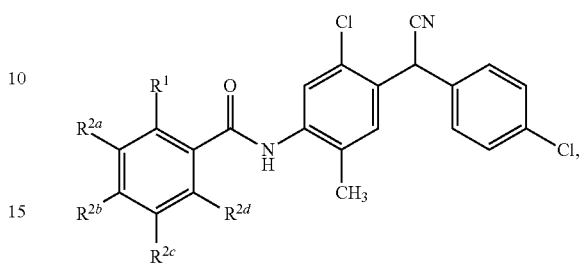

wherein $R^1$ is selected from —OH, —$SR^{20}$, and —$NR^{21a}R^{21b}$; wherein $R^{20}$, when present, is selected from hydrogen and C1-C4 alkyl; wherein each of $R^{21a}$ and $R^{21b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH and each of $R^{2b}$ and $R^{2d}$ is hydrogen then neither of $R^{2a}$ and $R^{2c}$ is halogen, or a pharmaceutically acceptable salt thereof, and one or more of: (a) at least one agent associated with the treatment of a hypoxic brain injury; (b) instructions for administering the compound in connection with treating a hypoxic brain injury; and (c) instructions for treating a hypoxic brain injury.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BRIEF DESCRIPTION OF THE DRAWINGS

The accompanying figures, which are incorporated in and constitute a part of this specification, illustrate several aspects and together with the description serve to explain the principles of the invention.

FIG. 8 shows representative data illustrating $^{86}Rb^+$ uptake assays in the presence of ZT-1a.

Figure 1A:
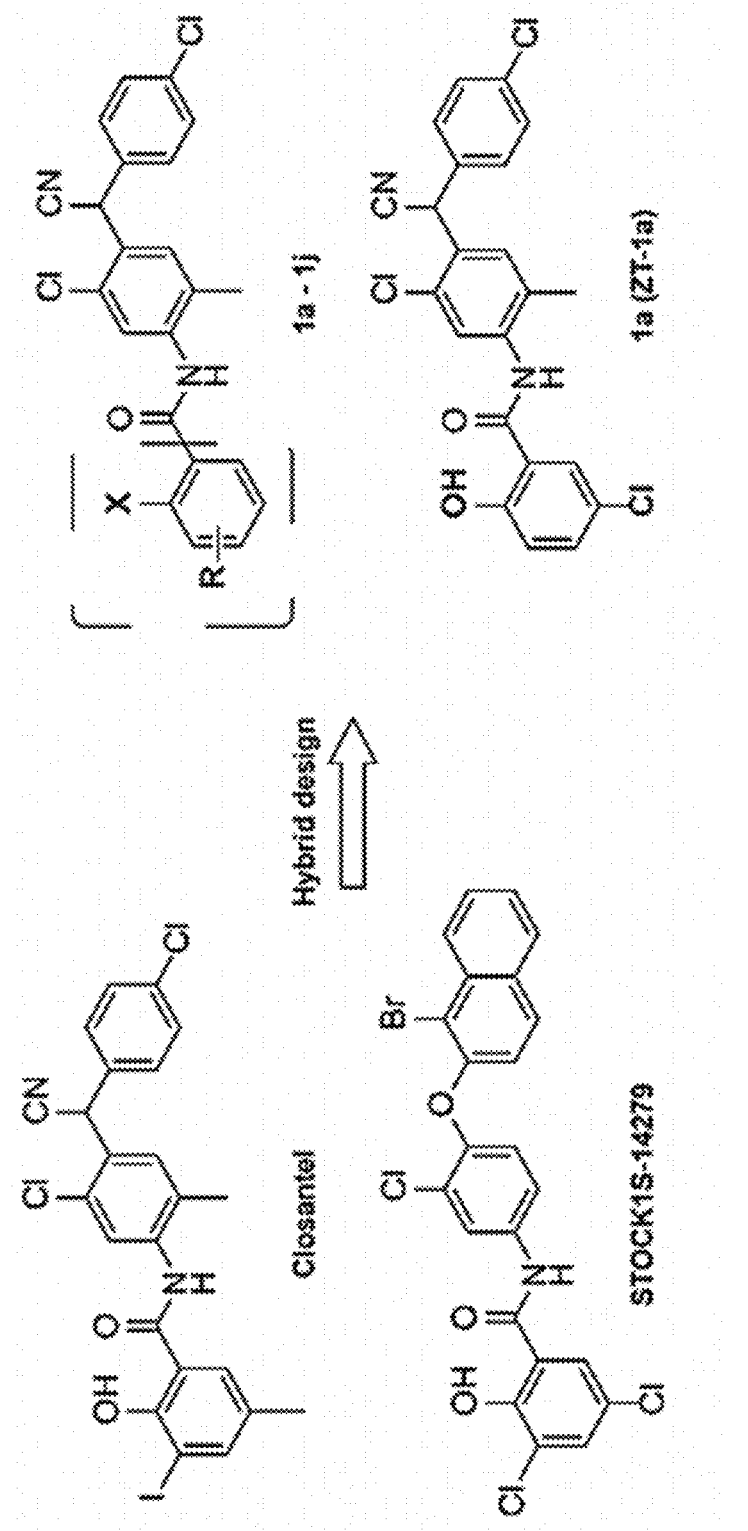
FIG. 1A shows a representative hybrid design strategy for WNK pathway inhibitors.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a hypoxic brain injury. The term "patient" includes human and veterinary subjects. In some aspects of the disclosed methods, the subject has been diagnosed with a need for treatment of a hypoxic brain injury prior to the administering step. In various aspects, the hypoxic brain injury is due to traumatic brain injury, ischemic stroke, carbon monoxide poisoning, drowning, choking, suffocating, or cardiac arrest.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the condition from occurring in a subject that can be predisposed to the condition but has not yet been diagnosed as having it; (ii) inhibiting the condition, i.e., arresting its development; or (iii) relieving the condition, i.e., causing regression of the condition. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a hypoxic brain injury prior to the administering step. As used herein, the phrase "identified to be in need of treatment for a disorder," or the like, refers to selection of a subject based upon need for treatment of the disorder or condition. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

The term "comprising" (and its grammatical variations) as used herein is used in the inclusive sense of "having" or "including" and not in the exclusive sense of "consisting of."

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and include the physiologically acceptable salts, which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric acid, and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzene-sulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula A$^1$C(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene) $O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R*_2))_{2-3}O-$, or $-S(C(R*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited to alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

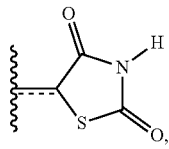

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules, which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids, which are present in different states of order, which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

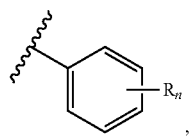

which is understood to be equivalent to a formula:

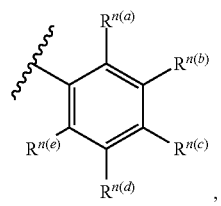

wherein n is typically an integer. That is, $R^n$ is understood to represent five independent substituents, $R^{n(a)}$, $R^{n(b)}$, $R^{n(c)}$, $R^{n(d)}$, $R^{n(e)}$. In each such case, each of the five $R^n$ can be hydrogen or a recited substituent. By "independent substituents," it is meant that each R substituent can be independently defined. For example, if in one instance $R^{n(a)}$ is halogen, then $R^{n(b)}$ is not necessarily halogen in that instance.

In some yet further aspects, a structure of a compound can be represented by a formula:

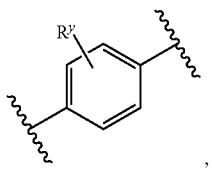

wherein $R^y$ represents, for example, 0-2 independent substituents selected from $A^1$, $A^2$, and $A^3$, which is understood to be equivalent to the groups of formulae:

wherein $R^y$ represents 0 independent substituents

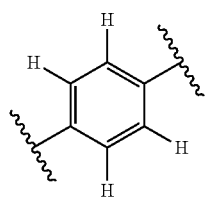

wherein $R^y$ represents 1 independent substituent

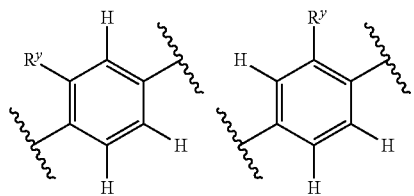

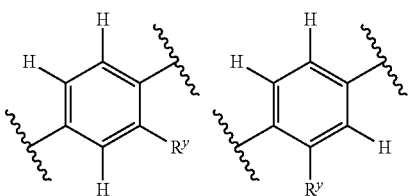

wherein $R^y$ represents 2 independent substituents

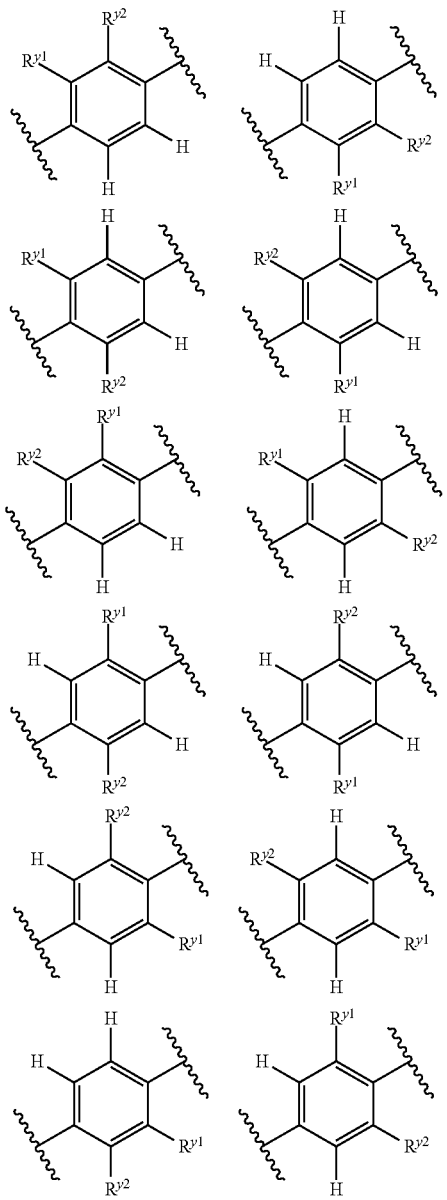

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

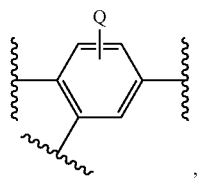

wherein, for example, Q comprises three substituents independently selected from hydrogen and A, which is understood to be equivalent to a formula:

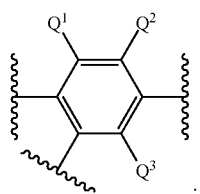

Again, by "independent substituents," it is meant that each Q substituent is independently defined as hydrogen or A, which is understood to be equivalent to the groups of formulae:
wherein Q comprises three substituents independently selected from H and A

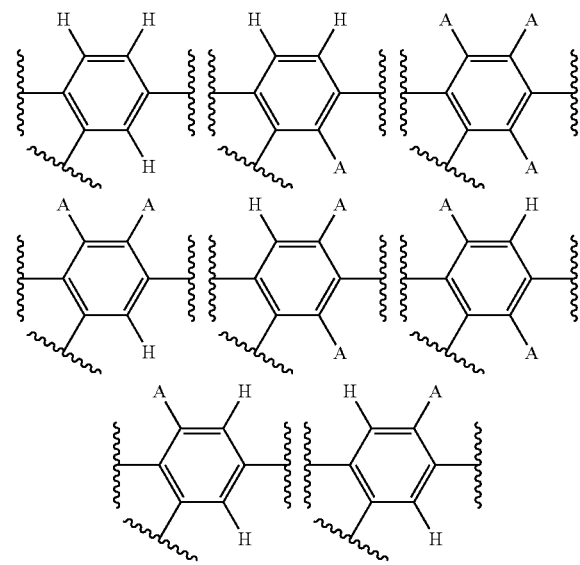

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, disclosed are N-(5-chloro-4-((4-chlorophenyl)(cyano)methyl)-2-methylphenyl)benzamide compounds useful in treating conditions or disorders associated with a dysregulation of SPAK kinase function including, but not limited to, hypoxic brain injuries due to, for example, traumatic brain injury, ischemic stroke, carbon monoxide poisoning, drowning, choking, suffocating, or cardiac arrest.

In one aspect, the disclosed compounds exhibit modification of SPAK kinase function. In a further aspect, the disclosed compounds exhibit inhibition of SPAK kinase function.

In one aspect, the disclosed compounds are useful in inhibiting SPAK kinase function in a mammal. In a further aspect, the disclosed compounds are useful in inhibiting SPAK kinase function in at least one cell.

In one aspect, the disclosed compounds are useful in the treatment of hypoxic brain injuries, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

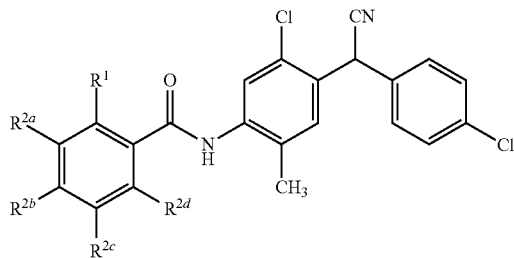

wherein $R^1$ is selected from —OH, —$SR^{20}$, and —$NR^{21a}R^{21b}$; wherein $R^{20}$, when present, is selected from hydrogen and C1-C4 alkyl; wherein each of $R^{21a}$ and $R^{21b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH then $R^{2c}$ is hydrogen, and provided that when $R^{20}$ is C1-C4 alkyl then at least two of $R^{2a}$, $R^{2b}$, $R^{2c}$, and $R^{2d}$ are not hydrogen, or a pharmaceutically acceptable salt thereof.

In one aspect, disclosed are compounds selected from:

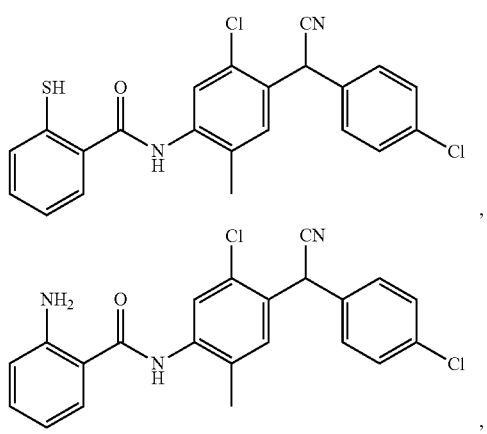

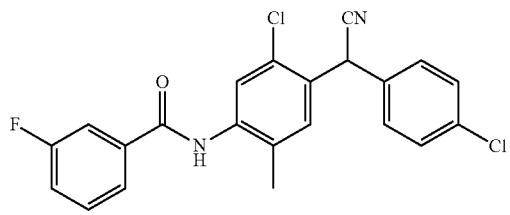

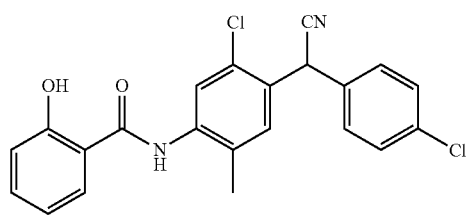

, and

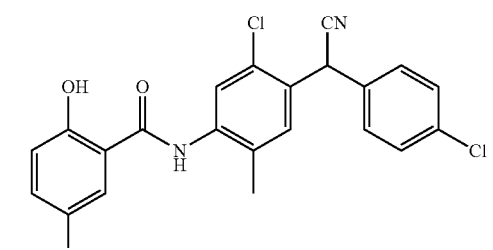

, or a pharmaceutically acceptable salt thereof.

In a further aspect, the compound has a structure represented by a formula:

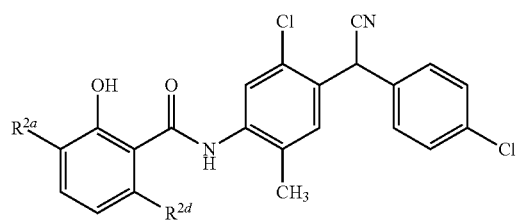

In a further aspect, the compound has a structure represented by a formula:

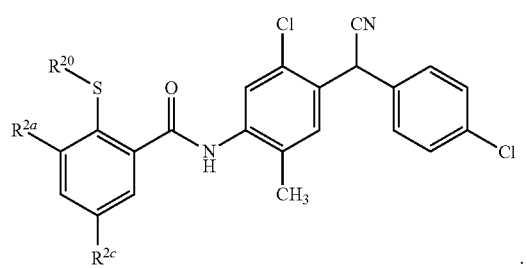

In a further aspect, the compound has a structure represented by a formula:

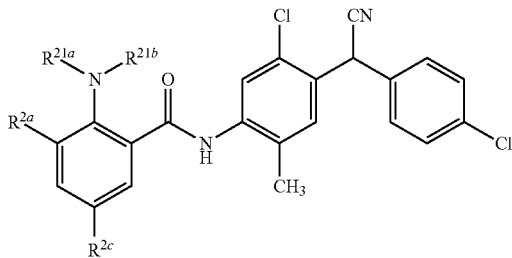

In a further aspect, the compound is selected from:

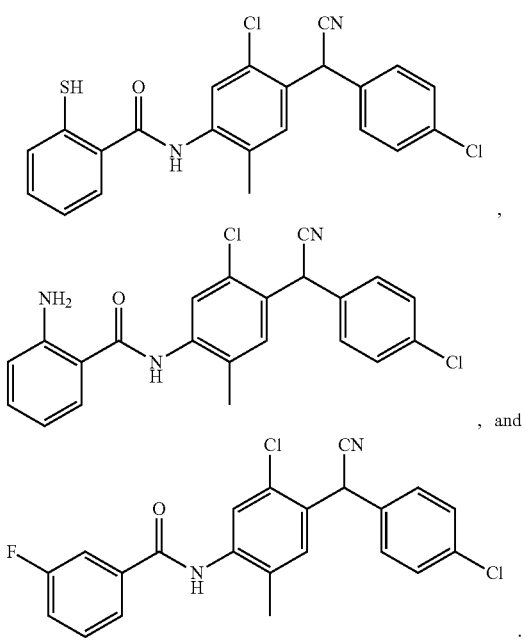

, and a. $R^1$ Groups

In one aspect, $R^1$ is selected from —OH, —SR$^{20}$, and —NR$^{21a}$R$^{21b}$, provided that when $R^1$ is —OH then $R^{2c}$ is hydrogen. In one aspect, $R^1$ is selected from —OH, —SR$^{20}$, and —NR$^{21a}$R$^{21b}$, provided that when $R^1$ is —OH and each of $R^{2b}$ and $R^{2d}$ is hydrogen then neither of $R^{2a}$ and $R^{2c}$ is halogen.

In a further aspect, $R^1$ is selected from —OH and —SR$^{20}$. In a still further aspect, $R^1$ is selected from —OH and —NR$^{21a}$R$^{21b}$. In yet a further aspect, $R^1$ is selected from —SR$^{20}$ and —NR$^{21a}$R$^{21b}$.

In a further aspect, $R^1$ is —OH.

In a further aspect, $R^1$ is —SR$^{20}$. In a still further aspect, $R^1$ is —SH.

In a further aspect, $R^1$ is —NR$^{21a}$R$^{21b}$.

b. $R^{2A}$, $R^{2B}$, $R^{2C}$, and $R^{2D}$ Groups

In one aspect, each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino. In a further aspect, each of $R^{2a}$, $R^{2b}$, $R^{2c}$, and $R^{2d}$ is hydrogen.

In a further aspect, each of $R^{2b}$ and $R^{2d}$ is hydrogen. In a still further aspect, each of $R^{2a}$ and $R^{2c}$ is not hydrogen. In yet a further aspect, at least one of $R^{2a}$ and $R^{2c}$ is not hydrogen.

In a further aspect, each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, and C1-C4 haloalkyl. In a still further aspect, each of $R^{2a}$, $R^{2b}$, $R^{2c}$, and $R^{2d}$ is independently selected from hydrogen, —F, —Cl, —NO$_2$, —CN, —OH, —SH, —NH$_2$, methyl, ethyl, n-propyl, i-propyl, —CH$_2$Cl, —CH$_2$CH$_2$Cl, —CH$_2$CH$_2$CH$_2$Cl, —CH(CH$_2$Cl)(CH$_3$), —CH$_2$F, —CH$_2$CH$_2$F, —CH$_2$CH$_2$CH$_2$F, and —CH(CH$_2$F)(CH$_3$). In yet a further aspect, each of $R^{2a}$, $R^{2b}$, $R^{2c}$, and $R^{2d}$ is independently selected from hydrogen, —F, —Cl, —NO$_2$, —CN, —OH, —SH, —NH$_2$, methyl, ethyl, —CH$_2$Cl, —CH$_2$CH$_2$Cl, —CH$_2$F, and —CH$_2$CH$_2$F. In an even further aspect, each of $R^{2a}$, $R^{2b}$, $R^{2c}$, and $R^{2d}$ is independently selected from hydrogen, —F, —Cl, —NO$_2$, —CN, —OH, —SH, —NH$_2$, —CH$_2$Cl, and —CH$_2$F.

In a further aspect, each of $R^{2a}$, $R^{2b}$, $R^{2c}$, and $R^{2d}$ is independently selected from hydrogen, halogen, —NO$_2$, —CN, —OH, —SH, and —NH$_2$. In a still further aspect, each of $R^{2a}$, $R^{2b}$, $R^{2c}$, and $R^{2d}$ is independently selected from hydrogen, —F, —Cl, —NO$_2$, —CN, —OH, —SH, and —NH$_2$. In yet a further aspect, each of $R^{2a}$, $R^{2b}$, $R^{2c}$, and $R^{2d}$ is independently selected from hydrogen, —F, —Cl, —OH, —SH, and —NH$_2$. In an even further aspect, each of $R^{2a}$, $R^{2b}$, $R^{2c}$, and $R^{2d}$ is independently selected from hydrogen, —F, —Cl, and —OH.

In a further aspect, each of $R^{2a}$, $R^{2b}$, $R^{2c}$, and $R^{2d}$ is independently selected from hydrogen, C1-C4 alkyl, and C1-C4 haloalkyl. In a still further aspect, each of $R^{2a}$, $R^{2b}$, $R^{2c}$, and $R^{2d}$ is independently selected from hydrogen, methyl, ethyl, n-propyl, i-propyl, —CH$_2$Cl, —CH$_2$CH$_2$Cl, —CH$_2$CH$_2$CH$_2$Cl, —CH(CH$_2$Cl)(CH$_3$), —CH$_2$F, —CH$_2$CH$_2$F, —CH$_2$CH$_2$CH$_2$F, and —CH(CH$_2$F)(CH$_3$). In yet a further aspect, each of $R^{2a}$, $R^{2b}$, $R^{2c}$, and $R^{2d}$ is independently selected from hydrogen, methyl, ethyl, —CH$_2$Cl, —CH$_2$CH$_2$Cl, —CH$_2$F, and —CH$_2$CH$_2$F. In an even further aspect, each of $R^{2a}$, $R^{2b}$, $R^{2c}$, and $R^{2d}$ is independently selected from hydrogen, —CH$_2$Cl, and —CH$_2$F.

In a further aspect, each of $R^{2a}$, $R^{2b}$, $R^{2c}$, and $R^{2d}$ is independently selected from hydrogen, halogen, and C1-C4 alkyl. In a still further aspect, each of $R^{2a}$, $R^{2b}$, $R^{2c}$, and $R^{2d}$ is independently selected from hydrogen, methyl, ethyl, n-propyl, and i-propyl. In yet a further aspect, each of $R^{2a}$, $R^{2b}$, $R^{2c}$, and $R^{2d}$ is independently selected from hydrogen, halogen, methyl, and ethyl. In an even further aspect, each of $R^{2a}$, $R^{2b}$, $R^{2c}$, and $R^{2d}$ is independently selected from hydrogen, halogen, and ethyl. In a still further aspect, each of $R^{2a}$, $R^{2b}$, $R^{2c}$, and $R^{2d}$ is independently selected from hydrogen, halogen, and methyl.

In a further aspect, each of $R^{2a}$, $R^{2b}$, $R^{2c}$, and $R^{2d}$ is independently selected from hydrogen, halogen, and C1-C4 haloalkyl. In a still further aspect, each of $R^{2a}$, $R^{2b}$, $R^{2c}$, and $R^{2d}$ is independently selected from hydrogen, —F, —Cl, —CH$_2$Cl, —CH$_2$Cl, —H$_2$CH$_2$CH$_2$, —CH$_2$CH$_2$CH$_2$Cl, —CH(CH$_2$Cl)(CH$_3$), —CH$_2$F, —CH$_2$CH$_2$F, —CH$_2$CH$_2$CH$_2$F, and —CH(CH$_2$F)(CH$_3$). In yet a further aspect, each of $R^{2a}$, $R^{2b}$, $R^{2c}$, and $R^{2d}$ is independently selected from hydrogen, —F, —Cl, —CH$_2$Cl, —CH$_2$CH$_2$Cl, —CH$_2$F, and —CH$_2$CH$_2$F. In an even further aspect, each of $R^{2a}$, $R^{2b}$, $R^{2c}$, and $R^{2d}$ is independently selected from hydrogen, —F, —Cl, —CH$_2$Cl, and —CH$_2$F.

In a further aspect, each of $R^{2a}$, $R^{2b}$, $R^{2c}$, and $R^{2d}$ is independently selected from hydrogen and halogen. In a still further aspect, each of $R^{2a}$, $R^{2b}$, $R^{2c}$, and $R^{2d}$ is independently selected from hydrogen, —F, —Cl, and —Br. In yet a further aspect, each of $R^{2a}$, $R^{2b}$, $R^{2c}$, and $R^{2d}$ is independently selected from hydrogen, —F, and —Cl. In an even further aspect, each of $R^{2a}$, $R^{2b}$, $R^{2c}$, and $R^{2d}$ is independently selected from hydrogen and —F. In a still further aspect, each of $R^{2a}$, $R^{2b}$, $R^{2c}$, and $R^{2d}$ is independently selected from hydrogen and —Cl.

c. $R^{20}$ Groups

In one aspect, $R^{20}$, when present, is selected from hydrogen and C1-C4 alkyl, provided that when $R^{20}$ is C1-C4 alkyl then at least two of $R^{2a}$, $R^{2b}$, $R^{2c}$, and $R^{2d}$ are not hydrogen. In a further aspect, $R^{20}$, when present, is hydrogen.

In one aspect, $R^{20}$, when present, is selected from hydrogen and C1-C4 alkyl.

In a further aspect, $R^{20}$, when present, is selected from hydrogen, methyl, ethyl, n-propyl, i-propyl, n-butyl, i-butyl, sec-butyl, and t-butyl. In a still further aspect, $R^{20}$, when present, is selected from hydrogen, methyl, ethyl, n-propyl, and i-propyl. In yet a further aspect, $R^{20}$, when present, is selected from hydrogen, methyl, and ethyl. In an even further aspect, $R^{20}$, when present, is selected from hydrogen and ethyl. In a still further aspect, $R^{20}$, when present, is selected from hydrogen and methyl.

In a further aspect, $R^{20}$, when present, is selected from methyl, ethyl, n-propyl, i-propyl, n-butyl, i-butyl, sec-butyl, and t-butyl. In a still further aspect, $R^{20}$, when present, is selected from methyl, ethyl, n-propyl, and i-propyl. In yet a further aspect, $R^{20}$, when present, is selected from methyl and ethyl. In an even further aspect, $R^{20}$, when present, is ethyl. In a still further aspect, $R^{20}$, when present, is methyl.

d. $R^{21a}$ and $R^{21b}$ Groups

In one aspect, each of $R^{21a}$ and $R^{21b}$, when present, is independently selected from hydrogen and C1-C4 alkyl. In a further aspect, each of $R^{21a}$ and $R^{21b}$, when present, is hydrogen.

In a further aspect, each of $R^{21a}$ and $R^{21b}$, when present, is independently selected from hydrogen, methyl, ethyl, n-propyl, i-propyl, n-butyl, i-butyl, sec-butyl, and t-butyl. In a still further aspect, each of $R^{21a}$ and $R^{21b}$, when present, is independently selected from hydrogen, methyl, ethyl, n-propyl, and i-propyl. In yet a further aspect, each of $R^{21a}$ and $R^{21b}$, when present, is independently selected from hydrogen, methyl, and ethyl. In an even further aspect, each of $R^{21a}$ and $R^{21b}$, when present, is independently selected from hydrogen and ethyl. In a still further aspect, each of $R^{21a}$ and $R^{21b}$, when present, is independently selected from hydrogen and methyl.

In a further aspect, each of $R^{21a}$ and $R^{21b}$, when present, is independently selected from methyl, ethyl, n-propyl, i-propyl, n-butyl, i-butyl, sec-butyl, and t-butyl. In a still further aspect, each of $R^{21a}$ and $R^{21b}$, when present, is independently selected from methyl, ethyl, n-propyl, and i-propyl. In yet a further aspect, each of $R^{21a}$ and $R^{21b}$, when present, is independently selected from methyl and ethyl. In an even further aspect, each of $R^{21a}$ and $R^{21b}$, when present, is ethyl. In a still further aspect, each of $R^{21a}$ and $R^{21b}$, when present, is methyl.

In a further aspect, $R^{21a}$, when present, is hydrogen, and $R^{21b}$, when present, is C1-C4 alkyl. In a still further aspect, $R^{21a}$, when present, is hydrogen, and $R^{21b}$, when present, is selected from methyl, ethyl, n-propyl, and i-propyl. In yet a further aspect, $R^{21a}$, when present, is hydrogen, and $R^{21b}$, when present, is selected from methyl and ethyl. In an even further aspect, $R^{21a}$, when present, is hydrogen, and $R^{21b}$, when present, is ethyl. In a still further aspect, $R^{21a}$, when present, is hydrogen, and $R^{21b}$, when present, is methyl.

2. Example Compounds

In one aspect, a compound can be present as one or more of the following structures:

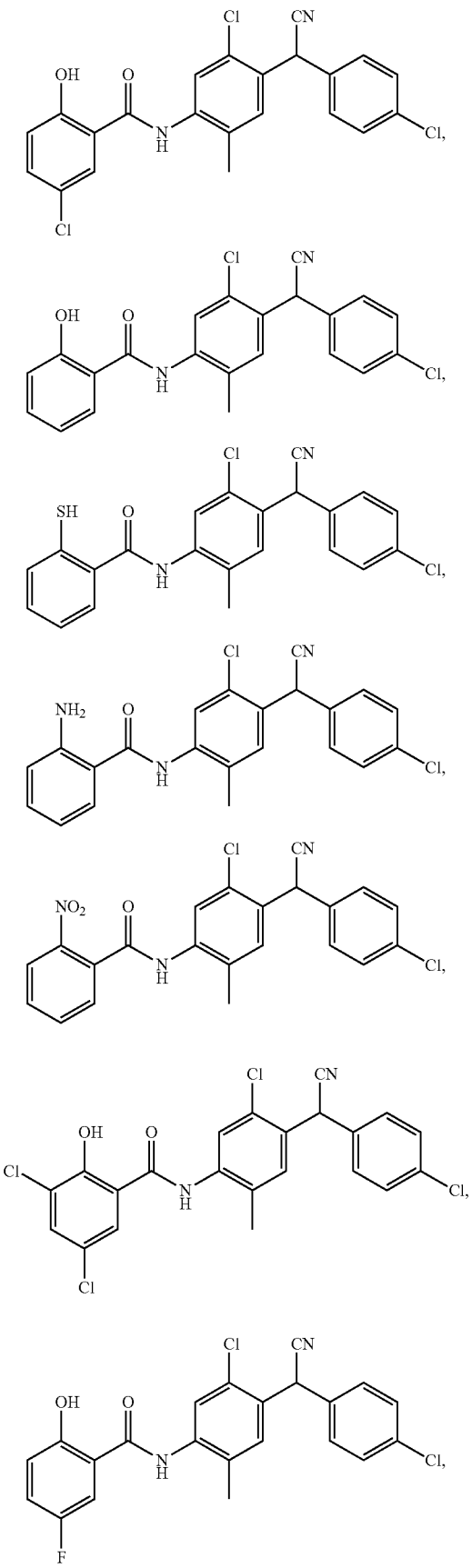

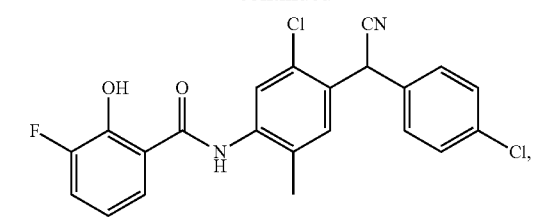

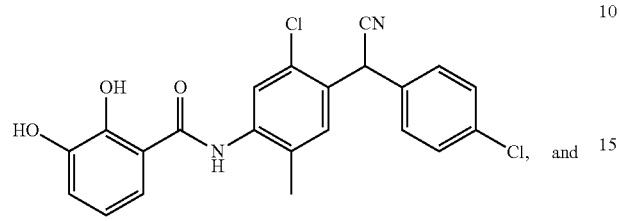

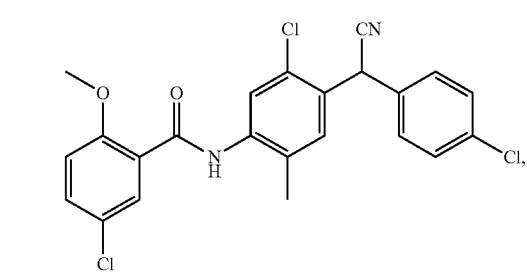

or a pharmaceutically acceptable salt thereof.

In one aspect, a compound can be present as one or more of the following structures:

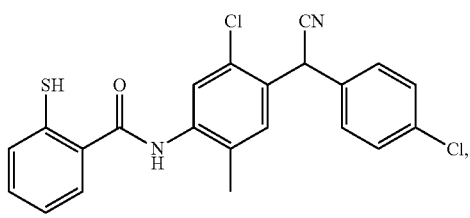

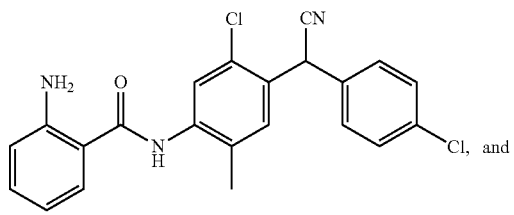

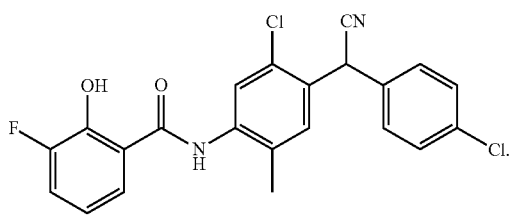

or a pharmaceutically acceptable salt thereof.

In one aspect, a compound can be present as one or more of the following structures:

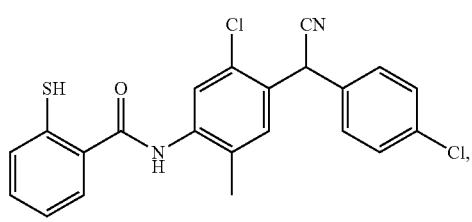

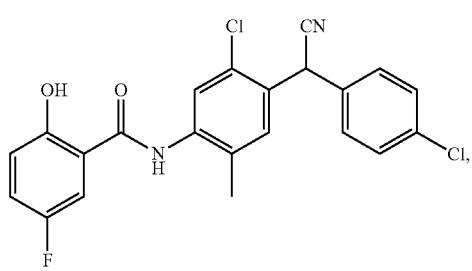

or a pharmaceutically acceptable salt thereof.

In one aspect, a compound can be present as one or more of the following structures:

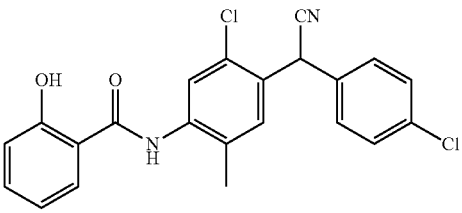

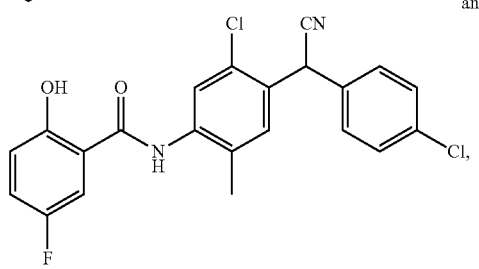

or a pharmaceutically acceptable salt thereof.

In one aspect, a compound can be present as one or more of the following structures:

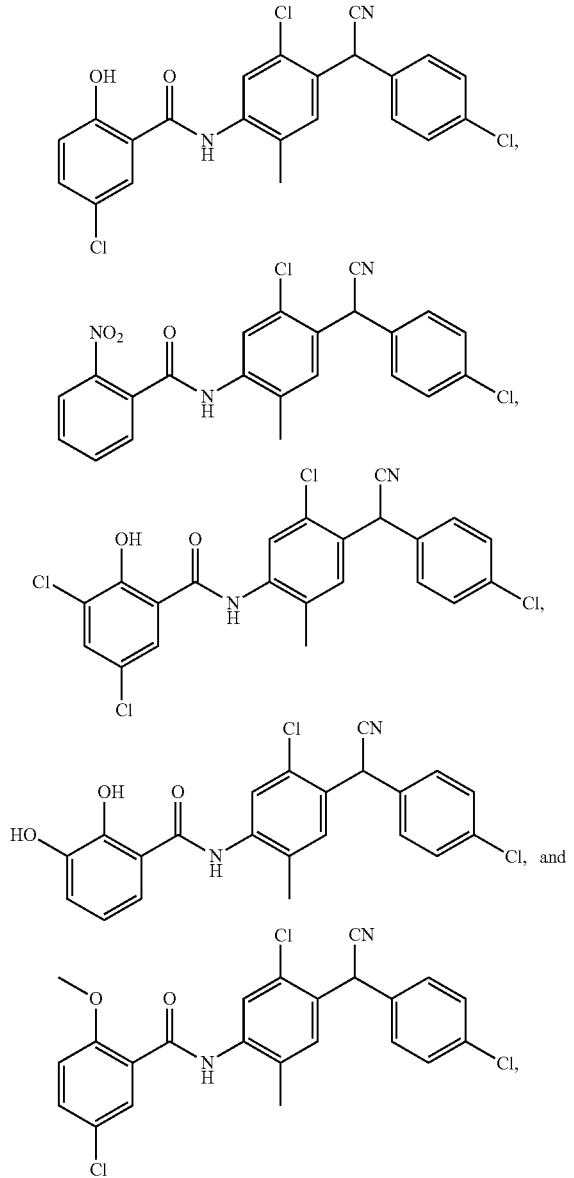

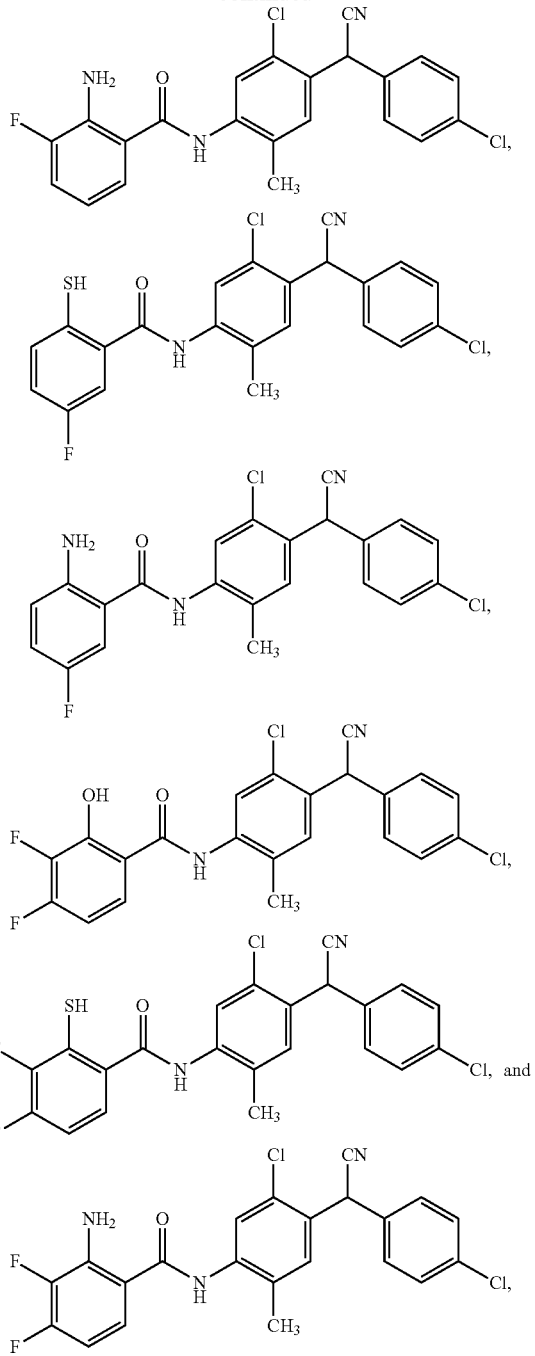

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of SPAK kinase function, and such activity can be determined using the assay methods described herein.

In one aspect, a compound can be selected from:

or a pharmaceutically acceptable salt thereof.

In one aspect, a compound can be selected from:

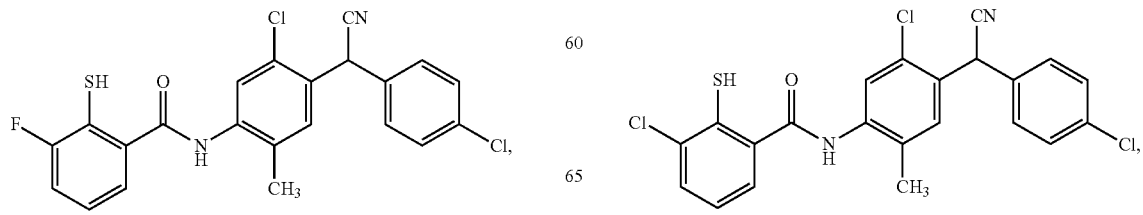

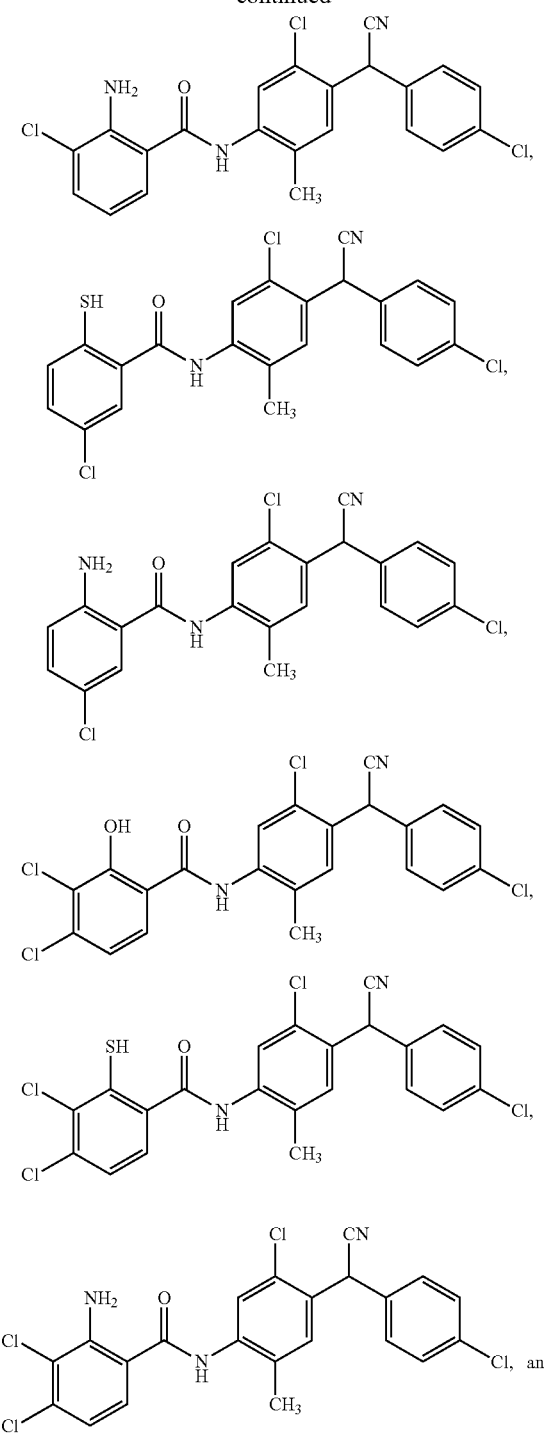
or a pharmaceutically acceptable salt thereof.
In one aspect, a compound can be selected from:
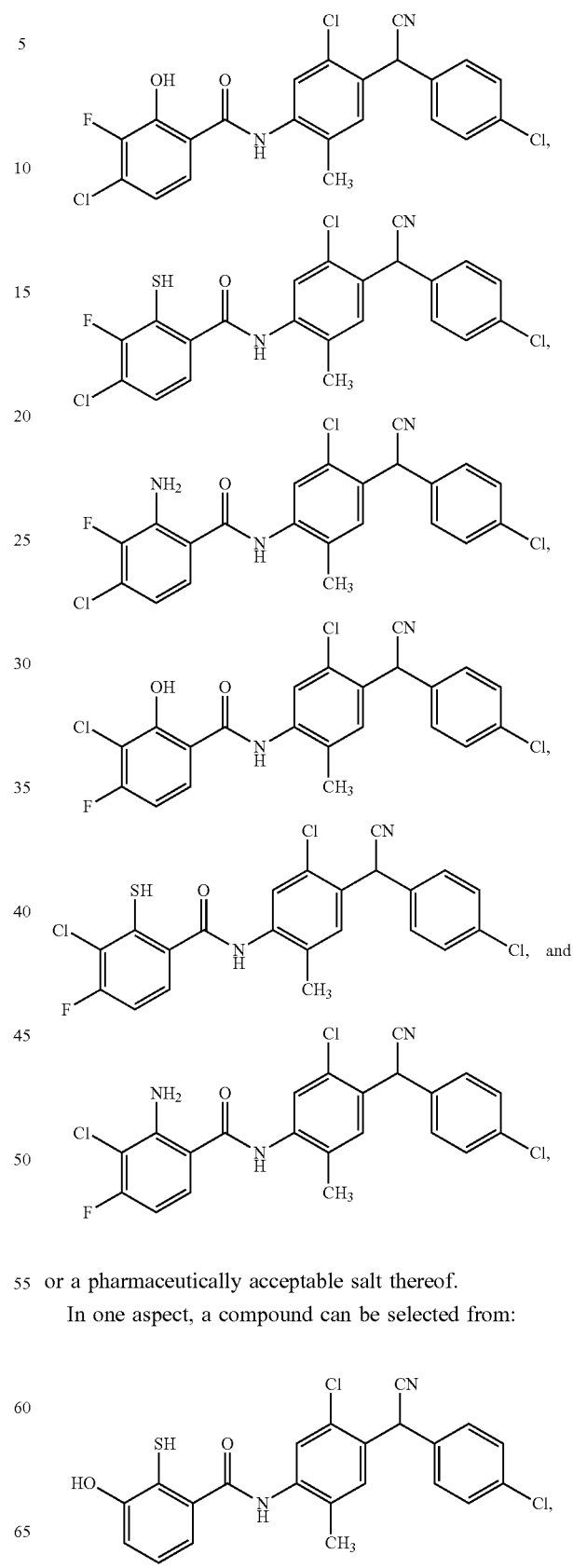
or a pharmaceutically acceptable salt thereof.
In one aspect, a compound can be selected from:

-continued

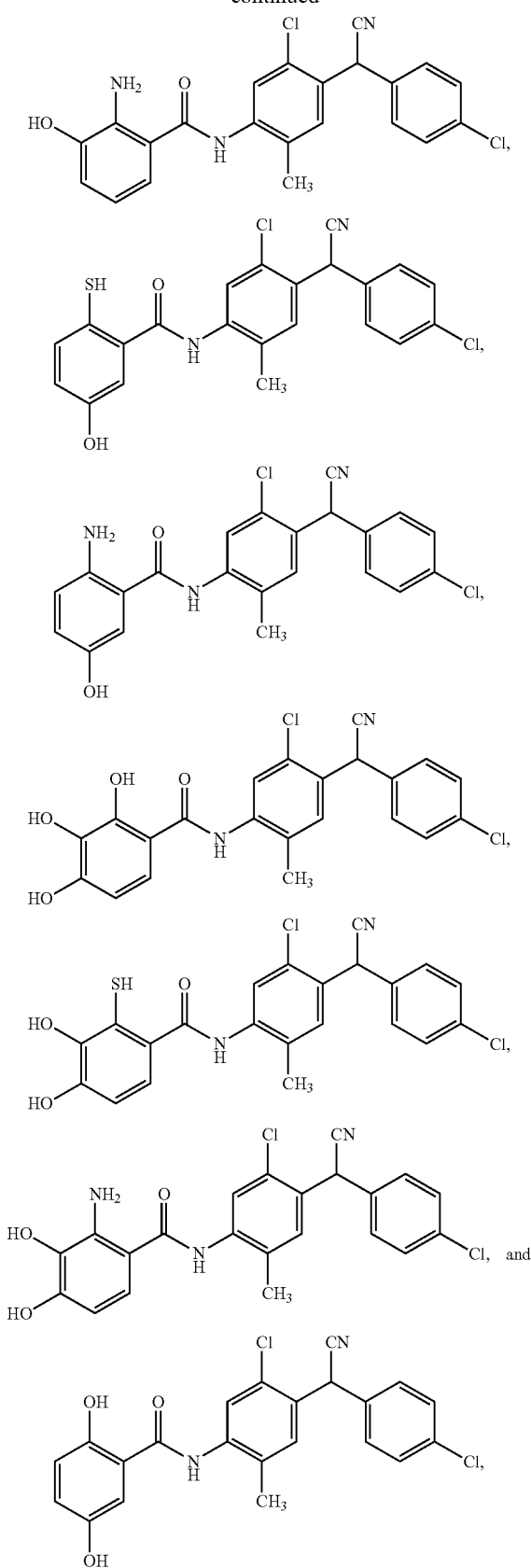

or a pharmaceutically acceptable salt thereof.

In one aspect, a compound can be selected from:

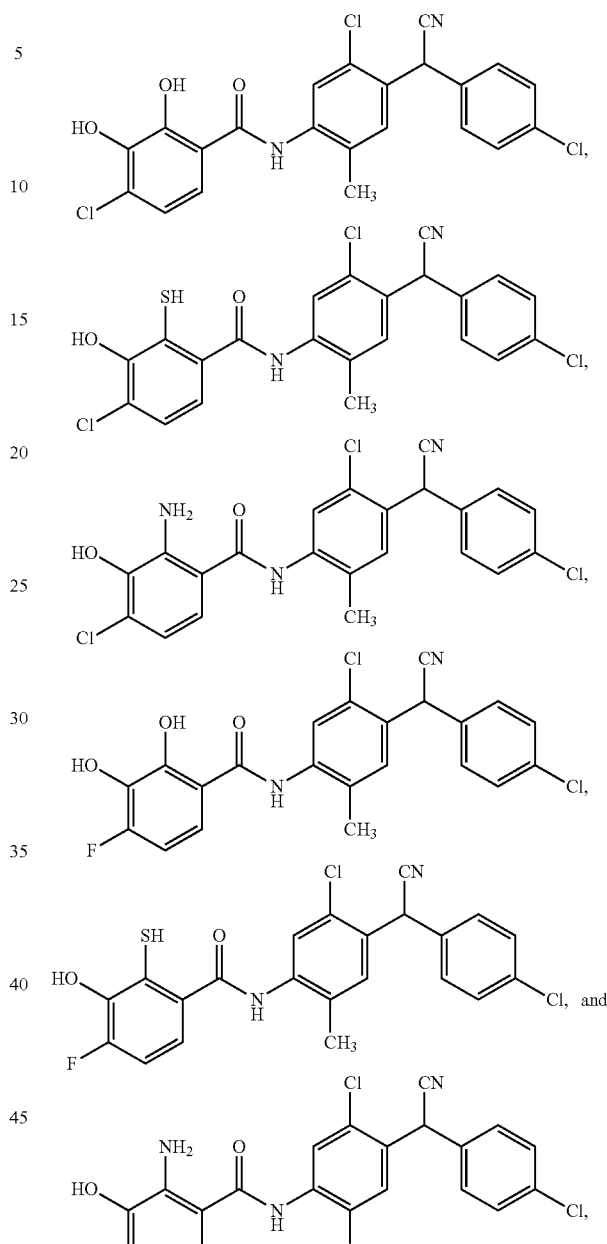

or a pharmaceutically acceptable salt thereof.

C. Pharmaceutical Compositions

In one aspect, disclosed are pharmaceutical compositions comprising at least one disclosed compound and a pharmaceutically acceptable carrier. In a further aspect, a pharmaceutical composition can be provided comprising a therapeutically effective amount of at least one disclosed compound. In a still further aspect, a pharmaceutical composition can be provided comprising a prophylactically effective amount of at least one disclosed compound. In yet a further aspect, the invention relates to pharmaceutical compositions comprising a pharmaceutically acceptable carrier and a compound, wherein the compound is present in an effective amount.

Thus, in one aspect, disclosed are pharmaceutical compositions comprising a therapeutically effective amount of at least one compound having a structure represented by a formula:

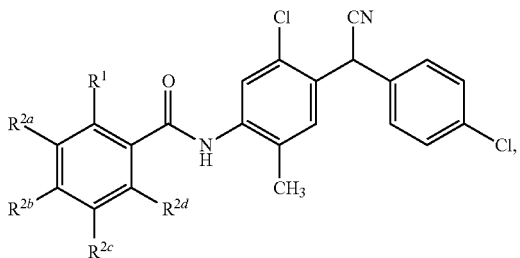

wherein $R^1$ is selected from —OH, —$SR^{20}$, and —$NR^{21a}R^{21b}$; wherein $R^{20}$, when present, is selected from hydrogen and C1-C4 alkyl; wherein each of $R^{21a}$ and $R^{21b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH then $R^{2c}$ is hydrogen, and provided that when $R^{20}$ is C1-C4 alkyl then at least two of $R^{2a}$, $R^{2b}$, $R^{2c}$, and $R^{2d}$ are not hydrogen, or a pharmaceutically acceptable salt thereof, and a pharmaceutically acceptable carrier.

Also disclosed are pharmaceutical compositions comprising a therapeutically effective amount of at least one compound selected from:

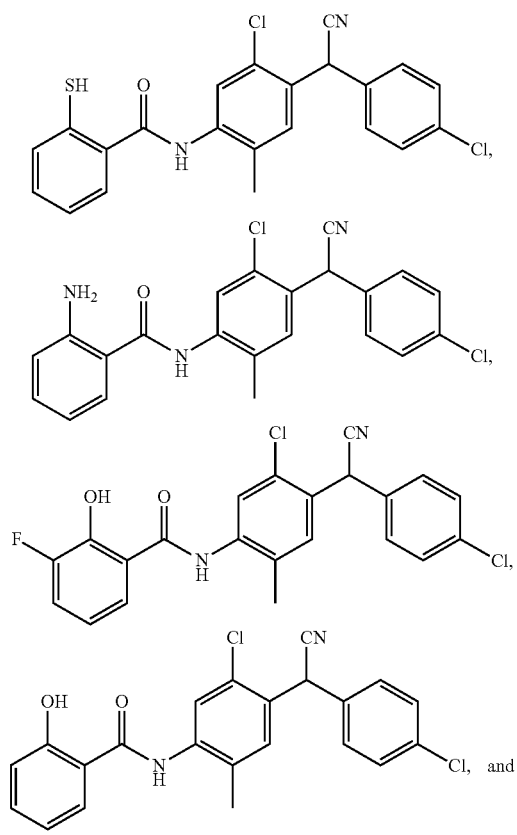

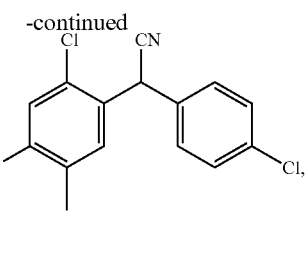

or a pharmaceutically acceptable salt thereof.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In a further aspect, the pharmaceutical composition is administered to a mammal. In a still further aspect, the mammal is a human. In an even further aspect, the human is a patient.

In a further aspect, the pharmaceutical composition is administered following identification of the mammal in need of treatment of cancer. In a still further aspect, the mammal has been diagnosed with a need for treatment of cancer prior to the administering step.

In a further aspect, the pharmaceutical composition is administered following identification of the mammal in need of treatment of a fibrotic disorder. In a still further aspect, the mammal has been diagnosed with a need for treatment of a fibrotic disorder prior to the administering step.

In a further aspect, the pharmaceutical composition is administered following identification of the mammal in need of immunotherapy. In a still further aspect, the mammal has been diagnosed with a need for immunotherapy prior to the administering step.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The compounds of the present disclosure alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1, 3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbents and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, $4^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the inhibition of SPAK kinase function. The method also includes the administration of a therapeutically effect amount of the compound for the treatment of patient having a predisposition for being afflicted with a disorder or condition associated with SPAK kinase function. The dose administered to an animal, particularly a human, in the context of the present invention should be sufficient to affect a therapeutic response in the animal over a reasonable timeframe. One skilled in the art will recognize that dosage will depend upon a variety of factors including the condition of the animal, the body weight of the animal, as well as the severity and stage of the condition.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

In a further aspect, the composition further comprises at least one agent associated with the treatment of a hypoxic brain injury. Examples of an agent associated with the treatment of a hypoxic brain injury include, but are not limited to, thrombolytics, oxygen, antihypertensives, insulin, antipyretics, anticoagulants, and antiplatelet agents. In a still further aspect, the hypoxic brain injury is due to ischemic stroke.

In a further aspect, the composition further comprises at least one agent known to have a side effect of increasing the risk of hypoxic brain injury.

It is understood that the disclosed compositions can be prepared from the disclosed compounds. It is also understood that the disclosed compositions can be employed in the disclosed methods of using.

D. Methods of Making the Compounds

In various aspects, the inventions relates to methods of making N-(5-chloro-4-((4-chlorophenyl)(cyano)methyl)-2-methylphenyl)benzamide compounds useful in the treatment of conditions or disorders associated with a dysregulation of SPAK kinase function including, but not limited to, hypoxic brain injuries due to, for example, traumatic brain injury, ischemic stroke, carbon monoxide poisoning, drowning, choking, suffocating, or cardiac arrest. Thus, in one aspect, disclosed are methods of making a disclosed compound.

Compounds according to the present disclosure can, for example, be prepared by the several methods outlined below. A practitioner skilled in the art will understand the appropriate use of protecting groups [see: Greene and Wuts, Protective Groups in Organic Synthesis] and the preparation of known compounds found in the literature using the standard methods of organic synthesis. There may come from time to time the need to rearrange the order of the recommended synthetic steps; however, this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, N-(5-chloro-4-((4-chlorophenyl)(cyano) methyl)-2-methylphenyl)benzamide compounds can be prepared as shown below.

SCHEME 1A.

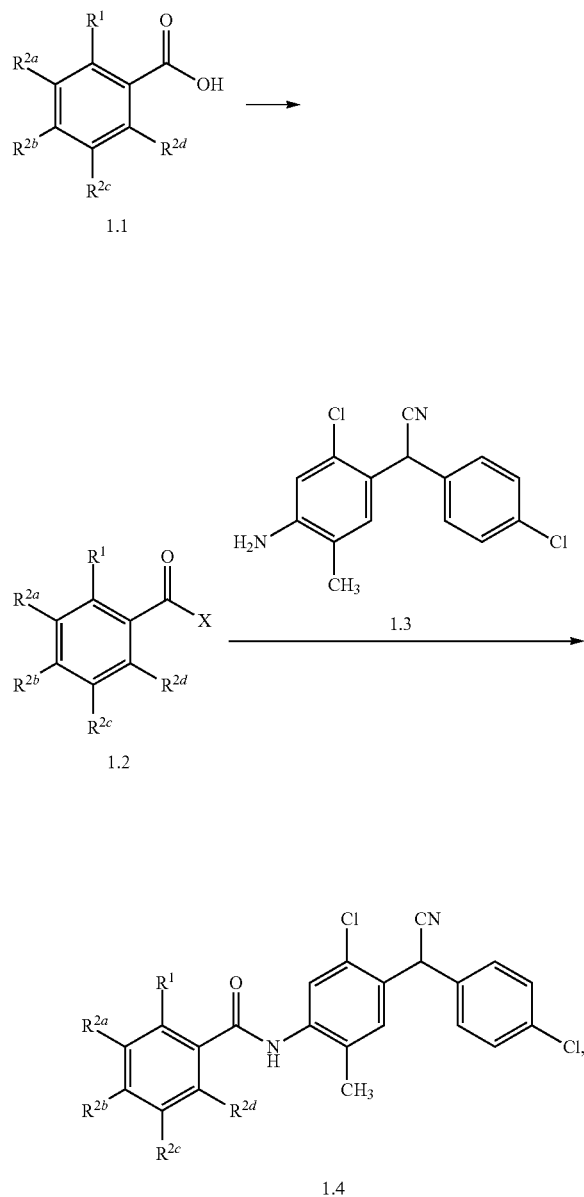

Compounds are represented in generic form, with substituents as noted in compound descriptions elsewhere herein and wherein X is a halogen. A more specific example is set forth below.

SCHEME 1B.

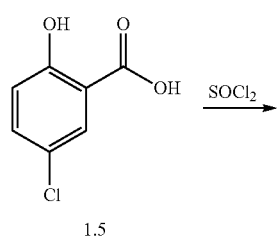

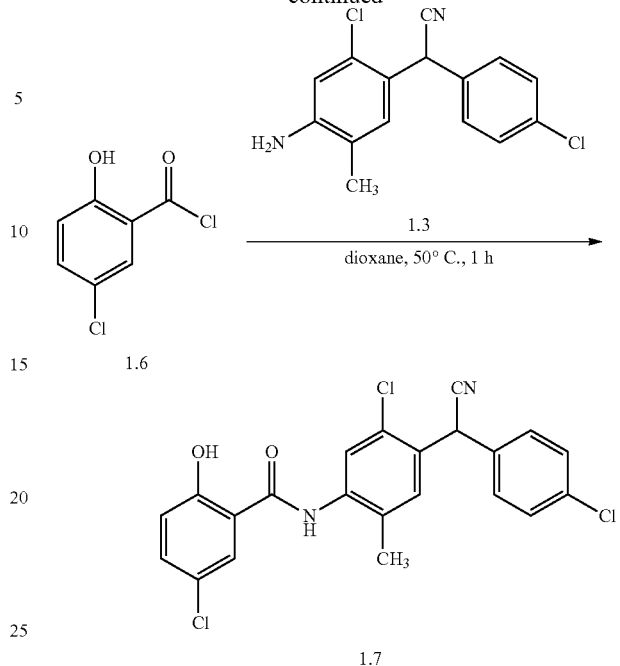

In one aspect, compounds of type 1.7, and similar compounds, can be prepared according to reaction Scheme 1B above. Thus, compounds of type 1.6 can be prepared by a nucleophilic substitution reaction of an appropriate carboxylic acid, e.g., 1.5 as shown above, and an appropriate activating agent, e.g., thionyl chloride as shown above. Appropriate carboxylic acids and appropriate activating agents are commercially available or prepared by methods known to one skilled in the art. Compounds of type 1.7 can be prepared by a coupling reaction between an appropriate activated carbonyl compound, e.g., 1.6 as shown above, and an appropriate amine, e.g., 1.3 as shown above. Appropriate amines are commercially available or prepared by methods known to one skilled in the art. The coupling reaction is carried out in the presence of an appropriate solvent, e.g., dioxane, for an appropriate period of time, e.g., 1 hour, at an appropriate temperature, e.g., 50° C. As can be appreciated by one skilled in the art, the above reaction provides an example of a generalized approach wherein compounds similar in structure to the specific reactants above (compounds similar to compounds of type 1.1, 1.2, and 1.3), can be substituted in the reaction to provide substituted N-(5-chloro-4-((4-chlorophenyl)(cyano)methyl)-2-methylphenyl) benzamide compounds similar to Formula 1.4.

E. Methods of Using the Compounds

The compounds and pharmaceutical compositions of the invention are useful in treating or controlling conditions or disorders associated with a dysregulation of SPAK kinase function including, but not limited to, hypoxic brain injuries due to, for example, traumatic brain injury, ischemic stroke, carbon monoxide poisoning, drowning, choking, suffocating, or cardiac arrest. In a further aspect, the hypoxic brain injury is due to ischemic stroke or traumatic brain injury. In a still further aspect, the hypoxic brain injury is due to ischemic stroke.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a cancer, immune dysfunction, or of a fibrotic disorder.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a hypoxic brain injury.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling conditions or disorders associated with a dysregulation of SPAK kinase function including, but not limited to, hypoxic brain injuries due to, for example, traumatic brain injury, ischemic stroke, carbon monoxide poisoning, drowning, choking, suffocating, or cardiac arrest. Thus, provided is a method comprising administering a therapeutically effective amount of a composition comprising a disclosed compound to a subject. In a further aspect, the method can be a method for treating a hypoxic brain injury.

a. Treating a Hypoxic Brain Injury

In one aspect, disclosed are methods of treating a hypoxic brain injury associated with SPAK kinase function in a mammal, the method comprising the step of administering to the mammal an effective amount of at least one disclosed compound, or a pharmaceutically acceptable salt thereof.

Thus, in one aspect, disclosed are methods for treating a hypoxic brain injury in a subject, the method comprising the step of administering to the subject an effective amount of at least one compound having a structure represented by a formula:

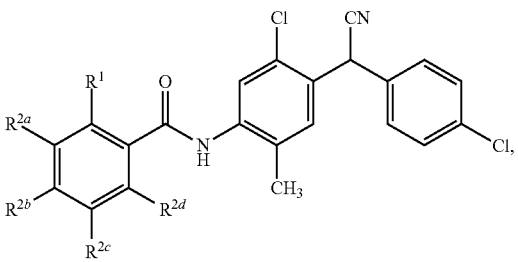

wherein $R^1$ is selected from —OH, —SR$^{20}$, and —NR$^{21a}$R$^{21b}$; wherein R$^{20}$, when present, is selected from hydrogen and C1-C4 alkyl; wherein each of R$^{21a}$ and R$^{21b}$, when present, is independently selected from hydrogen and C1-C4 alkyl; wherein each of R$^{2a}$, R$^{2b}$, R$^{2c}$, and R$^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when R$^1$ is —OH and each of R$^{2b}$ and R$^{2d}$ is hydrogen then neither of R$^{2a}$ and R$^{2c}$ is halogen, or a pharmaceutically acceptable salt thereof.

A hypoxic brain injury can be caused by or due to, for example, traumatic brain injury, ischemic stroke, carbon monoxide poisoning, drowning, choking, suffocating, or cardiac arrest.

In a further aspect, the hypoxic brain injury is caused by or due to a traumatic brain injury or ischemic stroke. In a still further aspect, the hypoxic brain injury is caused by or due to ischemic stroke.

In a further aspect, the subject has been diagnosed with a need for treatment of a hypoxic brain injury prior to the administering step.

In a further aspect, the subject is a mammal. In a still further aspect, the mammal is a human.

In a further aspect, the effective amount is a therapeutically effective amount. In a still further aspect, the effective amount is a prophylactically effective amount.

In a further aspect, the hypoxic brain injury is associated with dysregulation of SPAK kinase.

In a further aspect, the method further comprises the step of identifying a subject in need of treatment of a hypoxic brain injury.

In a further aspect, the method further comprises the step of administering a therapeutically effective amount of at least one agent associated with the treatment of a hypoxic brain injury. Examples of agents associated with the treatment of hypoxic brain injuries include, but are not limited to, thrombolytics (e.g., anistrplase, reteplase, streptokinase, kabikinase, tenecteplase, rokinase), oxygen, antihypertensives (e.g., ACE inhibitors such as benazepril, captopril, enalapril, fosinopril, Lisinopril, moexipril, perindopril, and quinapril; angiotensin II receptor blockers such as azilsartan, candesartan, eprosartan, irbesartan, losartan, olmesartan, telmisartan, and valsartan; beta blockers such as acebutolol, atenolol, bisoprolol, metoprolol, nadolol, nebivolol, and propranolol; calcium channel blockers such as amlodipine, diltiazem, felodipine, isradipine, nicardipine, nifedipine, nisoldipine, and verapamil; direct renin inhibitors such as aliskiren; and diuretics), insulin, antipyretics (e.g., salicylates such as acetylsalicylic acid, choline salicylate, magnesium salicylate, and sodium salicylate; acetaminophen; and nonsteroidal anti-inflammatory drugs such as ibuprofen, naproxen, and ketoprofen), anticoagulants (e.g., heparin, warfarin, rivaroxaban, dabigatran, apixaban, edoxaban, enoxaparin, fondaparinux), and antiplatelet agents (e.g., clopidogrel, ticagrelor, prasugrel, dipyridamole, dipyridamole/aspirin, ticlodipine, and eptfibatide).

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Methods for Modifying SPAK Kinase Function in a Subject

In one aspect, disclosed are methods for modifying SPAK kinase function in a subject, the method comprising the step of administering to the subject an effective amount of a compound having a structure represented by a formula:

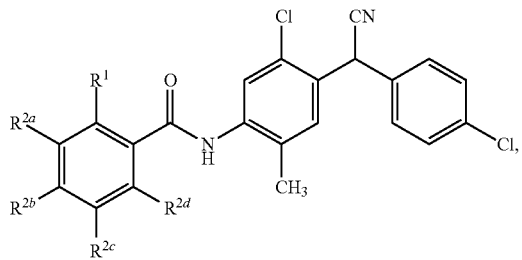

wherein $R^1$ is selected from —OH, —SR$^{20}$, and —NR$^{21a}$R$^{21b}$; wherein R$^{20}$, when present, is selected from hydrogen and C1-C4 alkyl; wherein each of $R^{21a}$ and $R^{21b}$, when present, is independently selected from hydrogen and C1-C4 alkyl; wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH and each of $R^{2b}$ and $R^{2d}$ is hydrogen then neither of $R^{2a}$ and $R^{2c}$ is halogen, or a pharmaceutically acceptable salt thereof.

In one aspect, disclosed are methods of modifying SPAK kinase function in a mammal, the method comprising the step of administering to the mammal a therapeutically effective amount of at least one disclosed compound, or a pharmaceutically acceptable salt thereof.

In a further aspect, the compound exhibits inhibition of SPAK kinase function. In a still further aspect, the compound exhibits a decrease in SPAK kinase function.

In a further aspect, the subject is a mammal. In a still further aspect, the subject is a human.

In a further aspect, the subject has been diagnosed with a hypoxic brain injury prior to the administering step. In a still further aspect, the method further comprises the step of identifying a subject in need of treatment of a hypoxic brain injury prior to the administering step.

In a further aspect, the subject has been diagnosed with a need for modifying SPAK kinase function prior to the administering step. In a further aspect, the subject has been diagnosed with a need for inhibiting SPAK kinase function prior to the administering step.

In a further aspect, the subject has been diagnosed with a need for treatment of the disorder associated with SPAK kinase function prior to the administering step. In a still further aspect, the subject has been diagnosed with a need for treatment of the disorder associated with SPAK kinase dysfunction prior to the administering step. In yet a further aspect, the method further comprises the step of identifying a subject in need of treatment of a disorder associated with SPAK kinase function. In an even further aspect, the method further comprises the step of identifying a subject in need of treatment of a disorder associated with SPAK kinase dysfunction.

3. Methods for Modifying SPAK Kinase Function in at Least One Cell

In one aspect, disclosed are methods for modifying SPAK kinase function in at least one cell, the method comprising the step of contacting the at least one cell with an effective amount of at least one disclosed compound, or a pharmaceutically acceptable salt thereof.

In one aspect, disclosed are methods for modifying SPAK kinase function in at least one cell, the method comprising the step of administering to the subject an effective amount of a compound having a structure represented by a formula:

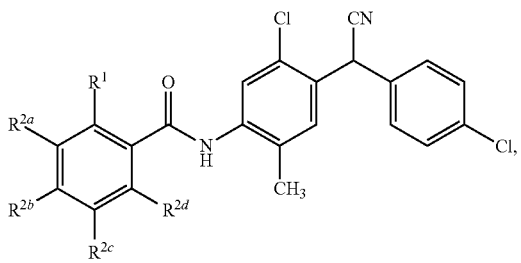

wherein $R^1$ is selected from —OH, —SR$^{20}$, and —NR$^{21a}$R$^{21b}$; wherein R$^{20}$, when present, is selected from hydrogen and C1-C4 alkyl; wherein each of $R^{21a}$ and $R^{21b}$, when present, is independently selected from hydrogen and C1-C4 alkyl; wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH and each of $R^{2b}$ and $R^{2d}$ is hydrogen then neither of $R^{2a}$ and $R^{2c}$ is halogen, or a pharmaceutically acceptable salt thereof.

In a further aspect, modifying is decreasing. In a still further aspect, modifying is inhibiting.

In a further aspect, the cell is mammalian. In a still further aspect, the cell is human. In yet a further aspect, the cell has been isolated from a mammal prior to the contacting step.

In a further aspect, contacting is via administration to a mammal.

In a further aspect, the subject has been diagnosed with a hypoxic brain injury prior to the administering step. In a still further aspect, the method further comprises the step of identifying a subject in need of treatment of a hypoxic brain injury prior to the administering step.

In a further aspect, the subject has been diagnosed with a need for modifying SPAK kinase function prior to the administering step. In a further aspect, the subject has been diagnosed with a need for inhibiting SPAK kinase function prior to the administering step.

In a further aspect, the subject has been diagnosed with a need for treatment of the disorder associated with SPAK kinase function prior to the administering step. In a still further aspect, the subject has been diagnosed with a need for treatment of the disorder associated with SPAK kinase dysfunction prior to the administering step. In yet a further aspect, the method further comprises the step of identifying a subject in need of treatment of a disorder associated with SPAK kinase function. In an even further aspect, the method further comprises the step of identifying a subject in need of treatment of a disorder associated with SPAK kinase dysfunction.

4. Use of Compounds

In one aspect, the invention relates to the use of a disclosed compound or a product of a disclosed method. In a further aspect, a use relates to the manufacture of a medicament for the treatment of a hypoxic brain injury in a mammal.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder or condition in a mammal. Also disclosed is the use of a compound for modification of SPAK kinase function. In one aspect, the use is characterized in that the mammal is a human. In one aspect, the use is characterized in that the disorder or condition is a hypoxic brain injury. In one aspect, the hypoxic brain injury is due to ischemic stroke.

In a further aspect, the use relates to the manufacture of a medicament for the treatment of a hypoxic brain injury in a mammal.

In a further aspect, the use relates to modulation of SPAK kinase function in a mammal. In a further aspect, the use relates to inhibition of SPAK kinase function in a mammal. In a still further aspect, the use relates to modulation of SPAK kinase function in a cell. In yet a further aspect, the mammal is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a hypoxic brain injury in a mammal. In a further aspect, the hypoxic brain injury is due to ischemic stroke.

5. Manufacture of a Medicament

In one aspect, the invention relates to a method for the manufacture of a medicament for treating a disorder or condition associated with SPAK kinase function in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of SPAK kinase function. The dose administered to an animal, particularly a human, in the context of the present invention should be sufficient to affect a therapeutic response in the animal over a reasonable timeframe. One skilled in the art will recognize that dosage will depend upon a variety of factors including, for example, the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

6. Kits

In one aspect, disclosed are kits comprising a compound having a structure represented by a formula:

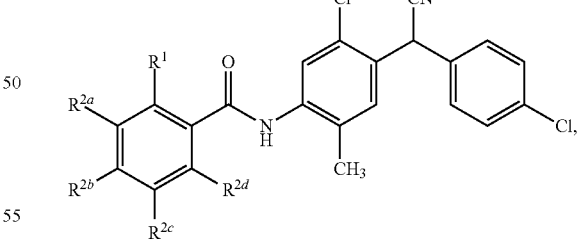

wherein $R^1$ is selected from —OH, —SR$^{20}$, and —NR$^{21a}$R$^{21b}$; wherein R$^{20}$, when present, is selected from hydrogen and C1-C4 alkyl; wherein each of R$^{21a}$ and R$^{21b}$, when present, is independently selected from hydrogen and C1-C4 alkyl; wherein each of R$^{2a}$, R$^{2b}$, R$^{2c}$, and R$^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH and each of $R^{2b}$ and $R^{2d}$ is hydrogen then neither of $R^{2a}$ and $R^{2c}$ is halogen, or a pharmaceutically acceptable salt thereof, and one or more of: (a) at least one agent associated with the treatment of a hypoxic brain injury; (b) instructions for administering the compound in connection with treating a hypoxic brain injury; and (c) instructions for treating a hypoxic brain injury.

Hypoxic brain injuries can be caused by or due to, for example, traumatic brain injury, ischemic stroke, carbon monoxide poisoning, drowning, choking, suffocating, or cardiac arrest. In a further aspect, the hypoxic brain injury is due to traumatic brain injury or ischemic stroke. In a still further aspect, the hypoxic brain injury is due to ischemic stroke.

Examples of agents associated with the treatment of hypoxic brain injuries include, but are not limited to, thrombolytics (e.g., anistrplase, reteplase, streptokinase, kabikinase, tenecteplase, rokinase), oxygen, antihypertensives (e.g., ACE inhibitors such as benazepril, captopril, enalapril, fosinopril, Lisinopril, moexipril, perindopril, and quinapril; angiotensin II receptor blockers such as azilsartan, candesartan, eprosartan, irbesartan, losartan, olmesartan, telmisartan, and valsartan; beta blockers such as acebutolol, atenolol, bisoprolol, metoprolol, nadolol, nebivolol, and propranolol; calcium channel blockers such as amlodipine, diltiazem, felodipine, isradipine, nicardipine, nifedipine, nisoldipine, and verapamil; direct renin inhibitors such as aliskiren; and diuretics), insulin, antipyretics (e.g., salicylates such as acetylsalicylic acid, choline salicylate, magnesium salicylate, and sodium salicylate; acetaminophen; and nonsteroidal anti-inflammatory drugs such as ibuprofen, naproxen, and ketoprofen), anticoagulants (e.g., heparin, warfarin, rivaroxaban, dabigatran, apixaban, edoxaban, enoxaparin, fondaparinux), and antiplatelet agents (e.g., clopidogrel, ticagrelor, prasugrel, dipyridamole, dipyridamole/aspirin, ticlodipine, and eptfibatide). Thus, in a further aspect, the agent associated with the treatment of a hypoxic brain injury is selected from a thrombolytic, oxygen, an antihypertensive, insulin, an antipyretic, an anticoagulant, and an antiplatelet agent.

In a further aspect, the at least one compound and the at least one agent are co-formulated. In a further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. Examples

Here, the development of a "dual" CCC modulator (NKCC1 inhibitor/KCC activator), 5-chloro-N-(5-chloro-4-((4-chlorophenyl)(cyano)methyl)-2-methylphenyl)-2-hydroxybenzamide ("ZT-1a") that potently and selectively inhibits SPAK kinase—the CCC master regulator—is disclosed. ZT-1a-mediated SPAK inhibition leads to reduced cellular ion influx and stimulated cellular Cl$^-$ extrusion by simultaneous reduction of the activating phosphorylation of NKCC1 and the inhibitory phosphorylation of the KCCs. Intracerebroventricular delivery of ZT-1a normalizes CSF hypersecretion in hemorrhagic hydrocephalus by decreasing SPAK-mediated phosphorylation of NKCC1 and KCC4 in choroid plexus. Systemic ZT-1a administration after experimental ischemic stroke attenuates cerebral infarction and edema and improves neurological outcomes. Without wishing to be bound by theory, these results suggest ZT-1a holds promise as an effective kinase-cotransporter modulator capable of restoring brain water homeostasis and improving neurological function in vivo.

The following preparations and examples are given to enable those skilled in the art to more clearly understand and to practice the present invention. They should not be considered as limiting the scope of the invention, but merely as being illustrative and representative.

1. General Chemistry Experimental Methods

Reagents and solvents were obtained from commercial sources and were used without further purification. Reactions were monitored by thin layer chromatography (TLC) on glass plates coated with silica gel with fluorescent indicator. Compounds were purified either by chromatography on silica gel or by preparative high performance liquid chromatography (HPLC). Silica gel chromatography was performed on the Teledyne ISCO CombiFlash system (RF200) eluting with petroleum ether/ethyl acetate (PE/EA) or dichloromethane/methanol (DCM/MeOH). Preparative HPLC was conducted on the Waters autopurification system consisting of a 2767 sample manager, a 2545 binary gradient module, a 2489 UV detector, and a 3100 mass detector. NMR spectra were recorded on a Bruker Ultrashield Plus-600 (600 MHz) spectrometer and chemical shifts are reported in δ (ppm). $^1$H chemical shifts are reported as s (singlet), d (doublet), dd (doublet of doublet), t (triplet), q (quartet), m (multiplet), and brs (broad singlet) and are referenced to the residual solvent signal: DMSO-d$_6$ (2.50). $^{13}$C spectra are referenced to the residual solvent signal: DMSO-d$_6$ (39.52). High Resolution Mass Spectra were obtained on a Thermo Fisher Scientific LTQ FTICR-MS. The purity of all tested compounds was >95% by HPLC.

2. General Synthesis of Compounds 1a-1j

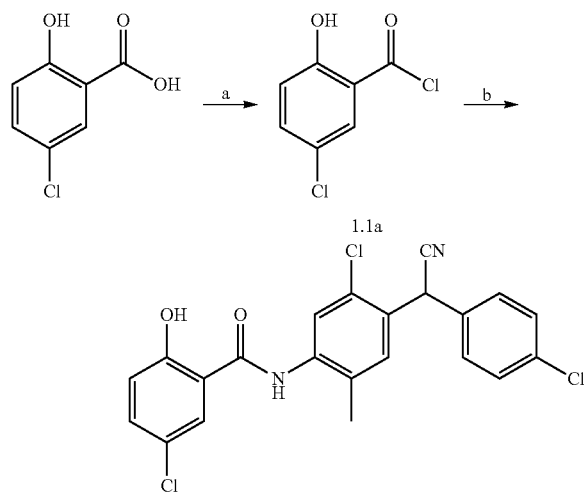

Reagents and conditions: a) SOCl₂, reflux; b) 2-(4-amino-2-chloro-5-methylphenyl)-2-(4-chlorophenyl) acetonitrile, Dioxane, 50° C., 1 h.

A. Preparation of 5-chloro-2-hydroxybenzoyl chloride (I-1a)

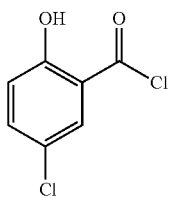

The mixture of 5-chloro-2-hydroxy-benzoic acid (103.5 mg, 0.6 mmol) in 1.5 mL of thionyl chloride was refluxed at 80° C. for 2 h. The resulting solution was cooled down to room temperature and the excess thionyl chloride was removed under vacuum to afford I-1a as a gummy yellow solid. Then I-1a was directly used in next step.

b. 5-chloro-N-(5-chloro-4-((4-chlorophenyl)(cyano)methyl)-2-methylphenyl)-2-hydroxy-benzamide (1a; ZT-1a)

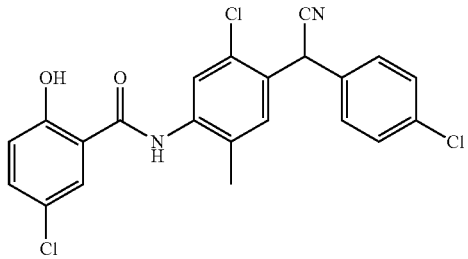 [SMILES: Cc1cc(C(C#N)c2ccc(Cl)cc2)c(Cl)cc1NC(=O)c1cc(Cl)ccc1O]

To a stirred solution of 2-(4-amino-2-chloro-5-methylphenyl)-2-(4-chlorophenyl)acetonitrile (87.3 mg, 0.3 mmol) in 1,4-dioxane (4 mL) was added I-1a (85.9 mg, 0.45 mmol) at room temperature, and the resulting mixture was heated at 50° C. for 1 h. Then the reaction was cooled to room temperature and extracted with ethyl acetate (20 mL). The organic extract was washed with brine (20 mL), dried over anhydrous MgSO₄, and concentrated in vacuum. The crude solid was purified by column chromatography on silica gel (dichloromethane/petroleum ether=3/1) to afford 1a as white crystals, with a yield of 60.9 mg, 45%. ¹H NMR (600 MHz, DMSO-d₆) δ 12.20 (s, 1H), 10.48 (s, 1H), 8.29 (s, 1H), 7.96 (d, J=2.8 Hz, 1H), 7.53-7.48 (m, 4H), 7.40 (d, J=8.5 Hz, 2H), 7.07 (d, J=8.8 Hz, 1H), 5.89 (s, 1H), 2.34 (s, 3H). ¹³C NMR (150 MHz, DMSO-d₆) δ 163.6, 156.1, 138.4, 134.3, 133.8, 133.4, 131.9, 130.1, 130.0, 129.6, 129.4, 128.9, 123.9, 123.4, 120.2, 119.5, 38.5, 17.7. MS (ESI) m/z: 445[M+H]⁺. HRMS (ESI) calculated for $C_{22}H_{14}Cl_3N_2O_2$ [M−H]⁻, 443.0121; found, 443.0115.

c. N-(5-chloro-4-((4-chlorophenyl)(cyano)methyl)-2-methylphenyl)-2-hydroxy-benzamide (1b)

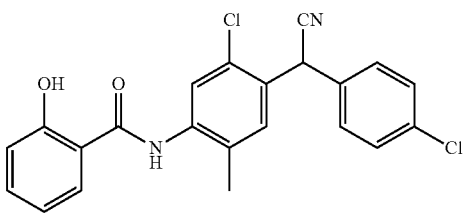

Compound 1b (42.7 mg, 34.6%) was prepared according to the methods described in the synthesis of 1a. ¹H NMR (600 MHz, DMSO-d₆) δ 9.90 (s, 1H), 9.79 (s, 1H), 7.63 (s, 1H), 7.52-7.51 (m, 2H), 7.51-7.50 (m, 1H), 7.43-7.42 (m, 1H), 7.41-7.39 (m, 2H), 7.35 (dd, J=3.7, 1.8 Hz, 1H), 7.33 (d, J=7.8 Hz, 1H), 7.02-6.98 (m, 1H), 6.03 (s, 1H), 2.29 (s, 3H). ¹³C NMR (150 MHz, DMSO-d₆) δ 166.1, 157.9, 138.6, 136.0, 134.3, 133.8, 133.4, 132.0, 130.3, 130.0, 130.0, 129.6, 129.5, 127.6, 119.5, 119.3, 118.7, 115.1, 38.6, 18.0. MS (ESI) m/z: 411 [M+H]⁺. HRMS (ESI) calculated for $C_{22}H_{17}Cl_2N_2O_2$ [M+H]⁺, 411.0662; found, 411.0662.

d. N-(5-chloro-4-((4-chlorophenyl)(cyano)methyl)-2-methylphenyl)-2-mercapto-benzamide (1c)

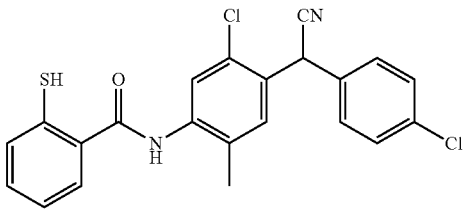 [SMILES: Cc1cc(C(C#N)c2ccc(Cl)cc2)c(Cl)cc1NC(=O)c1ccccc1S]

Compound 1c (20 mg, 31.2%) was prepared according to the methods described in the synthesis of 1a. ¹H NMR (600 MHz, DMSO-d₆) δ 8.10-8.01 (m, 1H), 7.96 (dt, J=7.8, 1.0 Hz, 1H), 7.77 (ddd, J=8.4, 7.2, 1.3 Hz, 1H), 7.69 (s, 2H), 7.54-7.50 (m, 3H), 7.49-7.44 (m, 2H), 6.12 (s, 1H), 2.19 (s, 3H). ¹³C NMR (150 MHz, DMSO-d₆) δ 163.6, 141.4, 137.4, 136.3, 133.7, 133.1, 133.0, 132.4, 132.1, 130.7, 129.7, 129.6, 129.1, 126.1, 125.8, 122.9, 122.0, 118.7, 38.1, 17.1.

MS (ESI) m/z: 427 [M+H]⁺. HRMS (ESI) calculated for $C_{22}H_{15}Cl_2N_2OS$ [M−H]⁻, 425.0282; found, 425.0277.

e. 2-amino-N-(5-chloro-4-((4-chlorophenyl)(cyano)methyl)-2-methylphenyl)-benzamide (1d)

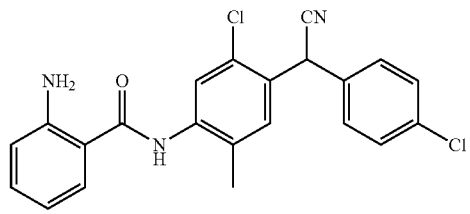

To a stirred solution of 1e (41.0 mg, 0.1 mmol) in acetic acid (1 mL) was added metallic iron powder (16.8 mg, 0.3 mmol) at room temperature. The reaction mixture was heated to 56° C. for 1.5 hours and then cooled to room temperature. The solvent was removed under reduced pressure and extracted with ethyl acetate. The organic layer was washed with brine, dried over anhydrous MgSO₄, and concentrated under reduced pressure. The crude solid was purified by column chromatography on silica gel (dichloromethane/petroleum ether=3/1) to afford 1d as white crystals, with a yield of 20.6 mg, 50.2%. ¹H NMR (600 MHz, DMSO-d₆) δ 9.73 (s, 1H), 7.69 (d, J=7.1 Hz, 1H), 7.61 (s, 1H), 7.52 (s, 1H), 7.51 (d, J=2.4 Hz, 2H), 7.41 (d, J=8.5 Hz, 2H), 7.22 (dd, J=11.2, 4.1 Hz, 1H), 6.77 (d, J=8.3 Hz, 1H), 6.61 (t, J=7.5 Hz, 1H), 6.03 (s, 1H), 2.28 (s, 3H). ¹³C NMR (150 MHz, DMSO-d₆) δ 168.3, 150.4, 138.8, 134.3, 133.8, 133.4, 132.9, 131.9, 130.0, 129.6, 129.5, 129.3, 127.6, 119.6, 117.1, 115.4, 114.7, 110.0, 38.5, 18.0. MS (ESI) m/z: 410 [M+H]⁺. HRMS (ESI) calculated for $C_{22}H_{18}C_2N_3O$ [M+H]⁺, 410.0821; found, 410.0821.

f. N-(5-chloro-4-((4-chlorophenyl)(cyano)methyl)-2-methylphenyl)-2-nitrobenzamide (1e)

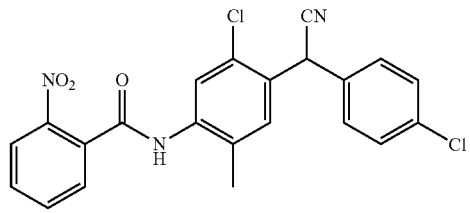 [SMILES: Cc1cc(C(C#N)c2ccc(Cl)cc2)c(Cl)cc1NC(=O)c1ccccc1[N+](=O)[O-]]

Compound 1e (78.5 mg, 59.4%) was prepared according to the methods described in the synthesis of 1a. ¹H NMR (600 MHz, DMSO-d₆) δ 10.33 (s, 1H), 8.19 (d, J=8.1 Hz, 1H), 7.91 (t, J=7.4 Hz, 1H), 7.84 (d, J=7.3 Hz, 1H), 7.78 (s, 1H), 7.74 (s, 1H), 7.52 (d, J=1.2 Hz, 2H), 7.50 (s, 1H), 7.41 (d, J=8.4 Hz, 2H), 6.05 (s, 1H), 2.30 (s, 3H). ¹³C NMR (150 MHz, DMSO-d₆) δ 165.3, 146.8, 137.7, 134.7, 134.2, 133.4, 132.8, 132.7, 132.2, 131.5, 130.3, 130.0, 129.9, 129.7, 129.6, 126.6, 124.8, 119.5, 38.6, 17.8. MS (ESI) m/z: 440[M+H]⁺. HRMS (ESI) calculated for $C_{22}H_{14}Cl_2N_3O_3$ [M−H]⁻, 438.0412; found, 438.0407.

g. 3,5-dichloro-N-(5-chloro-4-((4-chlorophenyl)(cyano)methyl)-2-methylphenyl)-2-hydroxy-benzamide (1f)

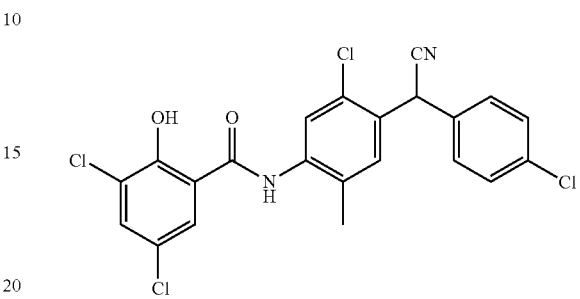

Compound 1f (78.5 mg, 59.4%) was prepared according to the methods described in the synthesis of 1a. ¹H NMR (600 MHz, DMSO-d₆) δ 10.63 (s, 1H), 8.05 (d, J=2.5 Hz, 1H), 7.84 (d, J=2.5 Hz, 1H), 7.76 (d, J=2.7 Hz, 1H), 7.75-7.73 (m, 1H), 7.55 (s, 1H), 7.52-7.48 (m, 2H), 7.43-7.39 (m, 2H), 6.04 (s, 1H), 2.29 (s, 3H). ¹³C NMR (150 MHz, DMSO-d₆) δ 166.0, 136.7, 133.7, 133.1, 133.0, 133.0, 131.6, 130.5, 129.6, 129.3, 129.2, 128.3, 126.9, 126.8, 122.9, 122.5, 119.0, 118.8, 38.1, 17.3. MS (ESI) m/z: 479 [M+H]⁺. HRMS (ESI) calculated for $C_{22}H_{13}Cl_4N_2O_2$ [M−H]⁻, 476.9731; found, 476.9726.

h. N-(5-chloro-4-((4-chlorophenyl)(cyano)methyl)-2-methylphenyl)-5-fluoro-2-hydroxy-benzamide (1g)

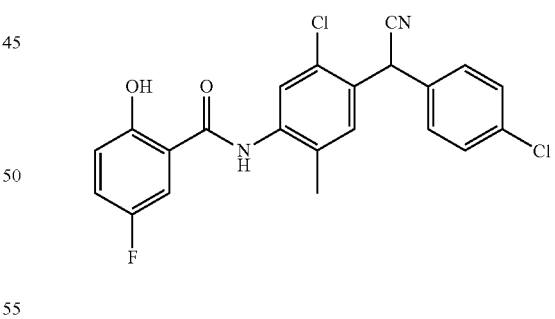

Compound 1g (78.5 mg, 59.4%) was prepared according to the methods described in the synthesis of 1a. ¹H NMR (600 MHz, DMSO-d₆) δ 11.97 (s, 1H), 10.55 (s, 1H), 8.33 (s, 1H), 7.73 (dd, J=9.6, 3.3 Hz, 1H), 7.53-7.50 (m, 2H), 7.50-7.48 (m, 1H), 7.43-7.38 (m, 2H), 7.33 (ddd, J=8.9, 7.8, 3.3 Hz, 1H), 6.01 (s, 1H), 2.34 (s, 3H). MS (ESI) m/z: 429[M+H]⁺. HRMS (ESI) calculated for $C_{22}H_{14}Cl_2FN_2O_2$ [M−H]⁻, 427.0416; found, 427.0411.

i. N-(5-chloro-4-((4-chlorophenyl)(cyano)methyl)-2-methylphenyl)-3-fluoro-2-hydroxy-benzamide (1h)

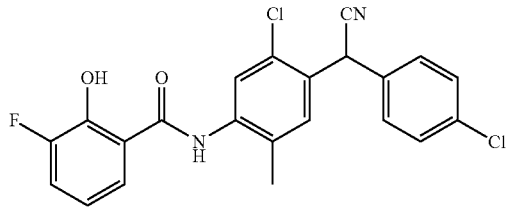 [SMILES: Cc1cc(C(C#N)c2ccc(Cl)cc2)c(Cl)cc1NC(=O)c1cccc(F)c1O]

Compound 1h (78.5 mg, 59.4%) was prepared according to the methods described in the synthesis of 1a. $^1$H NMR (600 MHz, DMSO-$d_6$) δ 12.24 (s, 1H), 10.61 (s, 1H), 8.11 (s, 1H), 7.85 (d, J=8.0 Hz, 1H), 7.53 (s, 1H), 7.52-7.49 (m, 2H), 7.46 (ddd, J=10.8, 8.1, 1.5 Hz, 1H), 7.42-7.39 (m, 2H), 6.99 (td, J=8.1, 4.8 Hz, 1H), 6.03 (s, 1H), 2.33 (s, 3H). MS (ESI) m/z: 429[M+H]$^+$. HRMS (ESI) calculated for $C_{22}H_{14}Cl_2FN_2O_2$ [M–H]$^-$, 427.0416; found, 427.0411.

j. N-(5-chloro-4-((4-chlorophenyl)(cyano)methyl)-2-methylphenyl)-2,3-dihydroxy-benzamide (1i)

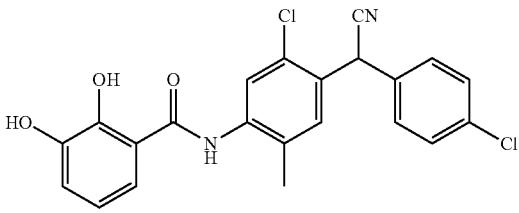 [SMILES: Cc1cc(C(C#N)c2ccc(Cl)cc2)c(Cl)cc1NC(=O)c1cccc(O)c1O]

Compound 1i (78.5 mg, 59.4%) was prepared according to the methods described in the synthesis of 1a. $^1$H NMR (600 MHz, DMSO-$d_6$) δ 11.26 (s, 1H), 10.56 (s, 1H), 9.77 (s, 1H), 8.19 (s, 1H), 7.50 (dd, J=6.7, 4.7 Hz, 3H), 7.46 (dd, J=8.1, 1.5 Hz, 1H), 7.41-7.37 (m, 2H), 7.01 (dd, J=7.8, 1.6 Hz, 1H), 6.86-6.77 (m, 1H), 6.02 (s, 1H), 2.31 (s, 3H). $^{13}$C NMR (150 MHz, DMSO-$d_6$) δ 166.0, 147.0, 146.6, 138.5, 134.3, 133.4, 131.9, 130.1, 130.0, 130.0 129.6, 128.9, 124.1, 120.1, 119.6, 119.6, 119.5, 118.5, 38.5, 17.8. MS (ESI) m/z: 427[M+H]$^+$. HRMS (ESI) calculated for $C_{22}H_{15}Cl_2N_2O_3$ [M–H]$^-$, 425.0460; found, 425.0454.

k. 5-chloro-N-(5-chloro-4-((4-chlorophenyl)(cyano)methyl)-2-methylphenyl)-2-methoxy-benzamide (1j)

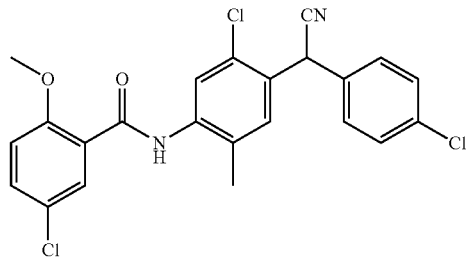 [SMILES: COc1ccc(Cl)cc1C(=O)Nc1cc(Cl)c(C(C#N)c2ccc(Cl)cc2)cc1C]

Compound 1j (78.5 mg, 59.4%) was prepared according to the methods described in the synthesis of 1a. $^1$H NMR (600 MHz, DMSO-$d_6$) δ 10.01 (s, 1H), 8.16 (s, 1H), 7.85 (d, J=2.8 Hz, 1H), 7.63 (dd, J=8.9, 2.8 Hz, 1H), 7.52 (s, 1H), 7.52-7.51 (m, 1H), 7.51-7.49 (m, 1H), 7.40 (d, J=8.5 Hz, 1H), 7.31 (d, J=8.9 Hz, 1H), 6.02 (s, 1H), 4.00 (s, 3H), 2.35 (s, 3H). $^{13}$C NMR (150 MHz, DMSO-$d_6$) δ 162.8, 156.3, 138.3, 134.3, 133.4, 133.1, 131.9, 130.4, 130.0, 130.0, 129.9, 129.6, 129.1, 125.3, 124.5, 123.9, 119.6, 115.1, 57.3, 38.5, 17.6. MS (ESI) m/z: 459 [M+H]$^+$. HRMS (ESI) calculated for $C_{22}H_{15}Cl_2N_2O_3$ [M–H]$^-$, 457.0277; found, 457.0272.

3. General Biology Experimental Methods

Tissue culture reagents were from Life Technologies. P81 phosphocellulose paper was from Whatman and [γ-$^{32}$P]-ATP was from Perkin Elmer. CATCHtide was synthesised by Pepceuticals. Protein G sepharose was from Amersham. DNA constructs used for transfection were purified from *Escherichia coli* DH5a using Qiagen or Invitrogen plasmid Maxi kits according to the manufacturer's protocol. All DNA constructs were verified by DNA sequencing.

a. Plasmids, Protein Expression and Purification

DNA clones were from the Division of Signal Transduction Therapy (University of Dundee). The SPAK proteins were expressed in *E. Coli* and purified as described previously (Zhang et al. (2015) *Human molecular genetics* 24: 4545-4558).

b. SPAK Kinase Assays and IC50 Determination

SPAK kinase assays employing CATCHtide (cation chloride co-transporter peptide substrate). Peptide kinase assays, performed in triplicate, were set up in a total volume of 50 μl containing 0.5 μg GST-[T233E]SPAK kinase (~5 nM at ~10% purity) in 50 mM Tris/HCl, pH 7.5, 0.1 mM EGTA, 10 mM MgCl$_2$, 300 μM CATCHtide (RRHYYYDTHTN-TYYLRTFGHNTRR; SEQ ID NO:1), 0.1 μM [γ-32P]ATP (~500 cpm/pmol) and the indicated concentrations of inhibitor dissolved in DMSO. After incubation for 30 min at 30° C., reactions were terminated by spotting 40 μl of the reaction mix onto P81 phosphocellulose paper and immersion in 50 mM phosphoric acid. The papers were washed extensively and the incorporation of [γ-$^{32}$P]ATP into CATCHtide was quantified by Cerenkov counting. IC$^{50}$ values were calculated with GraphPad Prism using non-linear regression analysis.

c. Fluorescence Polarization

Fluorescence polarization measurements were performed at 25° C. with purified SPAK proteins in 50 mM Tris/HCl, pH 7.5, 150 mM NaCl and 2 mM DTT. The concentration of SPAK proteins was determined by measuring their absorbance at 280 nm and calculated using the molar absorption coefficient determined by the ProtParam Online tool (Gasteiger et al., 2001). All peptides (SEEGKPQLVG RFQVTSSK [EP4543] and SEEGKPQLVGAFQVTSSK [EP4544]; SEQ ID NO:2 and SEQ ID NO:3, respectively) contained an N-terminal linker required for conjugating to the Lumio Green fluorophore (CCPGCCGGGG; SEQ ID NO:4) and were initially re-suspended in 50 mM ammonium bicarbonate, pH 8. Peptide labelling was achieved by incubating 10 nM of each peptide in a 0.5 ml reaction mixture of 20 μM Lumio Green in 25 mM Tris/HCl, pH 7.5, 200 mM NaCl and 5 mM 2-mercaptoethanol. Reactions were left to proceed in the dark for 2 h. The peptides were dialysed for 4 h into 25 mM Tris/HCl, pH 7.5, 200 mM NaCl and 5 mM 2-mercaptoethanol using a Micro DispoDIALYZER with a 100 Da molecular-mass cut-off (Harvard Apparatus), and then for another 12 h with changed buffer. For fluorescence polarization, mixtures were set up containing the indicated concentration of protein, 10 nM Lumio-Green-labelled peptide in a final volume of 30 μl. All individual bindings were performed in duplicate with at least 12 data points per curve. Fluorescence polarization was measured using a BMG PheraStar plate reader, with an excitation wavelength of 485 nm and an emission wavelength of 538 nm, and measurements were corrected to the fluorescent probe alone. Data analysis and graphing were then performed in GraphPad Prism7; a one-site specific binding model was assumed (Y=Bmax*X/[Kd+X]) and the fitted dissociation constant computed. All experimental bindings were repeated at least twice.

d. Pharmacodynamic (PD) Study

Male C57BL/6j wild-type mice (6 weeks old) were purchased from Charles River Laboratories Edinburgh UK. ZT-1a was dissolved in DMSO (Sigma) solution and administered by subcutaneous injection into wild type male C57BL/6 mice at doses of 0, 3, 10, 30, 50 and 100 mg/kg. 50 mg/kg Closantel (1) was injected as a comparative control. Age-matched SPAK$^{502A/502A}$ knock-in mice were also used as comparative controls (Zhang et al. (2015) *Human molecular genetics* 24: 4545-455). Control mice were treated with an equal volume of DMSO solution. One hour after administration, mice were sacrificed by cervical dislocation, and kidney and brain tissues were rapidly dissected and snap-frozen in liquid nitrogen. The SPAK$^{502A/502A}$ knock-in mouse was established and maintained under specific pathogen-free conditions at the University of Dundee (UK) as described in our recent study. Animal experiments and breeding were approved by the University of Dundee ethical committee and performed under a U.K. Home Office project license, in accordance with the Animals (Scientific Procedures) Act 1986, the Policy on the Care, Welfare and Treatment of Animals, and regulations set by the University of Dundee and the U.K. Home Office.

e. Cell Culture, Transfections and Stimulations

HEK293 (human embryonic kidney 293) cells were cultured on 10-cm-diameter dishes in DMEM supplemented with 10% (v/v) foetal bovine serum, 2 mM L-glutamine, 100 U/ml penicillin and 0.1 mg/ml streptomycin. HEK293 cells were transfected with a mixture of 20 µl of 1 mg/ml polyethylenimine (Polysciences) and 5-10 µg of plasmid DNA as described previously (Durocher et al., 2002). 36 hours post-transfection cells were stimulated with either control isotonic or hypotonic medium for a period of 30 minutes. Cells were lysed in 0.3 mL of ice-cold lysis buffer/dish, lysates were clarified by centrifugation at 4° C. for 15 minutes at 26,000 g and the supernatant aliquots were frozen in liquid nitrogen and stored at −20° C. Protein concentrations were determined using the Bradford method. Cells were treated with the indicated concentrations of the SPAK/OSR1 inhibitors. Isotonic buffer was 135 mM NaCl, 5 mM KCl, 0.5 mM CaCl$_2$), 0.5 mM MgCl$_2$, 0.5 mM Na$_2$HPO$_4$, 0.5 mM Na$_2$SO$_4$ and 15 mM HEPES (pH 7.5). Hypotonic low chloride buffer was 67.5 mM sodium-gluconate, 2.5 mM potassium-gluconate, 0.25 mM CaCl$_2$), 0.25 mM MgCl$_2$, 0.5 mM Na$_2$HPO$_4$, 0.5 mM Na$_2$SO$_4$ and 7.5 mM HEPES (pH 7.5).

f. Immunoblotting and Phospho-Antibody Immunoprecipitation

Protein samples (40 µg) were boiled in sample buffer for 5 min, resolved by 7.5% sodium dodecyl sulfate polyacrylamide-gel electrophoresis and electrotransferred onto a polyvinylidene difluoride membrane as previously described (Bhuiyan et al. (2017) *Journal of cerebral blood flow and metabolism: official journal of the International Society of Cerebral Blood Flow and Metabolism* 37: 2780-2794; de Los Heros et al. (2014) *The Biochemical journal* 458: 559-573; Zhu et al. (2014) *Molecular cancer* 13: 31). The membranes were incubated for 30 min with TBST (Tris-buffered saline, 0.05% Tween-20) containing 5% (w/v) skim milk. The blots were then washed six times with TBST and incubated for 1 hour at room temperature with secondary HRP-conjugated antibodies diluted 5000-fold in 5% (w/v) skim milk in TBST. After repeating the washing steps, signals were detected with enhanced chemiluminescence reagent. Immunoblots were developed using a film automatic processor (SRX-101; Konica Minolta Medical) and films were scanned at 600 dpi (PowerLook 1000; UMAX). Figures were generated using Photoshop/Illustrator (Adobe). The densities of bands were measured with ImageJ. For phospho-antibody immunoprecipitation, KCC isoforms were immunoprecipitated from indicated cell extracts. 2 mg of the indicated clarified cell extract were mixed with 15 µg of the indicated phospho-specific KCC antibody conjugated to 15 µl of protein-G-Sepharose, in the added presence of 20 µg of the dephosphorylated form of the phosphopeptide antigen, and incubated 2 hours at 4° C. with gentle shaking. Immunoprecipitates were washed three times with 1 mL of lysis buffer containing 0.15 M NaCl and twice with 1 ml of buffer A. Bound proteins were eluted with 1×LDS sample buffer.

g. $^{86}$Rb$^+$ Uptake Assay in HEK293 Cells

HEK293 cells were plated at 50-60% confluence of in 12-well plates (2.4-cm-diameter per/well) and transfected with wild-type or various mutant forms of full-length flag-tagged human KCCs. Each well of HEK293 cells was transfected with 2.5 µL of 1 mg/mL polyethylenimine and 1 µg of plasmid DNA. The $^{86}$Rb$^+$-uptake assay was performed on cells at 36 hours post-transfection. Culture medium was aspirated from the wells and replaced with either isotonic or hypotonic medium for 15 min at 37° C., then for a further 15 min with stimulating medium containing additional 1 mM ouabain and 0.1 mM bumetamide, to prevent $^{86}$Rb$^+$ uptake via the NKCC1 cotransporter. This stimulating medium was then removed and replaced with isotonic medium plus inhibitors containing 2 µCi/mL $^{86}$Rb$^+$ for 10 min at 37° C., following which cells were rapidly washed three times with the respective ice-cold non-radioactive medium. The cells were lysed in 300 µL of ice-cold lysis buffer and $^{86}$Rb$^+$ uptake was quantitated by liquid scintillation counting (PerkinElmer).

h. Model of Post-Hemorrhagic Hydrocephalus

All animal experiments were approved by the Institutional Animal Care and Use Committee (IACUC) of the Yale University, and in accordance with the guidelines and regulations in the NIH Guide for the Care and Use of Laboratory Animals. Male Wistar rats (Harlan, Indianapolis, Ind., USA), age 8 weeks (220-230 g), were anesthetized (60 mg/kg ketamine plus 7.5 mg/kg xylazine, IP) and allowed to breathe room air spontaneously. Body temperature was maintained at 37±1° C. (Harvard Apparatus, Holliston, Mass., USA) throughout the course of the experiments. PHH was modeled using a modified protocol based on previously described methods (Karimy et al. (2015) *Nature medicine* 23: 997-1003; Simard et al. (2011) *Transl Stroke Res* 2: 227-231). Briefly, in an anesthetized animal, the tail artery was aseptically cannulated using a flexible catheter (PE-20) pre-loaded with heparinized saline. The rat was then mounted in a stereotactic apparatus (Stoelting Co., Wood Dale, Ill.), a midline scalp incision was made to expose the skull and a 1 mm burr hole was made using a high-speed drill over the right lateral ventricle (coordinates, x=−0.8, y=−1.7 mm relative to bregma). Approximately 200 µL of blood was drawn from the tail artery catheter and loaded into a 500 µL syringe (Hamilton, Reno, Nev.), which was mounted to the stereotactic frame. Under stereotactic guidance, 50 µL of freshly collected autologous blood, free from anticoagulants, was infused into the right lateral ventricle (coordinates, x=−0.8, y=−1.7, z=−4.5 mm relative to bregma), over the course of 5 minutes, and the 26-gauge needle is held in place for an additional 20 minutes to prevent backflow of blood upon needle removal.

i. Quantitation of Rates of CSF Production and Intracerebroventricular Drug Administration Rates of CSF production were measured using the method we recently published (Karimy et al. (2015) *Nature medicine* 23: 997-1003). Briefly, anesthetized rats were mounted in a stereotactic apparatus and a 1.3 mm burr hole was made over the left lateral ventricle (coordinates, x=−0.8, y=+1.7 relative to bregma). Over the right lateral ventricle, an Alzet brain infusion cannula (#1; Durect, Cupertino, Calif.) was mounted with one spacer to adjust to −4.5 mm depth. The cannula was then connected to a 1 mL syringe loaded with either ZT-1a or vehicle solution (see below) via PE-20 catheter tubing to a syringe infusion apparatus (Pump elite 11; Harvard Apparatus). Next, the rat's head was rotated on the ear-bars 90°, nose-down, and the suboccipital muscles were dissected to the cisterna magna to expose the atlantooccipital ligament. The ligament is punctured and a 23-gauge flexible catheter (PE-20) was advanced 5 mm through the foramen of Magendie to the 4th ventricle. Sterile, molecular grade mineral oil (100 µL; Sigma Aldrich, St. Louis, Mo.) was infused into the 4th ventricle to occlude the aqueduct of Slyvius, thereby creating a closed system of CSF circulation. With the rat in the same position, a glass capillary tube (cat # CV8010-300; borosilicate; OD, 1 mm; ID, 0.8 mm; length, 30 cm; VitroCom, Mountain Lakes, N.J.) is advanced through the burr hole into the left lateral ventricle. The volume (V) of CSF that forms at a given timepoint is calculated as: $V (mm^3) = \pi \cdot r^2 \cdot d$, where r is the radius of the capillary tube and d is the distance CSF traveled within the capillary. The rate of CSF formation (µL/min) can be calculated from the slope of the volume-time relationship. A baseline rate of spontaneous CSF secretion (no drug infusion) was calculated over 30 minutes prior to drug infusion, then compared to the calculated rate of CSF formation following 30 minutes of ZT-1a infusion.

ZT-1a solution preparation. Intraventricular infusion solutions were made using sterile artificial cerebrospinal fluid (aCSF), composed as follows (in mM): sodium, 150; potassium, 3.0; calcium, 1.4; magnesium, 0.8; phosphorus, 1.0; chlorine, 155, pH 7.19 (Tocris, Bristol, UK), with a calculated osmolarity of 311.2 mOsmC/l (Karimy et al., 2015; Karimy et al., 2017). ZT-1a was dissolved in CSF using DMSO as a co-solvent and titrated to pH 9 (10 mmol, 1% DMSO, pH 9). As a control, a vehicle solution of aCSF (1% DMSO, pH 9) omitting ZT-1a was prepared and tested.

j. Tissue Harvest and Choroid Plexus Isolation.

Rats were euthanized via overdose of pentobarbital (Euthasol) administered IP and transcardially perfused with ice-cold normal saline. The brain was rapidly isolated and then placed in an ice-cold saline bath, after which the choroid plexus was carefully dissected under magnification using sharp forceps. Approximately 3 mg of choroid plexus tissue was harvested from each brain, which was then collected into a 1.5 mL tube and flash frozen in liquid nitrogen for storage.

k. Middle Cerebral Artery Occlusion Model

Focal cerebral ischemia was induced by transient occlusion of the left middle cerebral artery (MCA) for 50 min as described previously (Bhuiyan et al. (2017) Journal of cerebral blood flow and metabolism: official journal of the International Society of Cerebral Blood Flow and Metabolism 37: 2780-2794; Zhao et al. (2017) Journal of cerebral blood flow and metabolism: official journal of the International Society of Cerebral Blood Flow and Metabolism 37: 550-563). Under an operating microscope, the left common carotid artery was exposed through a midline incision. Two branches of the external carotid artery (ECA), occipital and superior thyroid arteries, were isolated and coagulated. The ECA was dissected further distally and permanently ligated. The internal carotid artery (ICA) was isolated and carefully separated from the adjacent vagus nerve. A 12 mm length of silicon-coated nylon filament (size 6-0, native diameter 0.11 mm; diameter with coating 0.21+/−0.02 mm; coating length 5-6 mm; Doccol Corporation, Sharon, Mass.) was introduced into the ECA lumen through a puncture. The silk suture around the ECA stump was tightened around the intraluminal nylon suture to prevent bleeding. The nylon suture was then gently advanced from the ECA to the ICA lumen until mild resistance was felt (~9 mm). For reperfusion, the suture was withdrawn 50 min after MCAO to restore blood flow. Body temperature was maintained for the duration of the experiment between 36.5° C.-37° C. with a small animal heating pad (Kent Scientific).

l. Cerebral Blood Flow Measurement

Cerebral blood flow was measured using a two-dimensional laser speckle contrast analysis system (PeriCam PSI High Resolution with PIMSoft, Perimed) (Begum et al. (2017) Glia, DOI: 10.1002/glia.23232; Chung-Yang Yeh (2017) *J Neurosci* 37: 5648-5658). Isoflurand-anesthetized mice were head-fixed using stereotaxic equipment during imaging. The skin was retracted to expose the intact skull. Images were taken at 19 frames/second with averaging. Average signal intensity was taken from a fixed size (0.5 $mm^2$) regions of interest drawn over the parietal bone plate on the ipsi- and contra-lateral sides. Percent perfusion values were taken in comparison to the mean values of the pre-ischemic ipsilateral side. Five consecutive images at each time period per animal were averaged for analysis.

m. Brain Infarction Volume and Hemispheric Swelling Measurements

At 24 hours reperfusion, mice were anesthetized with 5% isoflurane and then decapitated. Coronal brain tissue slices (2 mm) were stained for 20 minutes at 37° C. with 1% 2,3,5-triphenyltetrazolium chloride monohydrate (TTC; Sigma, St Louis, Mo.) in PBS solution. Infarction volume was calculated with correction for edema using ImageJ software as described (Swanson et al. (1990) *Journal of cerebral blood flow and metabolism: official journal of the International Society of Cerebral Blood Flow and Metabolism* 10: 290-293). The extent of hemispheric swelling was calculated using the following equation: swelling (% contralateral side)=[(volume of ipsilateral hemisphere-volume of contralateral hemisphere)/volume of contralateral hemisphere]×100 (Bhuiyan et al. (2017) *Journal of cerebral blood flow and metabolism: official journal of the International Society of Cerebral Blood Flow and Metabolism* 37: 2780-2794).

n. Neurological Deficit Score

A neurological deficit grading system (Bhuiyan et al. (2017) Journal of cerebral blood flow and metabolism: official journal of the International Society of Cerebral Blood Flow and Metabolism 37: 2780-2794; Zhao et al. (2017) Journal of cerebral blood flow and metabolism: official journal of the International Society of Cerebral Blood Flow and Metabolism 37: 550-563) was used to evaluate neurological deficit at 0, 1, 3, 5, and 7 days after tMCAO. The scores were: 0, no observable deficit; 1, forelimb flexion; 2, forelimb flexion and decreased resistance to lateral push; 3, forelimb flexion, decreased resistance to lateral push, and unilateral circling; 4, forelimb flexion and partial or complete lack of ambulation.

o. Corner Test

Corner test was used to assess MCAO-induced sensorimotor abnormalities as described previously (Zhao et al. (2017) *Journal of cerebral blood flow and metabolism: official journal of the International Society of Cerebral Blood Flow and Metabolism* 37: 550-563). In brief, the corner test apparatus consists of two cardboards (30×20×1 cm each) placed together at a 30° angle to form a narrow alley. The mouse was placed between the two angled boards facing the corner. When exiting the corner, uninjured mice turned left or right randomly. After tMCAO, animals with unilateral brain damage displayed an asymmetry in corner turning. The numbers of left and right turns of each mouse during 10 trials were recorded, and turning movements that were not part of a rearing movement were not scored. Preoperative training was carried twice per day for three days prior to operation. Postoperatively, animals were tested on day 1, 3, 5, and 7.

p. Adhesive Removal Test

An adhesive removal test was used to measure somatosensory deficits as described previously (Begum et al. (2017) Glia, DOI: 10.1002/glia.23232; Zhao et al. (2017) *Journal of cerebral blood flow and metabolism: official journal of the International Society of Cerebral Blood Flow and Metabolism* 37: 550-563). In brief, two small pieces of adhesive tape (4 mm×3 mm) were attached to the forepaws in an alternating sequence and with equal pressure by the experimenter before each trial. Animals were released into a testing cage, and the time of contact and removal of the adhesive patch were recorded. Contact was recorded when either shaking of the paw or mouth contact occurred. The trial ended after the adhesive patch was removed or after 2 min had elapsed. Preoperative training was carried twice per day for three days prior to operation. Postoperatively, animals were tested on day 1, 3, 5, and 7.

q. DTI of Ex-Vivo Brains

Seven days post-reperfusion, mice were anesthetized with 5% isoflurane, transcardially perfused with 4% paraformaldehyde (PFA) and decapitated (Zhao et al. (2017) *Journal of cerebral blood flow and metabolism: official journal of the International Society of Cerebral Blood Flow and Metabolism* 37: 550-563). For ex-vivo MRI, brains were maintained within the skull to avoid anatomical deformation. After overnight post-fixation in 4% PFA, heads were stored in PBS solution at 4° C. MRI was performed at 500 MHz using a Bruker AV3HD 11.7 T/89 mm vertical bore small animal MRI scanner, equipped with a 25-mm quadrature RF coil and Paravision 6.0 (Bruker Biospin, Billerica, Mass.). Following positioning and pilot scans, a DTI data set covering the entire brain was collected using a multislice spin echo sequence with 3 reference and 30 noncollinear diffusion-weighted images with the following parameters: TE/TR=22/5000 ms, 4 averages, matrix size=192×192 reconstructed to 256×256, field of view=17.3×17.3 mm, 33 axial slices, slice thickness=0.5 mm, b-value=1200 s/mm2, and $\Delta/\delta$=10/5 ms.

DTI data were analyzed with DSI Studio (Zhao et al. (2017) Journal of cerebral blood flow and metabolism: official journal of the International Society of Cerebral Blood Flow and Metabolism 37: 550-563). In a blinded manner, region of interests (ROIs) were manually drawn for the ipsilateral (IL) and contralateral (CL) cortex, striatum, corpus callosum (CC), and external capsule (EC). Values for the fractional anisotropy (FA), afferent diffusion coefficient (ADC), and diffusivity were calculated for the entire volume of each ROI.

r. Preparation of Brain Membrane and Cytosolic Protein Fractions

Brain homogenates were prepared as previously described (Bhuiyan et al. (2017) Journal of cerebral blood flow and metabolism: official journal of the International Society of Cerebral Blood Flow and Metabolism 37: 2780-2794). Mice were anesthetized with 5% isoflurane vaporized in $N_2O$ and $O_2$ (3:2), then decapitated. The contralateral (CL) and ipsilateral (IL) brain tissues were dissected in five volumes of cold homogenization buffer (0.25 M sucrose, 10 mM Tris-HCl, 1 mM EDTA, pH 7.4, protease and phosphatase inhibitor cocktail (Pierce). Brain tissues were gently homogenized with a tissue grinder (Kontes, Vineland, N J, USA) for 10 strokes in homogenization buffer. The homogenized samples were centrifuged at 1000×g at 4° C. for 10 min. The supernatant (S1) was collected and centrifuged at ~200,000×g for 30 min in a Beckman Optima™ XL-80k Ultracentrifuge. The cytosolic fraction [supernatant (S2)] and crude membrane pellet were collected. The pellet was re-suspended in the homogenization buffer. Protein content in both membrane and cytosolic fractions was determined by the standard bicinchoninic acid method.

s. Animal Preparation

All animal experiments were approved by the University of Pittsburgh Institutional Animal Care and Use Committee and performed in accordance with the National Institutes of Health Guide for the Care and Use of Laboratory Animals. The manuscript adheres to the ARRIVE guidelines for reporting animal experiments. Eleven to 16-week old C57BL/6J mice (both male and female) were used in the study (Jackson laboratories, Bar Harbor, Me.).

t. Focal Ischemic Stroke and Reperfusion with Transient Middle Cerebral Artery Occlusion Focal ischemic stroke was induced by transient occlusion of the left middle cerebral artery (MCA) for 50 min in normotensive mice as described previously (Huang et al. (2019) *Stroke*. 50:1021-1025). Under an operating microscope, the left common carotid artery was exposed through a midline incision. Two branches of the external carotid artery (ECA), occipital and superior thyroid arteries, were isolated and coagulated. The ECA was dissected further distally and permanently ligated. The internal carotid artery (ICA) was isolated and carefully separated from the adjacent vagus nerve. A 12 mm length of silicon-coated nylon filament (size 6-0, native diameter 0.11 mm; diameter with coating 0.21+/−0.02 mm; coating length 5-6 mm; Doccol Corporation, Sharon, Mass.) was introduced into the ECA lumen through a puncture. The silk suture around the ECA stump was tightened around the intraluminal nylon suture to prevent bleeding. The nylon suture was then gently advanced from the ECA to the ICA lumen until mild resistance was felt (~9 mm). For reperfusion, the suture was withdrawn 50 min after MCAO to restore blood flow. Body temperature was maintained for the duration of the experiment between 36.5° C.-37° C. with a small animal heating pad (Kent Scientific).

u. ZT-1a Pharmacokinetic (PK) Properties in Sham Control and tMCAO Ischemic Stroke Normotensive Mice ZT-1a content in brain homogenates and plasma was assayed at the University of Pittsburgh Small Molecule Biomarker Core, using liquid chromatography-tandem mass spectrometry (LC-MS/MS). C57BL/6j mice (normotensive male, 11 weeks old) at 3 hr post Sham surgery or tMCAO were intraperitoneally injected with 5 mg/kg ZT-1a. At 2 hr post injection, blood was collected into heparin-treated EP tubes by a cardiac puncture. After a brief cardiac perfusion with ice-cold normal saline, brain tissues (contralateral and ipsilateral hemispheres) were collected. Plasma samples were prepared by centrifugation of whole blood for 10 min at 1,500 g using a refrigerated centrifuge. Brain tissues and plasma samples were diluted, and protein was precipitated with acetonitrile prior to detection of ZT-1a with a triple quad mass spectrometer. Glyburide was used as the internal standard. Samples were then injected by autosampler and ZT-1a was eluted from a Waters Acquity UPLC BEH C18, 1.7 um, 2.1×100 mm reversed-phase column with a water (with 0.1% formic acid) and acetonitrile (with 0.1% formic acid) gradient. Detection and quantitation of ZT-1a were achieved in the positive mode with a Thermo Fisher TSQ Quantum Ultra mass spectrometer interfaced via an electrospray ionization (ESI) probe with the Water UPLC Acquity solvent delivery system.

v. Ang II-Mediated Hypertension (HTN) and BP Measurement

C57BL/6J mice received subcutaneous (s.c.) infusion of either saline or AngII via osmotic minipumps (model 1004, Alzet) at a rate of 1000 ng/kg/min for 14 days. BP was measured in awake mice by a tail-cuff method (Kent Scientific) as described previously (Huang et al. (2019) *Stroke*. 50:1021-1025).

w. Focal Cerebral Ischemia with Permanent Middle Cerebral Artery Occlusion

Saline-infused control and Ang II-mediated HTN mice were subsequently underwent permanent occlusion of the distal branches of the middle cerebral artery (pdMCAO) as described previously (Huang et al. (2019) *Stroke*. 50:1021-1025). Under isoflurane anesthesia, a skin incision at the midline of the neck was made and the left CCA was exposed and occluded by ligation and the skin was sutured. Another skin incision (1 cm) was made between the left eye and the ear using fine operation scissors. The temporal muscle was identified and detached from the skull in its apical and dorsal part without totally removing the muscle by the forceps. The MCA below the transparent skull in the rostral part of the temporal area, dorsal to the retro-orbital sinus was identified. If the MCA bifurcation was not visible (due to an anatomical normal variation), the most rostral vessel was identified. The skull above the MCA branch was thinned out with the drill until it had a thin and translucent texture. The artery, proximal and distal to the MCA bifurcation, was coagulated with the electrocoagulation forceps (in a bipolar mode at 7 W). The temporal muscle was relocated to its position and the burr hole was covered with wax and the skin wound was sutured and infiltrated with analgesia bupivacaine (100 μl 0.25%) topically. The animal was placed in a cage and monitored for recovery from anesthesia. Body temperature was maintained for the duration of the experiment between 36.5-37° C. with a small animal heating pad (Kent Scientific). Sham-operated AngII-mediated hypertensive mice underwent identical surgical procedures but were not subjected to vessel coagulation.

x. Drug Treatment in HTN Mice

Ang II-mediated HTN mice were randomly assigned to receive either vehicle (Veh, 100% DMSO, 2 ml/kg body weight/day) or ZT-1a (5.0 mg/kg body weight/day), administered via intraperitoneal injection (i.p.) with an initial half dose at 3-hours and the second half dose at 8-hours reperfusion.

y. Brain Infarction Volume and Hemispheric Swelling Measurements in HTN Mice

Cerebral infarction and hemisphere swelling were assessed at 24 hours reperfusion as described previously (Swanson etmal. (1990) *J Cereb Blood Flow Metab*. 10:290-293; Bhuiyan et al. (2017) *J Cereb Blood Flow Metab*. 37:2780-2794).

z. Neurological Function Tests in HTN Mice

Foot fault, cylinder test, and adhesive tape removal tests were used to assess pdMCAO-induced somatosensory and motor deficits in HTN mice in a blinded manner as described previously (Bhuiyan et al. (2017) *J Cereb Blood Flow Metab*. 37:2780-2794; Begum et al. (2018) *Glia*. 66).

aa. Statistical Analysis

Animal subjects were randomly assigned into different studies and surgical procedures, and data analyses were performed by investigators blinded to experimental conditions. The number of animals studied was 80% powered to detect 20% changes with α (2-sided)=0.05. Data were expressed as mean±SEM. Statistical significance was determined by student's t-test, or one-way ANOVA using the Tukey's post-hoc test in case of multiple comparisons (GraphPad Prism 6.0, San Diego, Calif., USA). Neurological deficit score was analyzed by the non-parametric Mann-Whitney test. A probability value <0.05 was considered statistically significant.

4. Restoration of Brain Water Homeostasis and Neurological Function Via a Novel Kinase-Cotransporter Modulator a. Identification of ZT-1a: A Novel and Potent Non-ATP-Competitive SPAK Inhibitor.

To identify pharmacological modulators of SPAK kinase, a new focused chemical library derived from the previously identified SPAK inhibitors Closantel (Kikuchi et al. (2015) Journal of the American Society of Nephrology: JASN 26, 1525-1536), Rafoxanide (Alamri et al. (2017) ChemMedChem 12, 639-645), and STOCK1S-14279 (Kikuchi et al. (2015) Journal of the American Society of Nephrology: JASN 26, 1525-1536) was designed and synthesized (FIG. 1A). This "scaffold-hybrid" strategy has proven useful for the successful development of kinase inhibitors with high selectivity (Deng et al. (2011) Nature chemical biology 7, 203-205; Deng et al. (2013) Eur J Med Chem 70, 758-767). Closantel and Rafoxanide target the allosteric site on the C-terminal domains of SPAK and OSR1, rather than the highly-conserved ATP-binding pocket of kinases, thereby inhibiting kinase activity in a non-ATP competitive manner (Alamri et al. (2017) ChemMedChem 12, 639-645)). Iterative rounds of medicinal chemistry optimization led to identification of "ZT-1a" [5-chloro-N-(5-chloro-4-((4-chlorophenyl)(cyano)methyl)-2-methylphenyl)-2-hydroxybenzamide] as a highly selective SPAK inhibitor (Table 1 and FIG. 1A).

Referring to FIG. 1A, a representative hybrid design strategy for WNK pathway inhibitors is shown.

TABLE 1

[Core structure: substituted benzoic acid unit (R, X) connected via C(=O)-NH to a phenyl ring bearing Cl, CH(CN)(4-chlorophenyl), and methyl substituents]

| Compound ID | Substituted benzoic acid unit | SPAK pSer373 (μM) Iso, hypo | NKCC1 pThr203 (μM) Iso, hypo | KCC2 pThr906 (μM) Iso, hypo | KCC2 pThr1007 (μM) Iso, hypo |
|---|---|---|---|---|---|
| 1a (ZT-1a) | 2-OH, 5-Cl phenyl ketone | 1, 3 | 1, 1 | 3, 3 | 1, 3 |
| 1b | 2-OH phenyl ketone | 3, 3 | 3, 1 | 10, 10 | 3, 3 |
| 1c | 2-SH phenyl ketone | 3, 3 | 1, 3 | 10, 10 | 3, 3 |
| 1d | 2-NH$_2$ phenyl ketone | 3, 3 | 1, 3 | 10, 10 | 3, 3 |
| 1e | 2-NO$_2$ phenyl ketone | — | — | — | — |
| 1f | 3,5-diCl, 2-OH phenyl ketone | 3, 3 | 1, 3 | 10, 10 | 3, 3 |
| 1g | 2-OH, 5-F phenyl ketone | 3, 3 | 1, 3 | 10, 10 | 3, 3 |

TABLE 1-continued

| Compound ID | Substituted benzoic acid unit | SPAK pSer373 (μM) Iso, hypo | NKCC1 pThr203 (μM) Iso, hypo | KCC2 pThr906 (μM) Iso, hypo | KCC2 pThr1007 (μM) Iso, hypo |
|---|---|---|---|---|---|
| 1h | F-substituted 2-hydroxyphenyl ketone | 3, 3 | 1, 3 | 10, 10 | 3, 3 |
| 1i | HO-substituted 2-hydroxyphenyl ketone | — | — | — | — |
| 1j | MeO, Cl-substituted phenyl ketone | — | — | — | — |

"—" showed no inhibition of phosphorylation of SPAK/NKCC1/KC22

Figure 1B:
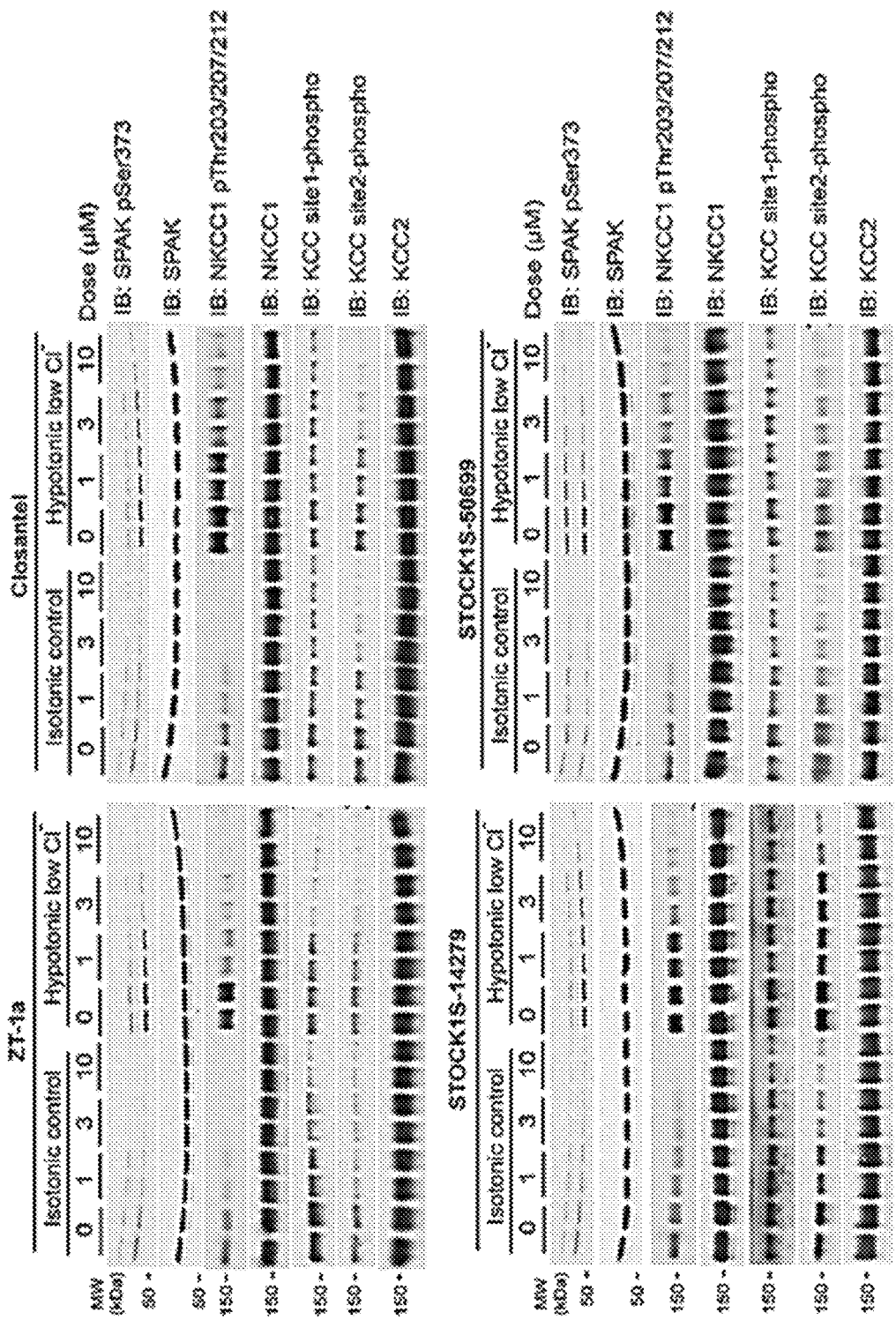
FIG. 1B shows representative data illustrating that ZT-1a does-dependently inhibits KCC2 Thr906/Thr007 phosphorylation in cells.
Figure 2:
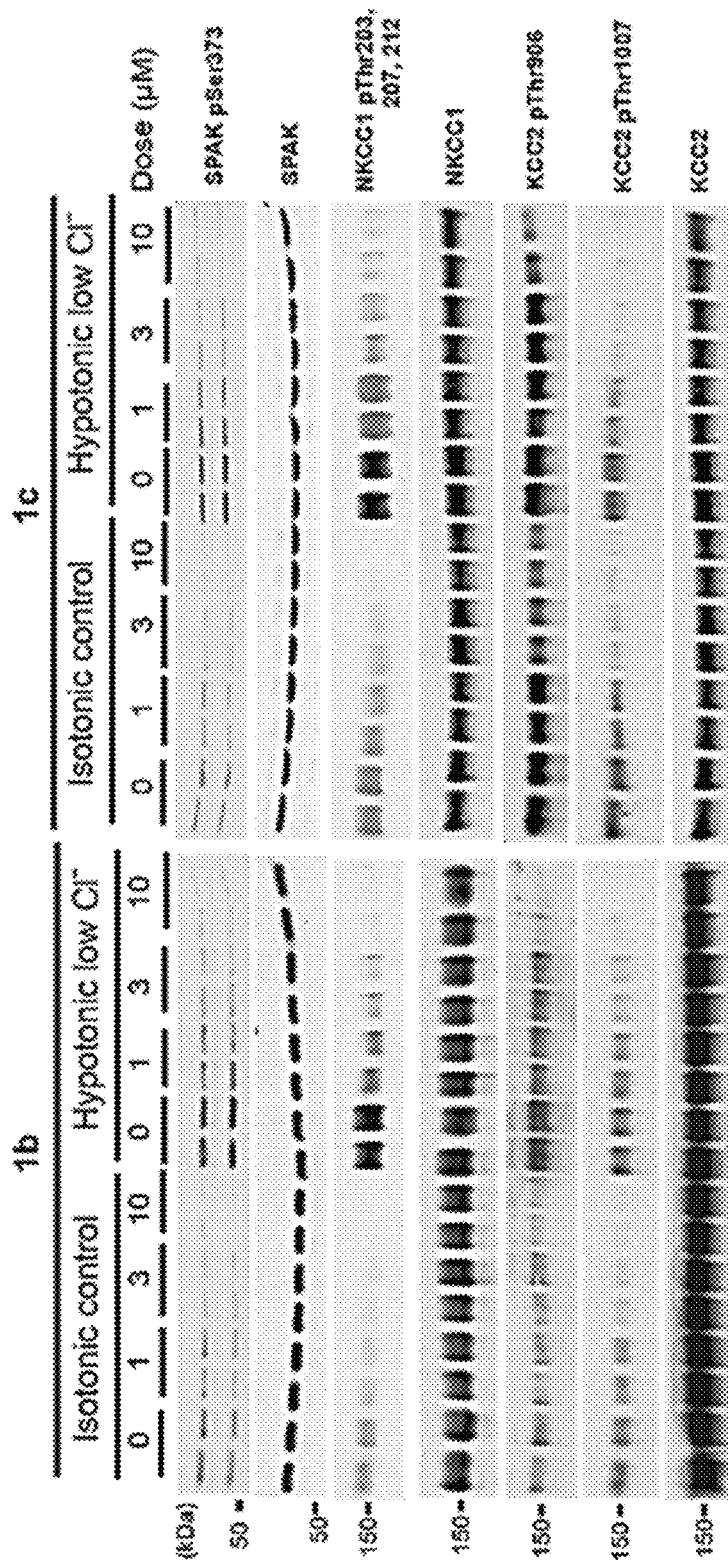
FIG. 2 shows representative concentration-response experiments testing the effects of Closantel analogs on phosphorylation of KCC2 Thr906/Thr1007.
Figure 2:
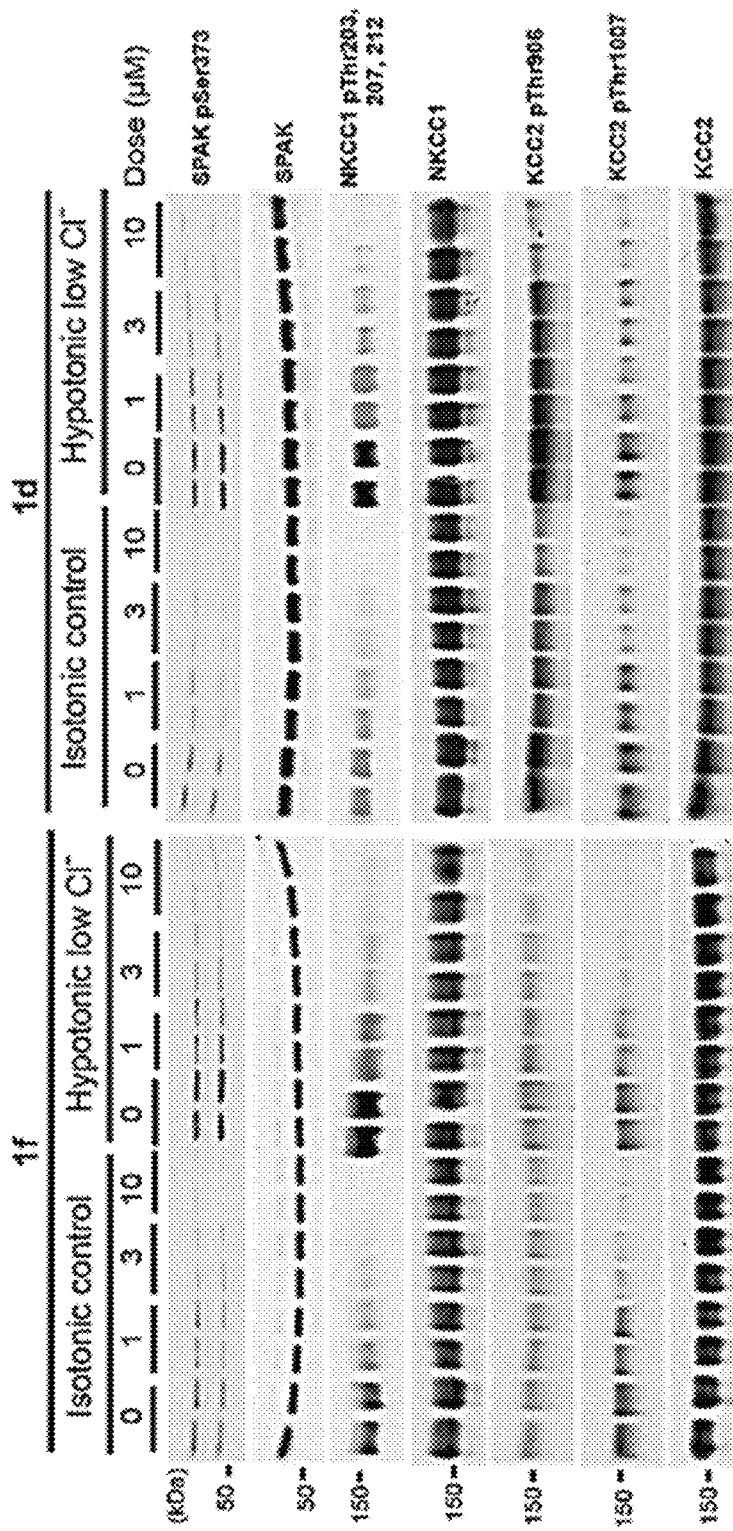
Figure 2:
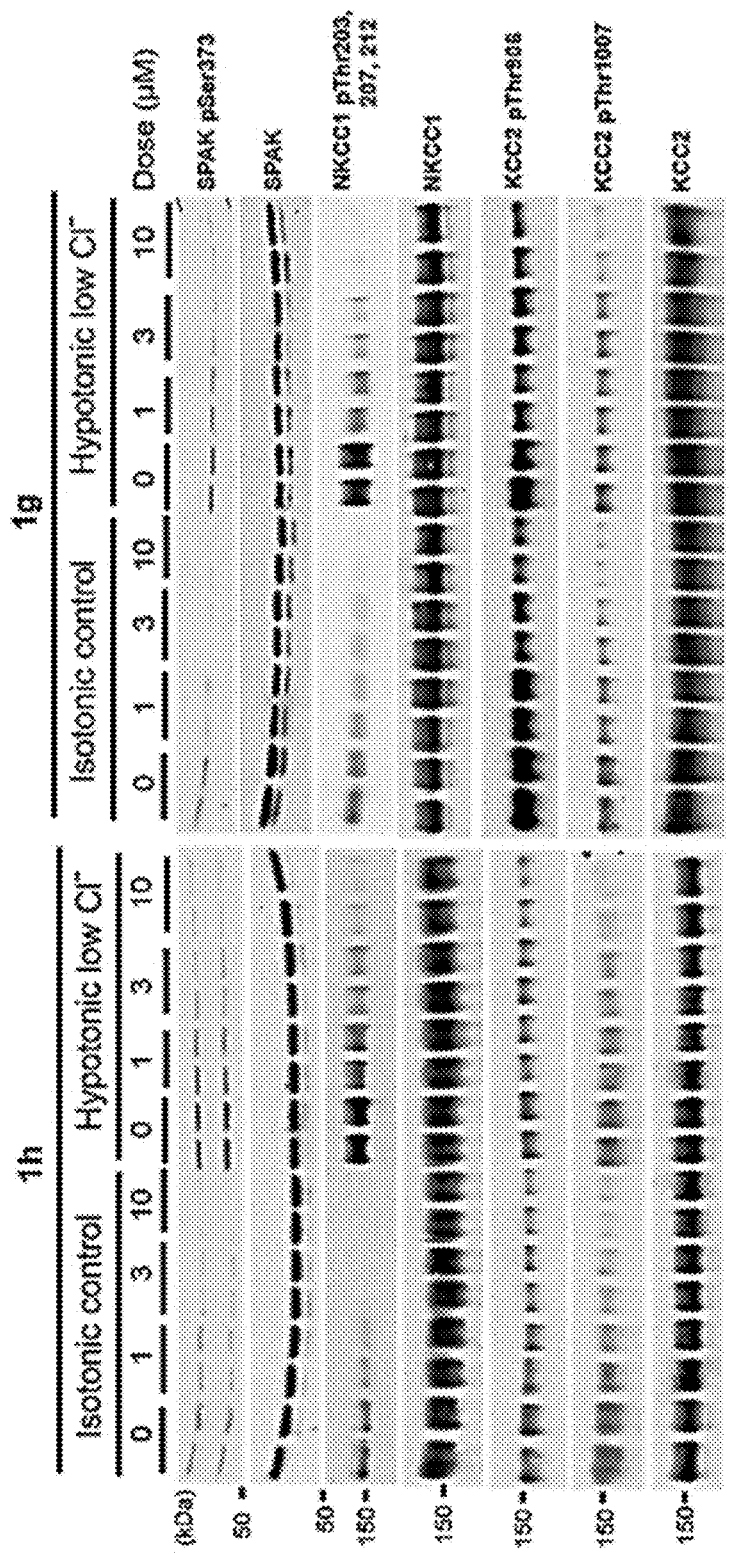
Figure 3:
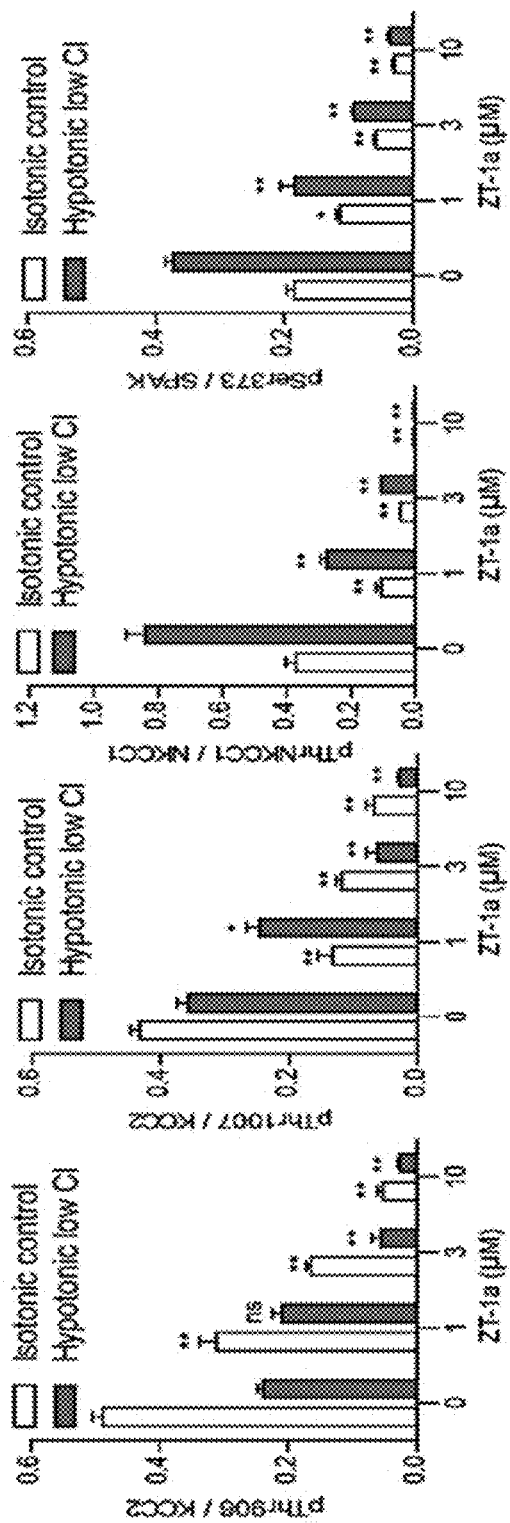
FIG. 3 shows representative data illustrating that ZT-1a dose-dependently inhibited KCC2 Thr906/Thr007 phosphorylation in cells.
Figure 3:
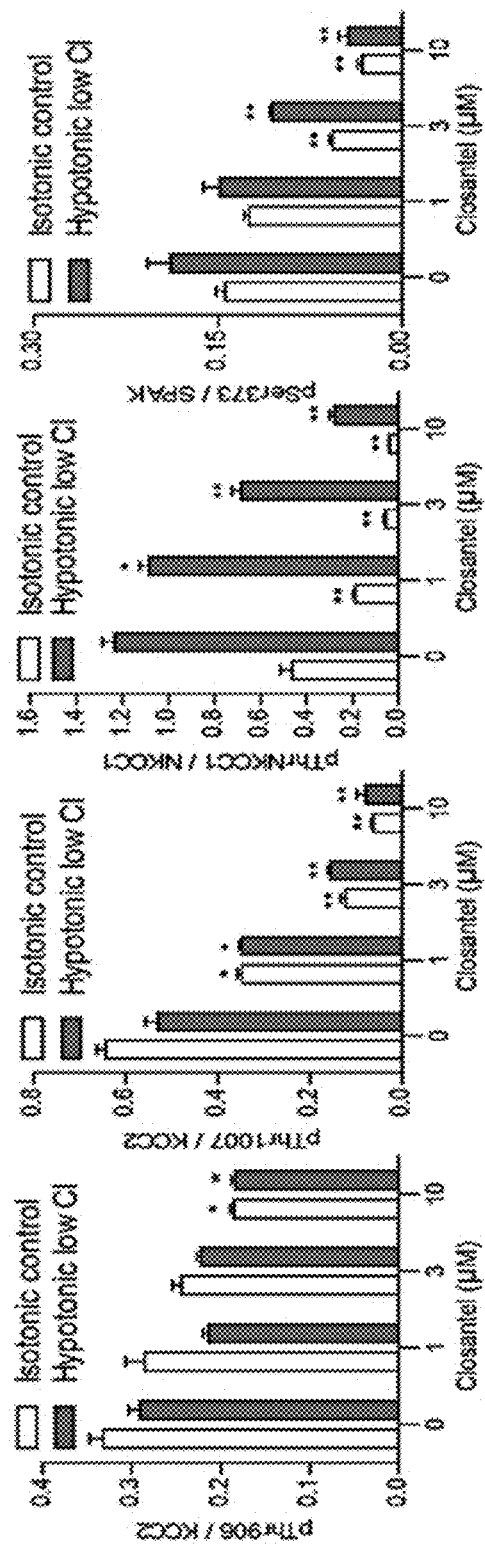
Figure 3:
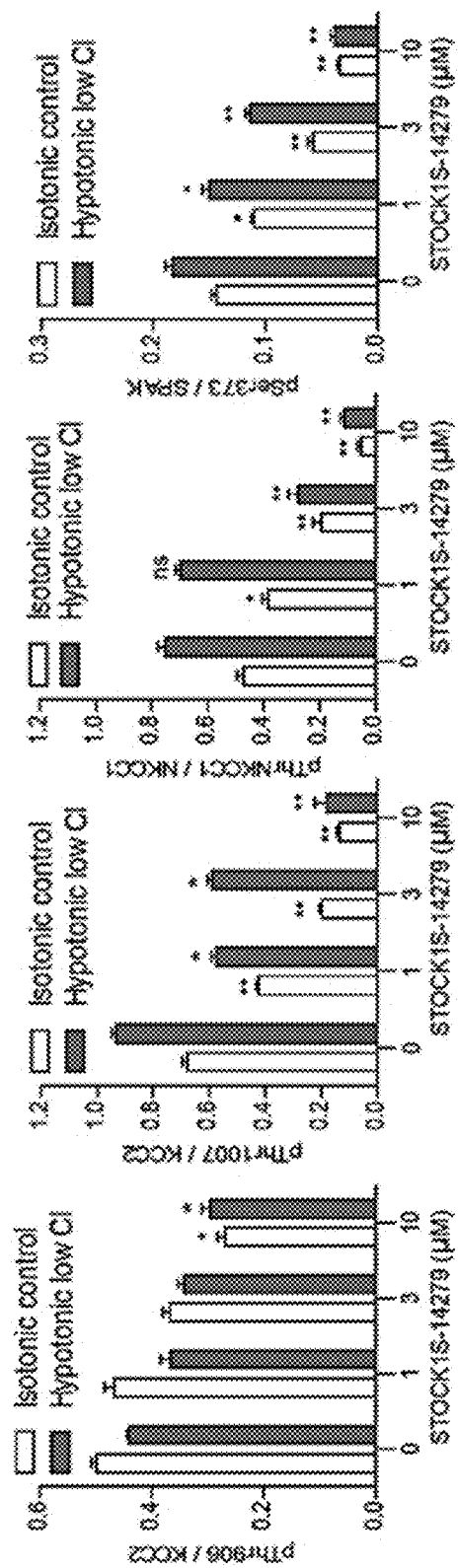
Figure 3:
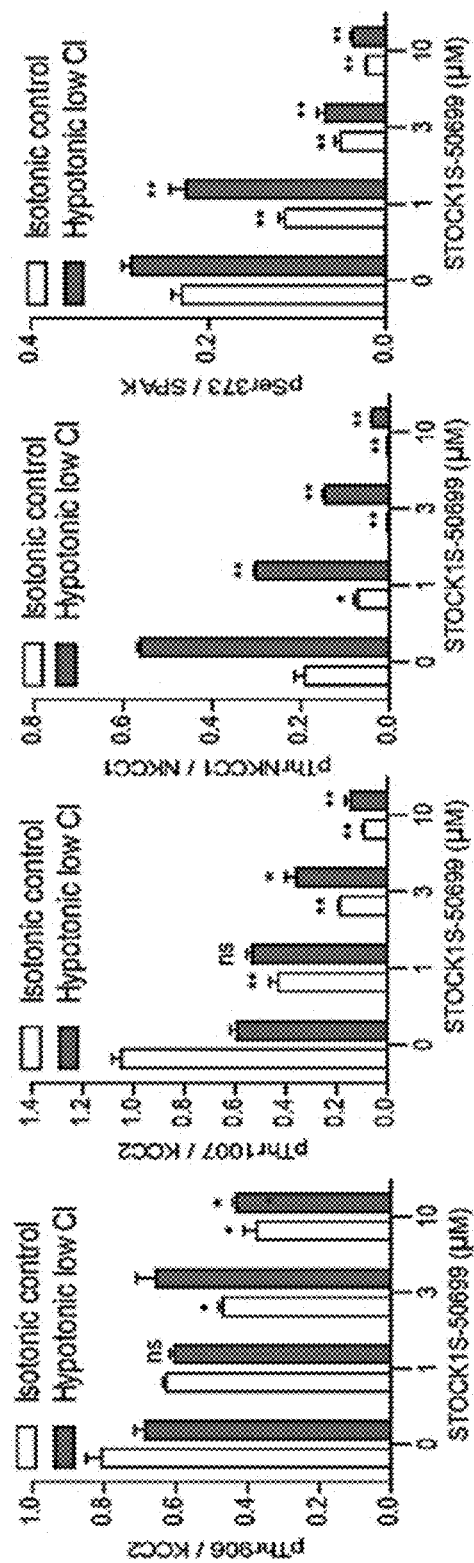

The highest potency salicylic amides selected from the library were compared with Closantel, STOCK1S-14279, and STOCK1S-50699 as SPAK inhibitors in a cellular context. NKCC1 and KCCs (KCC1-4) are phospho-substrates of SPAK kinase (de Los Heros et al. (2014) The Biochemical journal 458, 559-573; Zhang et al. (2016) Scientific reports 6, 35986). SPAK activity was monitored as NKCC1 Thr203/207/212 phosphorylation, required for cotransporter activation (Vitari et al. (2005) The Biochemical journal 391, 17-24), and KCCs sites-1/2 (KCC2 Thr906/1007 or KCC3 Thr991/1048) phosphorylation, required for cotransporter inhibition (de Los Heros et al. (2014) The Biochemical journal 458, 559-573; Rinehart et al. (2009) Cell 138, 525-536) (FIG. 1B, FIG. 2, and FIG. 3). ZT-1a emerged as the most potent compound, exhibiting dose-dependent inhibition of NKCC1 p-Thr203/207/212 (up to 72±5.2% inhibition at 1 μM; $p<0.01$; n=4) and KCCs sites-1/2 phosphorylation (up to 65-77% inhibition at 3 μM; $p<0.01$; n=4) in HEK293 cells (Table 1). Substantial dephosphorylation of SPAK Ser373 was also observed at approximately 3-10 μM concentrations (representing 70±3.8% inhibition; $p<0.01$; n=3; FIG. 1B). Without wishing to be bound by theory, these results confirm ZT-1a as a potent modulator of SPAK-dependent CCC phosphorylation, in contrast to the existing SPAK kinase inhibitors Closantel, STOCK1S-50699 and STOCK S-14279, which only at 10 μM significantly inhibited phosphorylation of KCCs site-1.

Referring to FIG. 1B, ZT-1a dose-dependently inhibited KCC2 Thr906/Thr1007 phosphorylation in cells. HEK293 cells were transfected with a DNA construct encoding wild type N-terminally FLAG-tagged KCC2. 36 hrs post-transfection, cells were exposed 30 min to either control isotonic or hypotonic low [Cl$^-$] conditions, then treated in the same conditions for an additional 30 min with the indicated inhibitors at the concentrations noted. Cell lysates were subjected to SDS-PAGE and Western blotting with the indicated antibodies. See FIG. 3 for Western blot quantitation.

Referring to FIG. 2, concentration-response experiments testing effects of Closantel analogs on phosphorylation of KCC2 Thr906/Thr1007 are shown. HEK293 cells were transfected with DNA construct encoding wild type N-terminally FLAG-tagged KCC2. 36 h post-transfection, cells were exposed 30 min to either control isotonic conditions or hypotonic low Cl$^-$ conditions, then treated in the same conditions with the specified inhibitors (1b, 1c, 1f, 1d, 1h, and 1g, respectively) at the indicated concentrations for an additional 30 min. Lysates were subjected to SDS-PAGE and Western blotting with the indicated antibodies.

Referring to FIG. 3, HEK293 cells were transfected with the DNA construct encoding wild type N-terminally FLAG-tagged KCC2. 36 h post-transfection, cells were exposed 30 min to either control isotonic or hypotonic low Cl$^-$ conditions, then treated in the same conditions with the specified inhibitors at the indicated concen-trations for an additional 30 min. Lysates were subjected to SDS-PAGE and Western blotting with the indicated antibodies. Closantel, STOCK1S-14279 and STOCK1S-50699 were used as reference compounds. See FIG. 1B for Western blots.

Figure 4A:
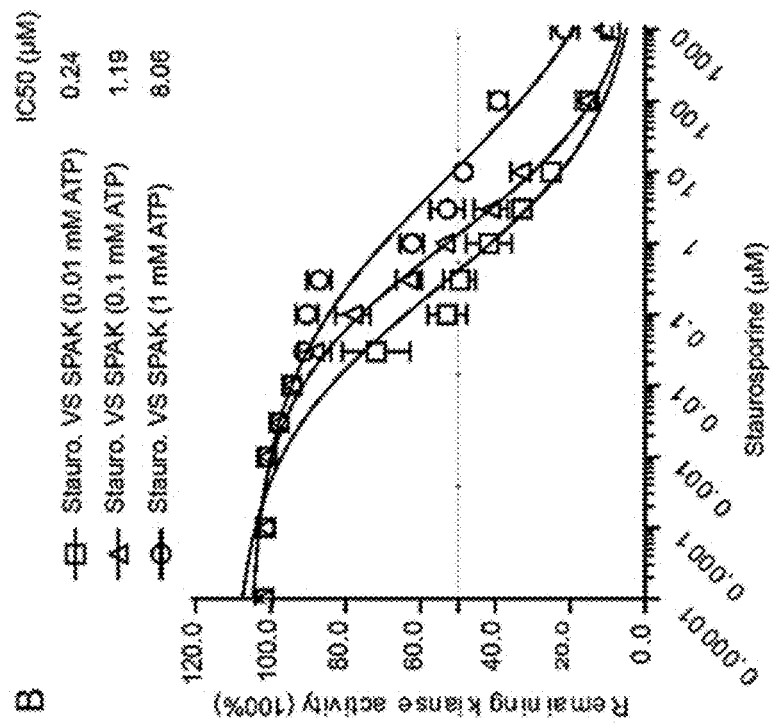
FIG. 4A and FIG. 4B show representative data demonstrating the effect of increasing concentrations of ZT-1a and staurosporine on SPAK activity at different ATP concentrations.
Figure 4B:
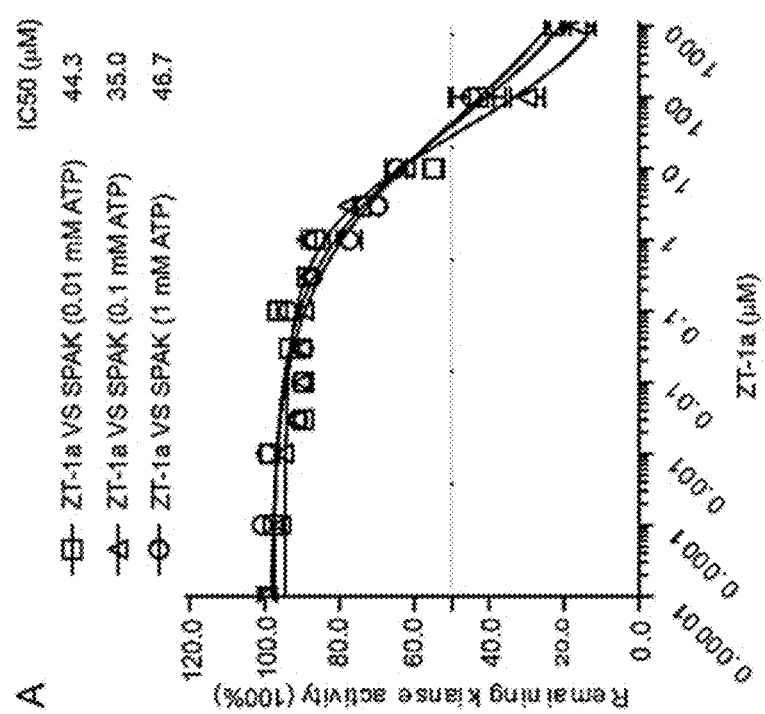

Next, it was tested whether kinase inhibition by ZT-1a reflects competition for ATP binding to kinase, as compared to the non-specific ATP-competitive kinase inhibitor, staurosporine, which, in addition to inhibiting SPAK/OSR1 activity, binds to as many as 253 human protein kinases. As shown in FIG. 4A, staurosporine $IC_{50}$ values increased in a dose-proportional manner with increasing ATP concentrations, in contrast to the unchanged ZT-1a $IC_{50}$ values (FIG. 4B). Without wishing to be bound by theory, these results suggest that ZT-1a inhibits SPAK kinase in a non-ATP-competitive manner. The kinase selectivity of ZT-1a was further assessed using standard radioisotopic enzymatic assays against a panel of 140 recombinant kinases (Dundee profiling, Table 2) (Bain et al. (2007) The Biochemical journal 408, 297-315). ZT-1a at a concentration of 10 µM inhibited only MAPKAP-K2 activity 85±7% compared to DMSO control, representing high kinase selectivity.

Referring to Table 2, ZT-1a was tested at 10 and 1 µM against a panel of 140 recombinant kinases in an enzymatic activity-based assay performed by the International Centre for Kinase Profiling in the MRC Protein Phosphorylation and Ubiquitylation Unit. Values represent % residual kinase activity (mean+/−SEM, n=3). Kinases labelled with an asterick* are inhibited ≥50% by ZT-1a.

TABLE 2

| Kinases | Concentration (µM) 10 | Concentration (µM) 1 |
| --- | --- | --- |
| ABL | 68 ± 16 | 85 ± 4 |
| AMPK (hum) | 108 ± 4 | 126 ± 4 |
| ASK1 | 100 ± 11 | 101 ± 3 |
| Aurora A | 65 ± 1 | 73 ± 19 |
| Aurora B | 92 ± 15 | 119 ± 6 |
| BRK | 103 ± 2 | 116 ± 12 |
| BRSK1 | 88 ± 22 | 108 ± 14 |
| BRSK2 | 104 ± 0 | 115 ± 14 |
| BTK | 73 ± 2 | 113 ± 1 |
| CAMK1 | 71 ± 31 | 60 ± 5 |
| CAMKKb | 102 ± 9 | 115 ± 10 |
| CDK2-Cyclin A | 125 ± 6 | 128 ± 12 |
| CDK9-Cyclin T1 | 108 ± 1 | 104 ± 0 |
| CHK1 | 109 ± 8 | 111 ± 11 |
| CHK2 | 68 ± 6 | 106 ± 1 |
| CK1γ2 | 124 ± 23 | 112 ± 12 |
| CK1δ | 114 ± 9 | 116 ± 5 |
| CK2 | 59 ± 16 | 72 ± 15 |
| CLK2* | 33 ± 45 | 68 ± 12 |
| CSK | 106 ± 29 | 96 ± 8 |
| DAPK1 | 159 ± 11 | 131 ± 8 |
| DDR2 | 99 ± 8 | 111 ± 20 |
| DYRK1A | 103 ± 1 | 119 ± 7 |
| DYRK2 | 97 ± 10 | 111 ± 15 |
| DYRK3 | 56 ± 15 | 113 ± 6 |
| EF2K | 56 ± 2 | 104 ± 13 |
| EIF2AK3 | 100 ± 3 | 114 ± 2 |
| EPH-A2 | 78 ± 11 | 89 ± 23 |
| EPH-A4 | 90 ± 11 | 59 ± 33 |
| EPH-B1 | 80 ± 19 | 77 ± 15 |
| EPH-B2 | 81 ± 8 | 77 ± 2 |
| EPH-B3 | 84 ± 6 | 88 ± 6 |
| EPH-B4 | 151 ± 33 | 100 ± 8 |
| ERK1 | 109 ± 18 | 107 ± 16 |
| ERK2 | 75 ± 3 | 111 ± 25 |
| ERK5 | 114 ± 5 | 120 ± 9 |
| ERK8 | 63 ± 3 | 104 ± 11 |
| FGF-R1 | 101 ± 15 | 93 ± 6 |
| GCK | 97 ± 3 | 112 ± 4 |
| GSK3b* | 38 ± 12 | 39 ± 4 |
| HER4 | 84 ± 1 | 85 ± 8 |
| HIPK1 | 90 ± 4 | 98 ± 13 |
| HIPK2 | 91 ± 4 | 90 ± 14 |
| HIPK3 | 76 ± 2 | 84 ± 3 |
| IGF-1R | 123 ± 3 | 145 ± 2 |
| IKKb | 78 ± 3 | 101 ± 0 |
| IKKe | 59 ± 5 | 87 ± 13 |
| IR | 86 ± 13 | 105 ± 2 |
| IRAK1 | 95 ± 7 | 128 ± 2 |
| IRAK4 | 127 ± 11 | 127 ± 0 |
| IRR | 95 ± 4 | 105 ± 5 |
| JAK2 | 123 ± 8 | 125 ± 6 |
| JNK1 | 110 ± 5 | 106 ± 4 |
| JNK2 | 147 ± 51 | 102 ± 2 |
| JNK3 | 60 ± 10 | 63 ± 15 |
| Lck | 127 ± 14 | 112 ± 13 |
| LKB1 | 115 ± 11 | 107 ± 8 |
| MAP4K3 | 88 ± 2 | 134 ± 5 |
| MAP4K5 | 76 ± 9 | 95 ± 28 |
| MAPKAP-K2* | 13 ± 7 | 91 ± 13 |
| MAPKAP-K3 | 72 ± 8 | 96 ± 26 |
| MARK1 | 91 ± 5 | 104 ± 16 |
| MARK2 | 89 ± 15 | 103 ± 8 |
| MARK3 | 68 ± 8 | 71 ± 6 |
| MARK4 | 59 ± 9 | 68 ± 8 |
| MEKK1 | 93 ± 16 | 109 ± 1 |
| MELK | 63 ± 3 | 130 ± 34 |
| MINK1 | 108 ± 6 | 107 ± 5 |
| MKK1 | 114 ± 17 | 106 ± 2 |
| MKK2 | 81 ± 27 | 126 ± 2 |
| MKK6 | 82 ± 16 | 102 ± 12 |
| MLK1 | 81 ± 21 | 94 ± 4 |
| MLK3 | 114 ± 3 | 119 ± 11 |
| MNK1 | 87 ± 2 | 78 ± 19 |
| MNK2 | 105 ± 3 | 100 ± 7 |
| MPSK1 | 105 ± 2 | 110 ± 6 |
| MSK1 | 112 ± 14 | 114 ± 6 |
| MST2 | 113 ± 2 | 115 ± 4 |
| MST3 | 113 ± 15 | 109 ± 8 |
| MST4 | 63 ± 0 | 63 ± 10 |
| NEK2a | 91 ± 6 | 85 ± 12 |
| NEK6 | 108 ± 1 | 107 ± 6 |
| NUAK1 | 61 ± 16 | 52 ± 7 |
| OSR1 | 98 ± 3 | 106 ± 9 |
| p38a MAPK | 113 ± 2 | 128 ± 7 |
| p38b MAPK | 124 ± 0 | 124 ± 1 |
| p38d MAPK | 112 ± 2 | 95 ± 1 |
| p38g MAPK | 100 ± 6 | 100 ± 11 |
| PAK2 | 93 ± 8 | 110 ± 4 |
| PAK4 | 51 ± 3 | 81 ± 16 |
| PAK5 | 93 ± 4 | 93 ± 26 |
| PAK6 | 75 ± 4 | 69 ± 2 |
| PDGFRA | 80 ± 7 | 84 ± 11 |
| PDK1 | 69 ± 17 | 92 ± 6 |
| PHK | 107 ± 2 | 97 ± 3 |
| PIM1 | 101 ± 8 | 108 ± 19 |
| PIM2 | 93 ± 3 | 93 ± 5 |
| PIM3 | 99 ± 2 | 115 ± 12 |
| PINK | 59 ± 4 | 101 ± 13 |
| PKA* | 50 ± 2 | 80 ± 11 |
| PKBa | 91 ± 4 | 104 ± 1 |
| PKBb | 51 ± 13 | 76 ± 14 |
| PKCa | 83 ± 2 | 97 ± 4 |
| PKCz | 122 ± 28 | 80 ± 11 |
| PKCγ | 120 ± 8 | 133 ± 11 |
| PKD1 | 79 ± 10 | 89 ± 0 |
| PLK1 | 93 ± 21 | 72 ± 1 |
| PRAK* | 41 ± 7 | 78 ± 13 |
| PRK2 | 120 ± 7 | 118 ± 4 |
| RIPK2 | 120 ± 3 | 128 ± 5 |
| ROCK 2 | 101 ± 10 | 109 ± 6 |
| RSK1 | 87 ± 4 | 95 ± 2 |
| RSK2 | 101 ± 3 | 116 ± 5 |
| S6K1 | 81 ± 2 | 119 ± 10 |
| SGK1 | 58 ± 5 | 73 ± 14 |
| SIK2 | 76 ± 8 | 105 ± 16 |
| SIK3 | 88 ± 0 | 104 ± 9 |
| SmMLCK | 98 ± 9 | 99 ± 3 |
| Src | 84 ± 13 | 107 ± 4 |
| SRPK1 | 73 ± 20 | 104 ± 5 |
| STK33 | 100 ± 5 | 114 ± 7 |

TABLE 2-continued

| Kinases | Concentration (μM) | |
| --- | --- | --- |
| | 10 | 1 |
| SYK | 93 ± 1 | 93 ± 12 |
| TAK1 | 103 ± 5 | 117 ± 22 |
| TAO1 | 104 ± 2 | 66 ± 2 |
| TBK1 | 94 ± 3 | 119 ± 10 |
| TESK1 | 77 ± 10 | 109 ± 3 |
| TGFBR1 | 77 ± 5 | 63 ± 9 |
| TIE2 | 73 ± 11 | 139 ± 74 |
| TLK1 | 124 ± 4 | 130 ± 13 |
| TrkA | 91 ± 7 | 108 ± 9 |
| TSSK1 | 74 ± 6 | 99 ± 2 |
| TTBK1 | 102 ± 2 | 119 ± 5 |
| TTBK2 | 98 ± 34 | 101 ± 32 |
| TTK | 91 ± 5 | 104 ± 2 |
| ULK1 | 89 ± 13 | 87 ± 10 |
| ULK2* | 49 ± 9 | 110 ± 11 |
| VEG-FR | 88 ± 28 | 113 ± 10 |
| WNK1 | 122 ± 35 | 125 ± 17 |
| YES1 | 98 ± 7 | 109 ± 3 |
| ZAP70 | 97 ± 9 | 120 ± 1 |

Results are presented as the percentage of kinase activity compared with control incubations in which inhibitor was omitted. The results are means±S.D. of triplicate determinations.

b. ZT-1a Disrupts SPAK Interaction with WNK but not with MO25α

Figures 5A, 5B:
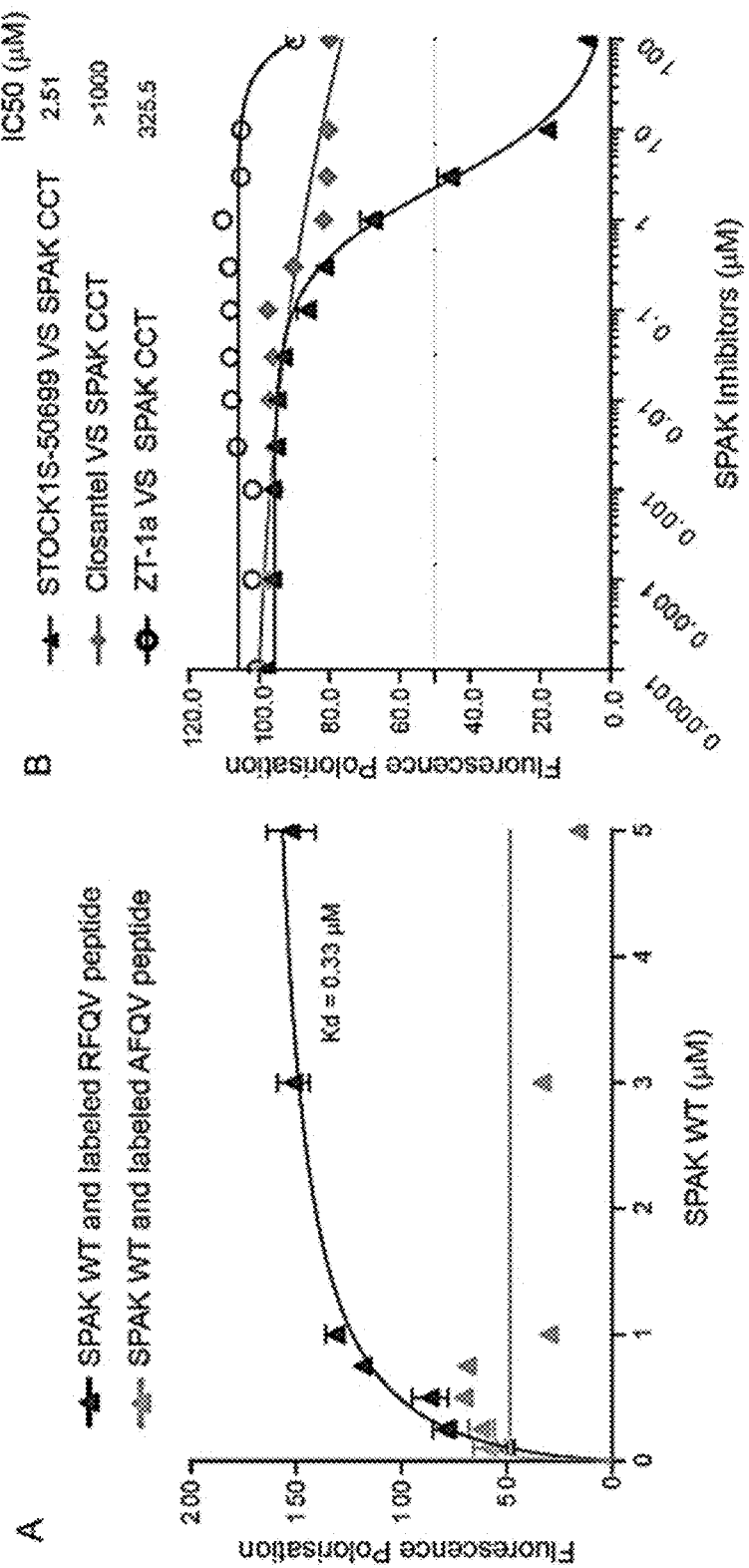
FIG. 5A and FIG. 5B show representative evidence that SPAK associates with WNK1 in a manner disrupted by SPAK CCT mutation.
Figure 6:
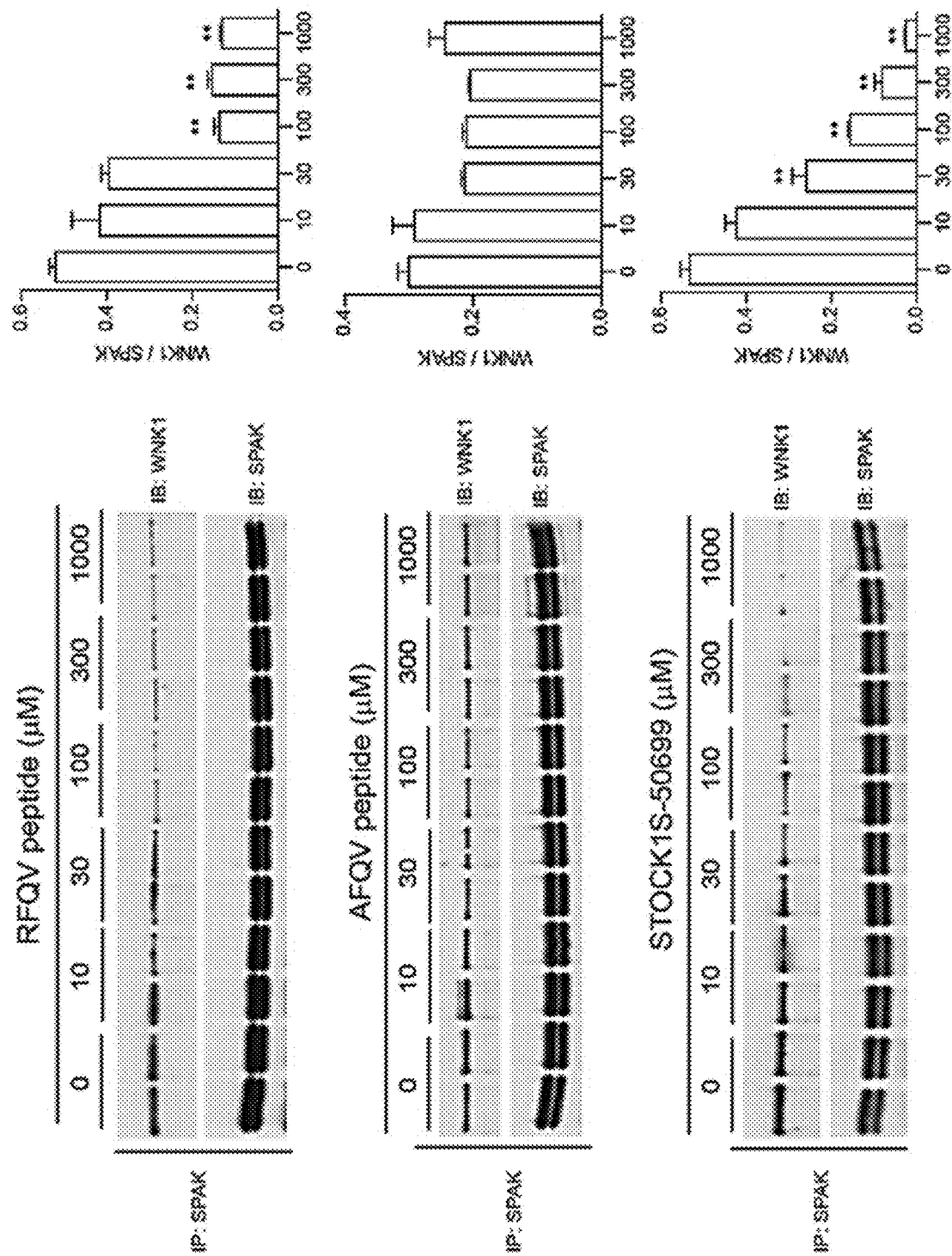
FIG. 6 shows representative evidence that SPAK associates with WNK1 and interaction is disrupted by ZT-1a and its analogs.
Figure 6:
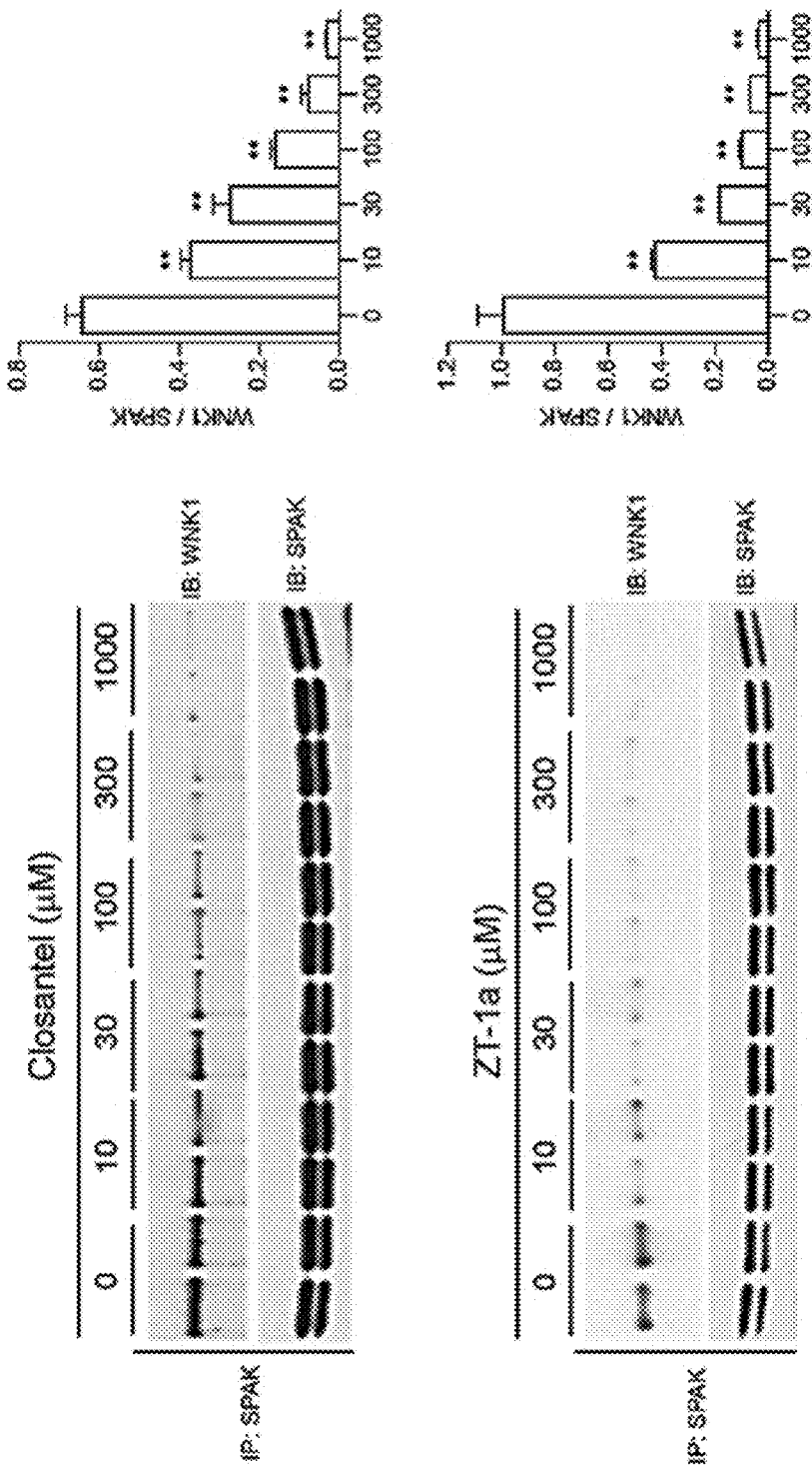
Figure 7B:
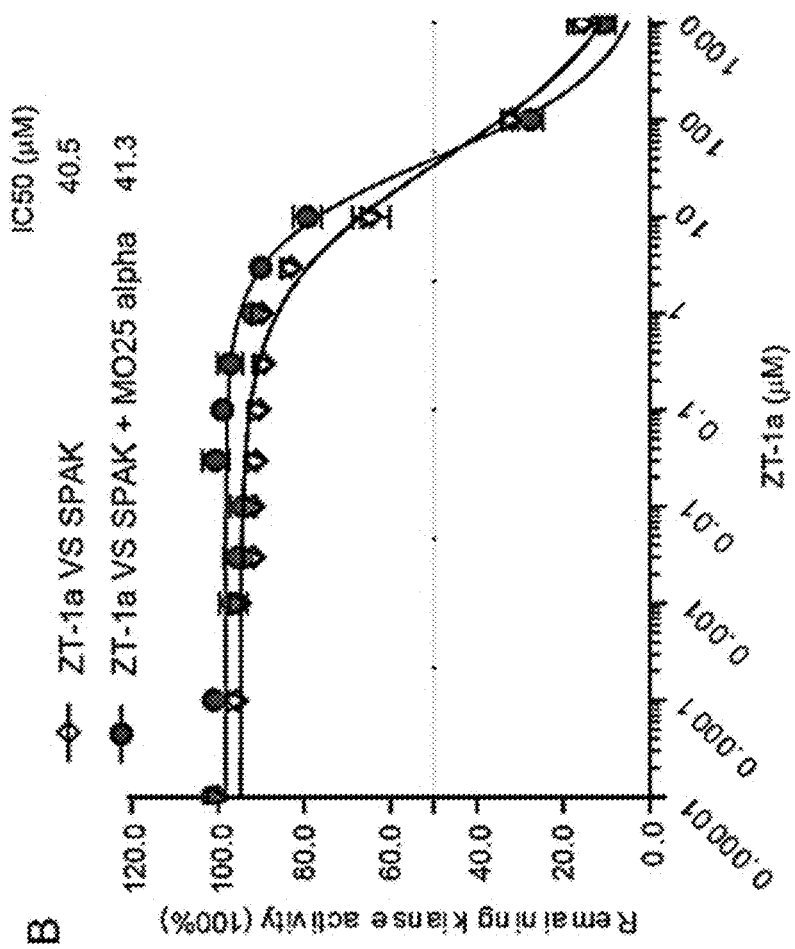
FIG. 7A and FIG. 7B show representative data illustrating the effect of increasing concentrations of ZT-1a on SPAK activity in the absence or presence of wild-type MO25 alpha.
Figure 7A:
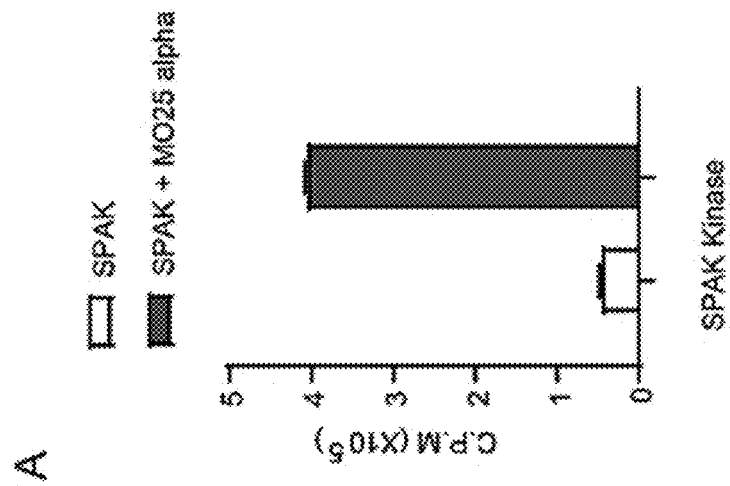

Crystallographic analysis of the human OSR1 conserved carboxy-terminal (CCT) domain complexed to an RFXI motif-containing peptide derived from WNK (Villa et al. (2007) EMBO reports 8, 839-845) has shown that the highly conserved Leu473 CCT (mouse SPAK Leu502) forms critical hydrophobic contacts with the Phe residue of the RFXI motif. In vitro fluorescence polarization studies have confirmed that the RFXI motif-containing WNK peptide binds to purified wild-type SPAK protein with 0.3 μM binding affinity, an interaction disrupted by STOCK1S-50699 with $IC_{50}$ 2.51 μM) (FIG. 5A and FIG. 5B). Closantel and ZT-1a did not disrupt binding between WNK4 and the SPAK CCT domain, suggesting the ZT-1a binding site lies outside the CCT domain (FIG. 5A and FIG. 5B). Nonetheless, co-immunoprecipitation of WNK1 with SPAK from HEK293 cell lysates was potently abolished by ZT-1a (FIG. 6). $IC_{50}$ values for ZT-1a binding were not significantly altered by addition of MO25a, which activates SPAK/OSR1 up to 100-fold and increases SPAK/OSR1-mediated in vitro phosphorylation of all CCCs (de Los Heros et al. (2014) The Biochemical journal 458, 559-573; Filippi et al. (2011) The EMBO journal 30, 1730-1741) by 8-fold (FIG. 7A and FIG. 7B).

Referring to FIG. 5A, analysis of SPAK-WNK interaction by fluorescence polarization is shown. Purified human SPAK 452-547(end) and human SPAK 452-547 with L491A (equivalent to L502 in mouse) were diluted appropriately and mixed at a 1:1 volume ratio with 20 nM Lumino-Green-labelled WNK peptide (RFQV or AFQV) to the concentration stated in the Figure (with the final peptide concentration consistent at 10 nM), and fluorescent polarization measurements were made. Binding curves, assuming one-site-specific binding, were then generated with Prism6 using milli-polarization (mP) units.

Referring to FIG. 5B, under the assay conditions used in FIG. 5A, concentration-dependent decreases in fluorescence polarization were determined for STOCK1S-50699 ($IC_{50}$ 2.51 μM), Closantel ($IC_{50}$>1000 M), and ZT-1a ($IC_{50}$ 325.5 μM).

Referring to FIG. 6, evidence that SPAK associates with WNK1, and interaction is disrupted by SPAK CCT mutation is shown. Non-transfected HEK293 cell lysates were incubated with the RFQV peptide (SEEGKPQLVGRFQVTSSK), AFQV peptide (SEEGKPQLVGAFQVTSSK), STOCK1S-50699, Closantel or ZT-1a for 30 min on ice and subjected to SPAK antibody immunoprecipitation. Immunoprecipitates were subjected to immunoblot probed with antibody to total WNK1 and antibody to total SPAK.

Referring to FIG. 7A, the activation of SPAK kinase by MO25α is shown. SPAK was assayed in the absence or presence of five-fold molar excess of wild-type MO25α.

Referring to FIG. 7B, kinetic data was determined for ZT-1a in the absence or presence of five-fold molar excess of wild-type MO25α. Data points are the average of three determinations, and the error bars are +/−SEM. IC50 results are 40.5 and 41.3 μM for ZT-1a in the respective absence or presence of wild-type MO25α.

c. ZT-1a Reduces NKCC1 and KCC2 Phosphorylation at the Critical SPAK-Regulated Phosphorylation Sites To assess CCC phosphorylation in response to ZT-1a, HEK293 cells were exposed for 30 min either to control isotonic conditions or to hypotonic low [Cl⁻] (to activate SPAK/OSR1), then treated with increasing ZT-1a concentrations for an additional 30 min. In a dose-dependent manner (1-10 μM), ZT-1a markedly inhibited SPAK/OSR1 phosphorylation at Ser373/Ser325 (i.e., the activating site phosphorylated by WNK1) and NKCC1 phosphorylation at Thr203/Thr207/Thr212 (SPAK/OSR1 target sites whose phosphorylation is required for maximal transporter activity) in hypotonic low [Cl⁻] conditions as well as in control isotonic conditions (FIG. 1B and FIG. 3). These effects were paralleled by a similar suppression of KCC2 Thr906/1007 phosphorylation, consistent with WNK-SPAK/OSR1-mediated phosphorylation of these residues (de Los Heros et al. (2014) The Biochemical journal 458, 559-573; Zhang et al. (2016) Scientific reports 6, 35986). Without wishing to be bound by theory, these results show that ZT-1a reduces the stimulatory phosphorylation of NKCC1 at Thr203/Thr207/Thr212 and the inhibitory phosphorylation of KCCs sites-1/2 phosphorylation.

d. ZT-1a Promotes KCC-Dependent Cellular Cl⁻ Extrusion

Figure 8:
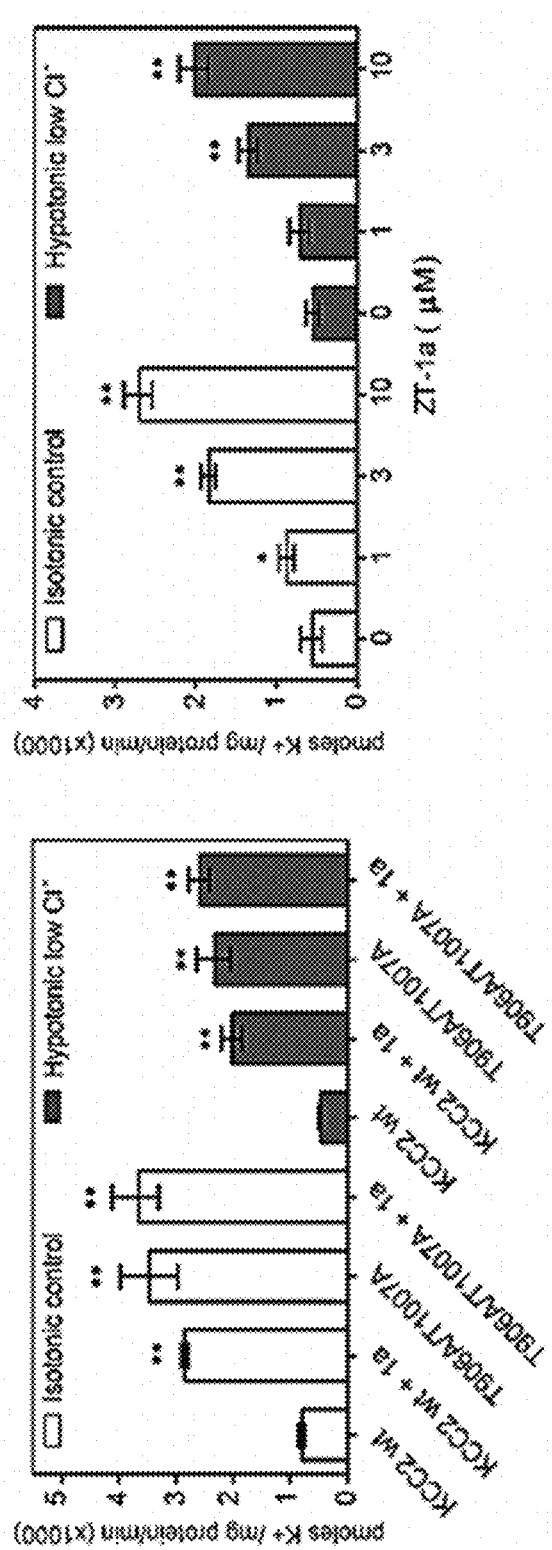

The potential clinical utility of specific KCC2 activators has led to intense development efforts (Gagnon et al. (2013) Nature medicine 19, 1524-1528). The ability of ZT-1a to decrease inhibitory KCC2 phosphorylation at Thr906/1007 prompted an assessment of ZT-1a's effect on KCC2 activity by measuring $^{86}Rb^+$ uptake in isotonic or hypotonic low Cl⁻ conditions (FIG. 8). Low KCC2 activity observed in wild-type (WT) cells was consistent with maximal KCC2 phosphorylation at Thr906/1007 in hypotonic low [Cl⁻] conditions or isotonic high [K⁺] (Kahle et al. (2013) Trends Neurosci 36, 726-737). In contrast, cells expressing KCC2 double mutant Thr906Ala/Thr1007Ala, mimicking activating dephosphorylation at these sites (Friedel et al. (2015) Science signaling 8, ra65), exhibited 3.4-fold increased KCC2 activity compared to WT KCC2 (p<0.01; n=3). ZT-1a activated WT KCC2>2.6-fold (p<0.01; n=3), whereas ZT-1a treatment failed only minimally increased (by 7±2%) activity of KCC2 double mutant Thr906Ala/Thr1007Ala (p>0.05; n=3; FIG. 8). Without wishing to be bound by theory, these results show that ZT-1a facilitates KCC2-dependent Cl⁻ extrusion by decreasing its SPAK-dependent inhibitory phosphorylation at Thr906/Thr1007.

Referring to FIG. 8, $^{86}Rb^+$ uptake assays in the presence of ZT-1a is shown. Specifically, referring to the Left Panel, HEK293 cells were transfected with constructs encoding the indicated WT or mutant constructs of N-terminally FLAG-tagged KCC2. 36 h post-transfection cells were exposed for 30 min to either control isotonic conditions or hypotonic low [Cl⁻] conditions (to activate the SPAK/OSR1 pathway), then treated in the same conditions for an additional 30 min with the indicated ZT-1a concentrations in the presence of 1 mM ouabain (Na⁺/K⁺-ATPase inhibitor) and 0.1 mM bumetamide (NKCC1 inhibitor). $^{86}Rb^+$ uptake was allowed to proceed for 10 min and was then quantified by scintillation counting. $^{86}Rb^+$ uptake CPM's were normalized per mg protein for each condition and plotted for both isotonic and hypotonic conditions. Referring to the Right Panel, HEK293 cells were transfected with constructs encoding wild type N-terminally FLAG epitope-tagged KCC2. 36 hrs post-transfection cells were exposed for 30 min to either control isotonic conditions or hypotonic low [Cl⁻] conditions (to activate the SPAK/OSR1 pathway), then treated for an additional 30 min in the same conditions with the indicated concentrations of ZT-1a in the presence of 1 mM ouabain and 0.1 mM bumetamide. 10 min $^{86}Rb^+$ uptake values were quantified by scintillation counting, normalized per mg protein for each condition and plotted for both isotonic and hypotonic conditions. Statistical significance was determined at p<0.05 (both panels).

e. SPAK Inhibitory Effects of ZT-1a on CCC Phosphorylation are Short Acting and Reversible In Vivo.

Figure 9A:
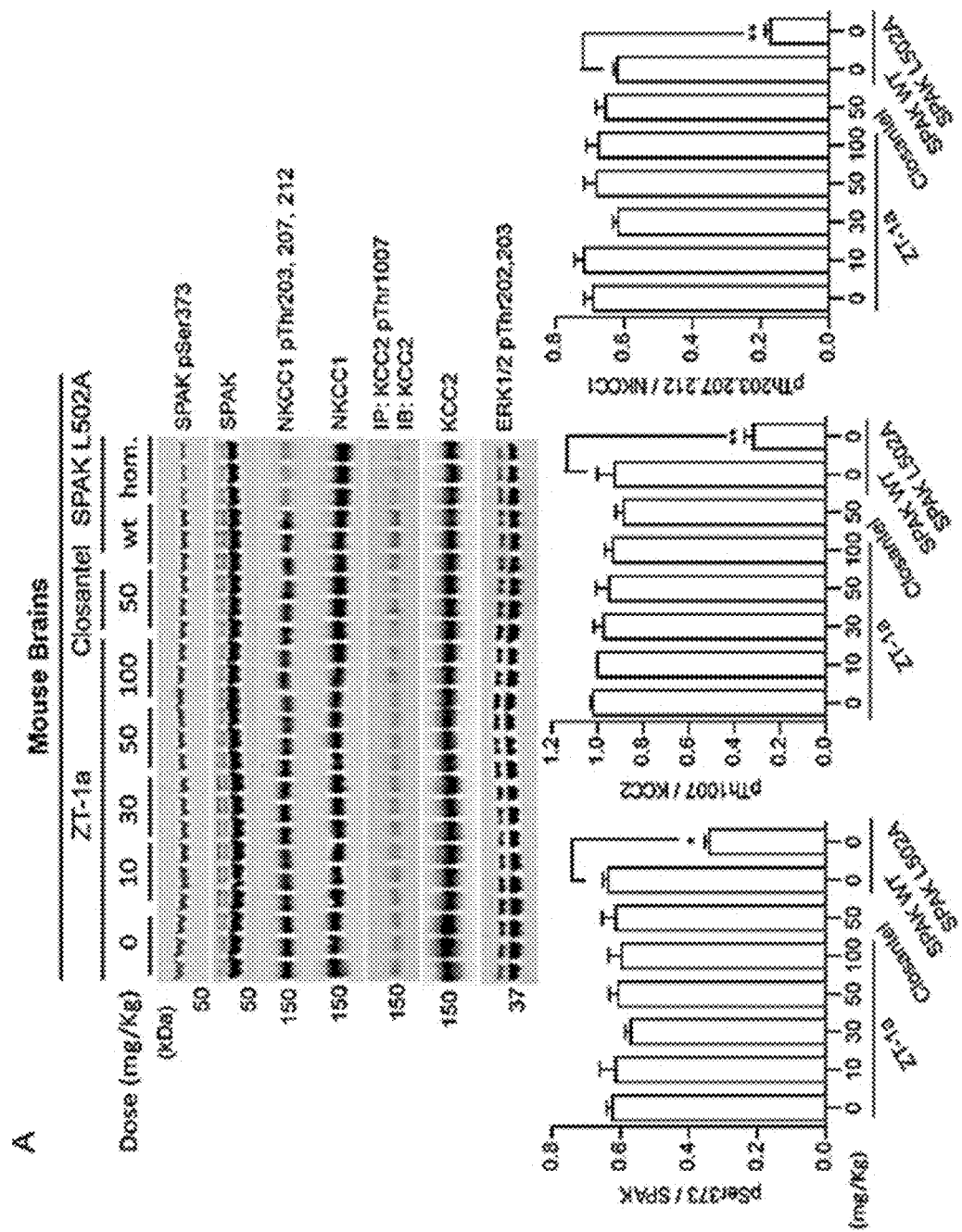
FIG. 9A and FIG. 9B show a representative in vivo pharmacodynamic analysis of ZT-1a and Closantel from brain (FIG. 9A) and kidney (FIG. 9B), which were administered via subcutaneous injection at the indicated doses.
Figure 9B:
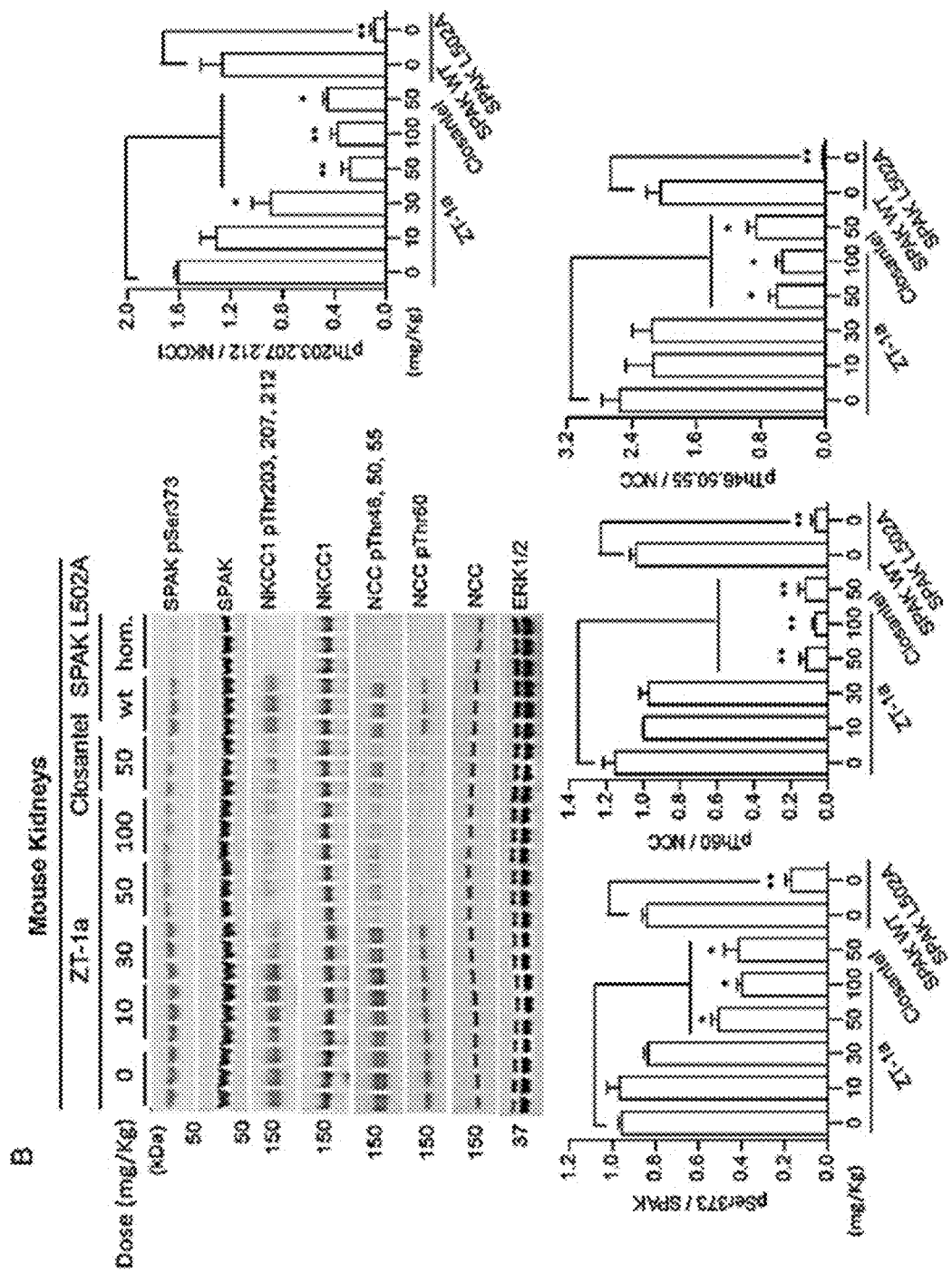

To define ZT-1a efficacy in naive mice in vivo, phosphorylation of SPAK, NKCC1 and NCC in kidney and phosphorylation of SPAK, NKCC1 and KCC2 in brain were examined, after intraperitoneal (i.p.) administration of either ZT-1a (10, 30, 50 and 100 mg/kg) or Closantel (50 mg/kg as a reference). NCC phosphorylation (pThr46/50/55/60) and NKCC1 phosphorylation (pThr203/207/212) was reduced ~83-90±7.9% in naive WT kidneys 30 minutes after ZT-1a administration (50 mg/kg; p<0.01 n=3; FIG. 9B). In contrast, 60 minutes after administration of ZT-1a or Closantel, neither drug reduced KCC2 phosphorylation (pThr1007) or NKCC1 phosphorylation (pThr203/207/212) in naïve brains (FIG. 9A). KCC2 Leu502 is a residue required for high affinity recognition of the RFXI motif in SPAK upstream activator WNKs, as well as in its substrates NCC and KCC2/4 (Villa et al. (2007) EMBO reports 8, 839-845; Zhang et al. (2015) Human molecular genetics 24, 4545-4558). A ~34±4.6% reduction in KCC2 phosphorylation at pThr1007 was detected in brains from SPAK$^{502A/502A}$ mice; p<0.01; n=3; FIG. 9A), a model of Gitelman Syndrome (Zhang et al. (2015) Human molecular genetics 24, 4545-4558). Thus, systemically administered ZT-1a has low efficacy in naïve brains, indicating apparently inefficient transport of ZT-1a across the blood-brain barrier (BBB), and likely reflecting in part its Tin of 1.8 hr in mice, with AUC of 2340 hr*ng/mL and % F of 2.2% (Table 3).

Referring to FIG. 9A and FIG. 9B, in vivo pharmacodynamic analysis of ZT-1a was performed. ZT-1a and Closantel were administered via subcutaneous injection at the indicated doses. Brain (FIG. 9A) and kidney (FIG. 9B) tissues were collected, and endogenous proteins were subjected to immunoblot probed with SPAK, NKCC1 and NCC phospho-specific antibodies.

Referring to Table 3, ZT-1a pharmacokinetics were determined following a single 5 mg/kg intravenous (IV) dose and a single 10 mg/kg oral (PO) dose in ICR mice (N=3 at each time point). Blood samples were collected at 0.08, 0.25, 0.5, 1, 2, 4, 8, 10 & 24 hr (IV) & 0.25, 0.5, 1, 2, 4, 8, 10 & 24 hr (PO) post dose. Samples were subjected to drug assay by LC-MS/MS, and data were analyzed by WinNonlin V6.3. $T_{max}$=time of maximum plasma concentration, $C_{max}$=maximum plasma concentration, AUC=area under the curve (measure of exposure), $T_{1/2}$=half life, CL=plasma clearance, Vz=volume of distribution, MRT, mean residence time; F=oral bioavailability.

TABLE 3

| | Route | Dose (mg/kg) | $t_{1/2}$ hr | $T_{max}$ hr | $C_{max}$ ng/mL | $C_0$ ng/mL | $AUC_{(0-t)}$ ng*hr/mL | $AUC_{(0-\infty)}$ ng*hr/mL |
|---|---|---|---|---|---|---|---|---|
| Plasma | IV | 5 | 1.8 | 0.08 | 6910 | 14900 | 2340 | 2350 |
| | PO | 10 | 2.6 | 0.25 | 94 | — | 97.3 | 105 |

Figure 10A:
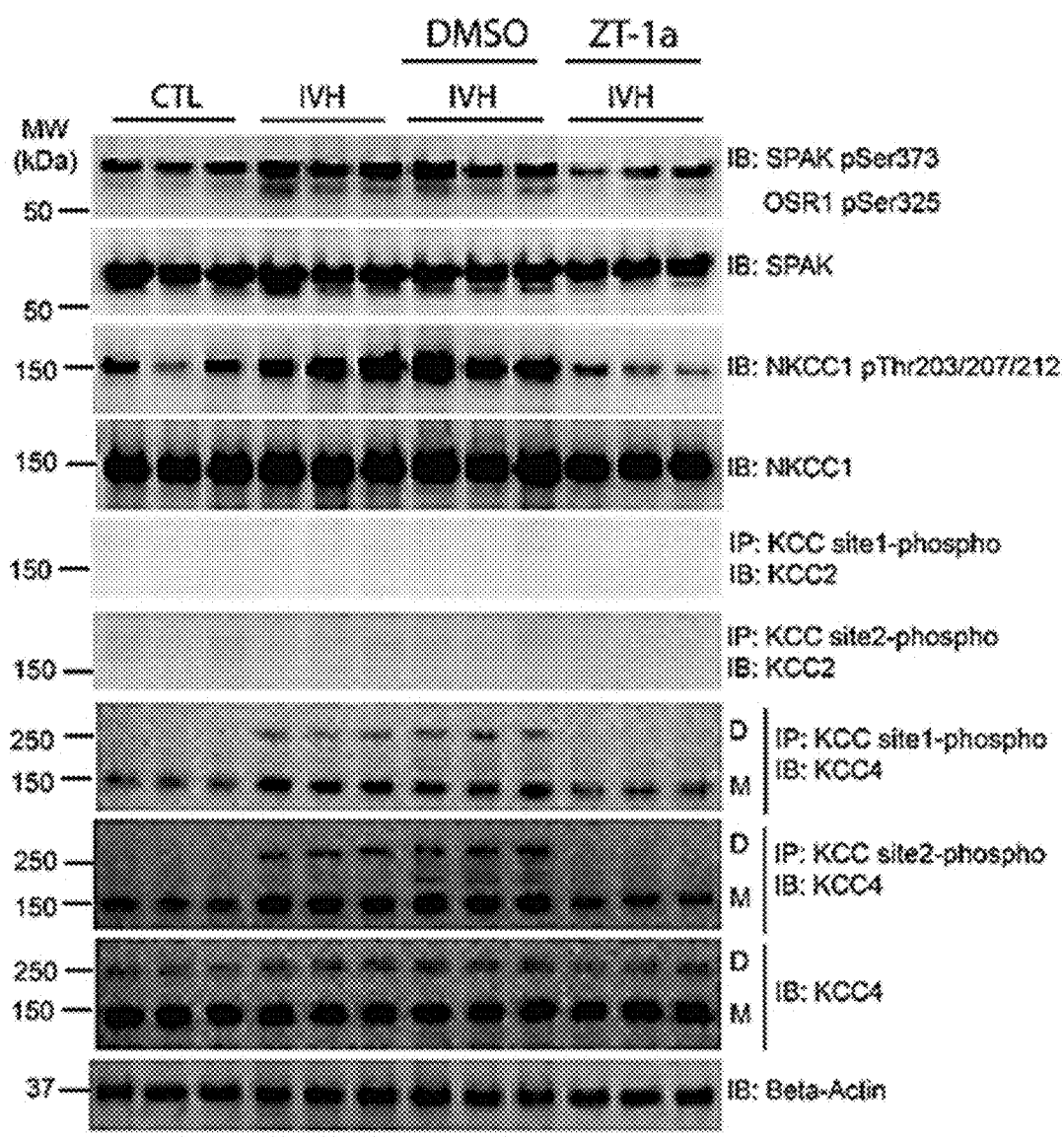
FIG. 10A and FIG. 10B show representative data demonstrating that intracerebroventricular (ICV) delivery of ZT-1a normalizes pathological CSF hypersecretion by decreasing choroid plexus CCC phosphorylation.
Figure 10B:
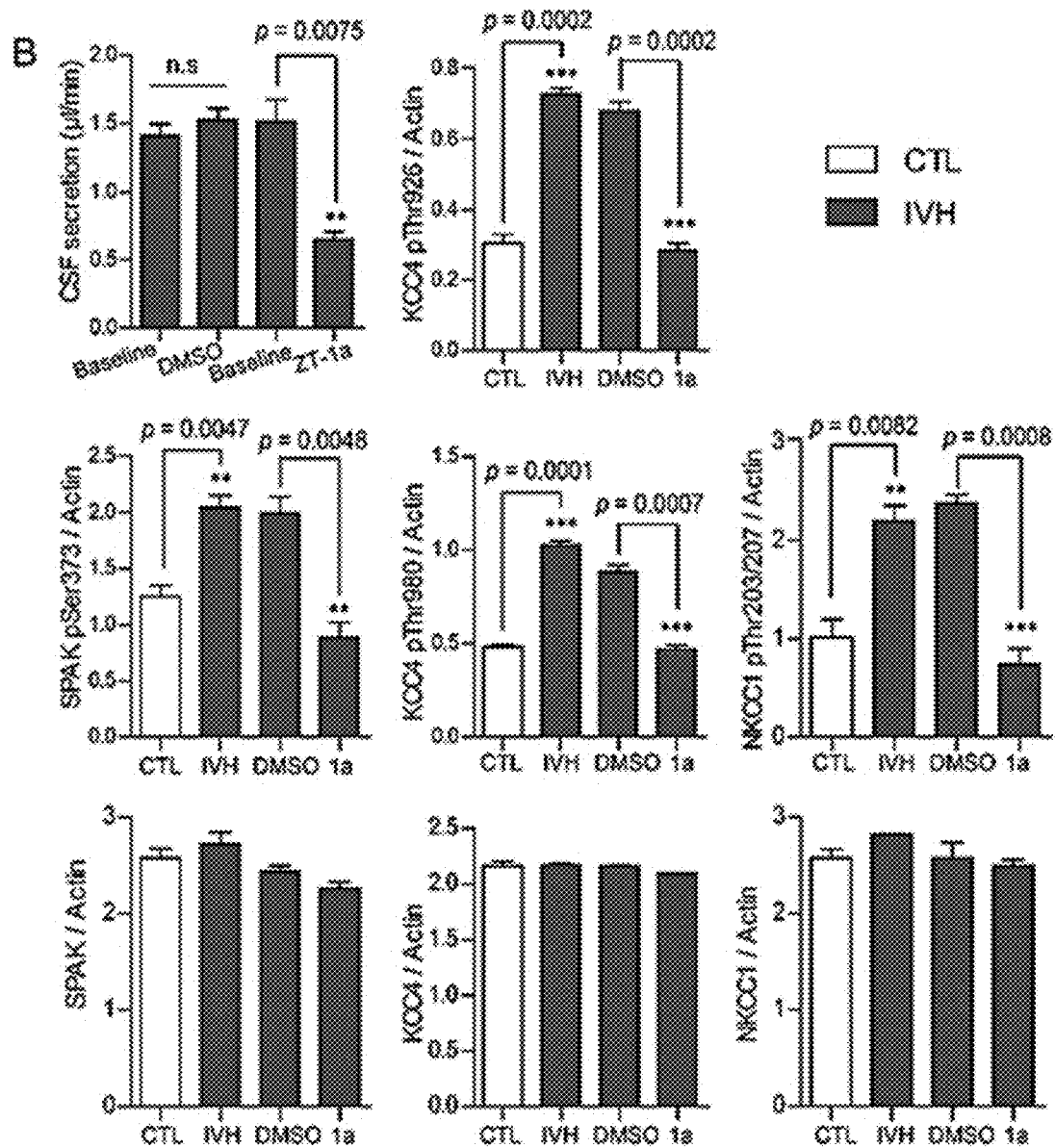

| | Route | Vz L/kg | Cl mL/kg*min | $MRT_{(0-\infty)}$ hr | F % |
|---|---|---|---|---|---|
| Plasma | IV | 0.948 | 35.5 | 0.45 | — |
| | PO | — | — | 3.3 | 2.2 | f. Intracerebroventricular (ICV) Delivery of ZT-1a Normalizes Pathological CSF Hypersecretion by Decreasing Choroid Plexus CCC Phosphorylation IVH-triggered TLR4 signaling stimulates CSF secretion >3.5-fold to cause hemorrhagic hydrocephalus by increasing functional expression of pSPAK and pNKCC1 in the choroid plexus epithelium (CPe) (Karimy et al. (2017) Nature medicine 23, 997-1003). It was hypothesized that intracerebroventricular (ICV) administration of ZT-1a, bypassing the BBB, might permit therapeutic efficacy by allowing ZT-1a access to SPAK-NKCC1 in the CPe. The effects of ICV ZT-1a delivery were tested on pSPAK, pNKCC1, pKCC4, in rat choroid plexus in the setting of experimental hemorrhagic hydrocephalus, as described (Karimy et al. (2017) Nature medicine 23, 997-1003)). (KCC2 is expressed in choroid plexus at very low or undetectable levels). ZT-1a reduced IVH-induced expression of pSPAK by 55±3.6%; p<0.01; n=3) and pNKCC1 by 69±4.3%; p<0.001; n=3; FIG. 10A and FIG. 10B). ZT-1a reduced post-IVH KCC4 phosphorylation at Thr926 and Thr980 (corresponding to KCC2 Thr906 and Thr1007) in CPe by ~45-48±5.1%; p<0.001; n=3; FIG. 10A and FIG. 10B). Consistent with these results, ZT-1a treatment for 48 hr at 10 mmol decreased post-IVH CSF hypersecretion by ~57±6.2% (p<0.01), in contrast to the lack of effect of DMSO vehicle treatment (p>0.05) (FIG. 10B). Without wishing to be bound by theory, these data suggest ICV administration of ZT-1a can effectively modulate pathological CSF secretion by decreasing SPAK-CCC phosphorylation.

Referring to FIG. 10A, the effect of ZT-1a (ICV; 10 mmol) on IVH-induced phosphorylation of SPAK/OSR1, NKCC1, KCC2, and KCC4 in CPE, as measured in control rats (CTL) and in rats 48 hrs post-IVH treated with ZT-1a or vehicle (n=3 for all groups) is shown. CPE lysates were harvested and subjected to immunoprecipitation (IB) and immunoblot (IB) with the indicated antibodies. D, dimeric KCC2; M, monomeric KCC2. Molecular mass is indicated in kDa.

Referring to FIG. 10B, the effect of SPAK inhibition by ZT-1a on IVH-induced CSF hypersecretion by CPE is shown. The rate of CSF production (L/min) is presented as means±SEM. **, p<0.01 vs. control; #, p<0.01 vs. IVH but not vs. controls (p>0.05); one-way ANOVA. Quantitation of actin-normalized choroid plexus ion transporter phosphorylation is presented in control rats (CTL) and rats 48 hrs after experimental IVH in the presence or absence of ZT-1a or vehicle (n=3 for all groups). *, p<0.05 versus control rats, one-way ANOVA.

g. Post-Stroke Administration of ZT-1a Reduces Ischemic Cerebral Edema

Ischemic stroke is associated with significant up-regulation of SPAK and NKCC1 phosphorylation in peri-infarct cortex, striatum and corpus callosum (Begum et al. (2015) Stroke 46, 1956-1965). Genetic inhibition of either SPAK or NKCC1 decreases ischemic cerebral edema and improves neurological outcomes (Zhang et al. (2017) Neurochem Int 111, 23-31; Zhao et al. (2017) Journal of cerebral blood flow and metabolism: official journal of the International Society of Cerebral Blood Flow and Metabolism 37, 550-563). The efficacy of ZT-1a on development of cerebral infarct and associated cerebral edema in a mouse model of ischemic stroke was evaluated (Begum et al. (2015) Stroke 46, 1956-1965; Zhao et al. (2017) Journal of cerebral blood flow and metabolism: official journal of the International Society of Cerebral Blood Flow and Metabolism 37, 550-563). Post-stroke administration of ZT-1a (5 mg/kg) at 3 hr reperfusion decreased infarct volume by ~35% (from 78.0±20.0 mm$^3$ in the vehicle-control group to 50.4±27.0 mm$^3$, p<0.05, FIG. 11A and FIG. 11B). Moreover, ZT-1a treatment at either 2.5 or 5 mg/kg reduced cerebral hemispheric swelling by ~36 to 50% as compared to vehicle-control values (p<0.05, FIG. 11B). ZT-1a did not affect regional cerebral blood flow (rCBF) within the 24 hr post-stroke period (FIG. 12A-C). These results show that the novel SPAK inhibitor ZT-1a is effective in reducing ischemic brain infarct and edema.

Figure 11A:
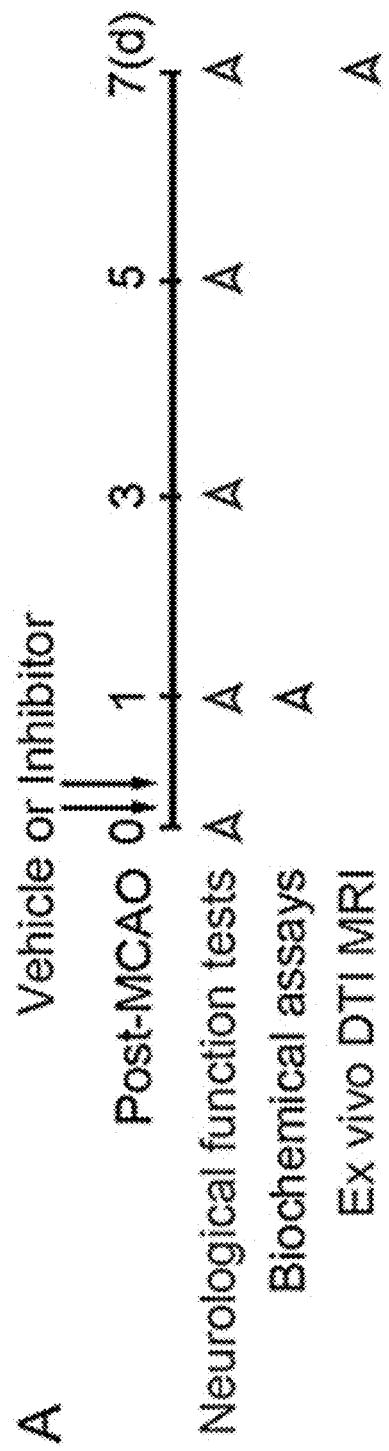
FIG. 11A shows a representative experimental design of an ischemic stroke study.
Figure 12A:
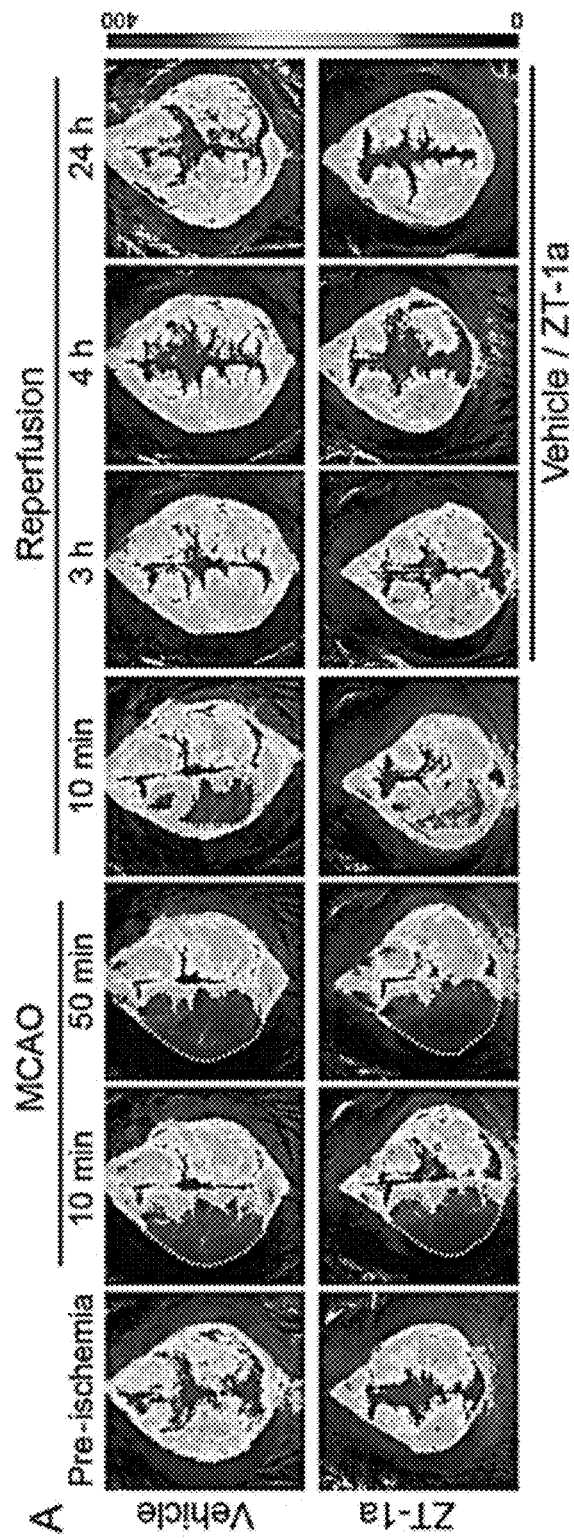
FIG. 12A-C show representative data illustrating that post-stroke administration of ZT-1a or Closantel does not affect regional cerebral blood flow (rCBF) in ischemic mice.
Figures 12B, 12C:
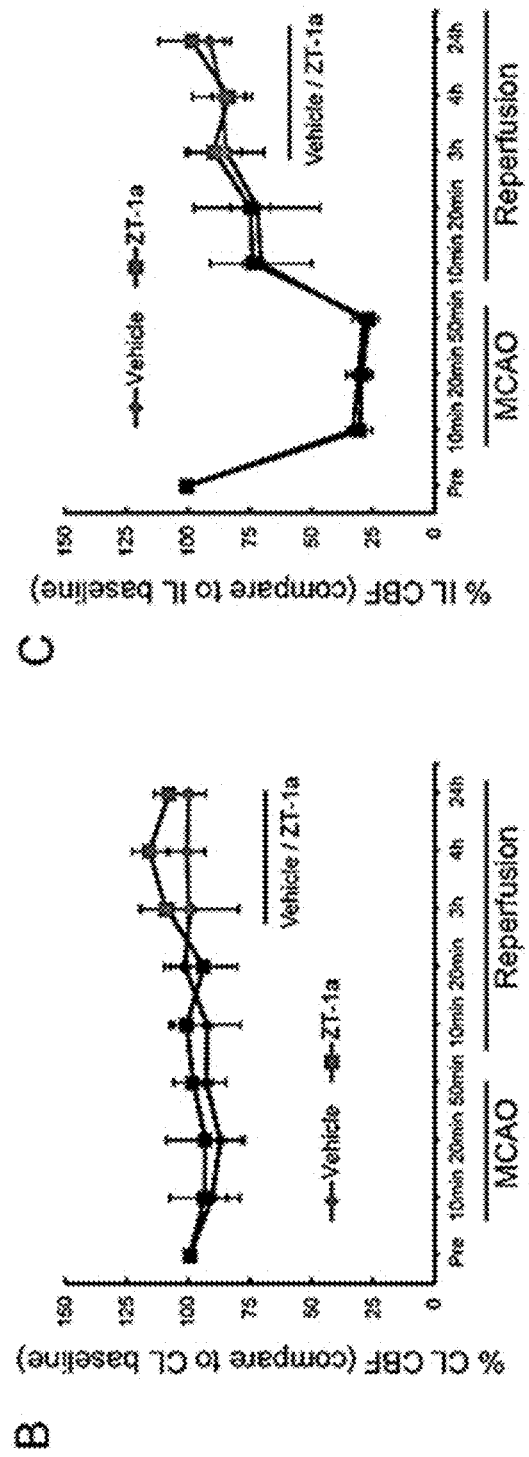

Referring to FIG. 11A, an experimental design of ischemic stroke study is shown. Vehicle or ZT-1a is administered at 3 hrs and 8 hrs post-MCAO.

Figure 11B:
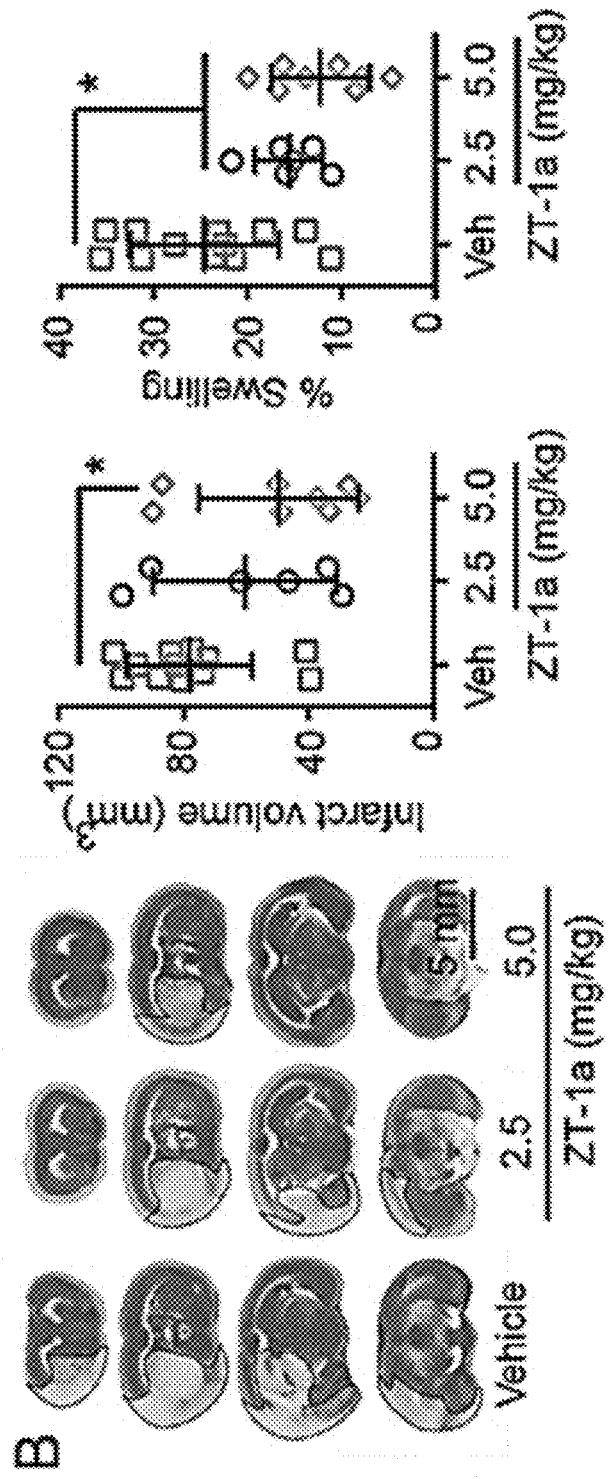
FIG. 11B shows representative images and quantification of infarct volume and hemispheric swelling in TTC-stained coronal sections of mouse brains 24 hrs post-MCAO.

Referring to FIG. 11B, representative images and quantification of infarct volume and hemispheric swelling in TTC-stained coronal sections of mouse brains 24 hrs post-MCAO are shown. Vehicle (DMSO, 2 ml/kg) or ZT-1a (2.5 or 5.0 mg/kg) were administered with an initial half dose at 3 hrs and the second half dose at 8 hr reperfusion via intra-peritoneal injection (i.p.). Data are mean±SD, n=6-12 per group (male). * p<0.05.

Referring to FIG. 12A, representative two-dimensional laser speckle contrast images of rCBF are shown. Vehicle (DMSO) or ZT-1a (2.5 mg/kg/dose) was administered at 3 hr and again at 8 hr post-reperfusion after MCAO, respectively. PseudocolorScale bar indicates relative signal intensity.

Referring to FIG. 12B, no changes of rCBF were detected in the non-ischemic contralateral (CL) hemispheres of vehicle-control or ZT-1a-treated mice. Data are mean±SD, n=3.

Referring to FIG. 12C, similar reduction and recovery of rCBF in the ischemic ipsilateral hemispheres (IL) were detected in the vehicle- or ZT-1a-treated ischemic mice. Data are mean±SD, n=3.

h. ZT-1a Improves Neurological Function after Ischemic Stroke

Figure 13:
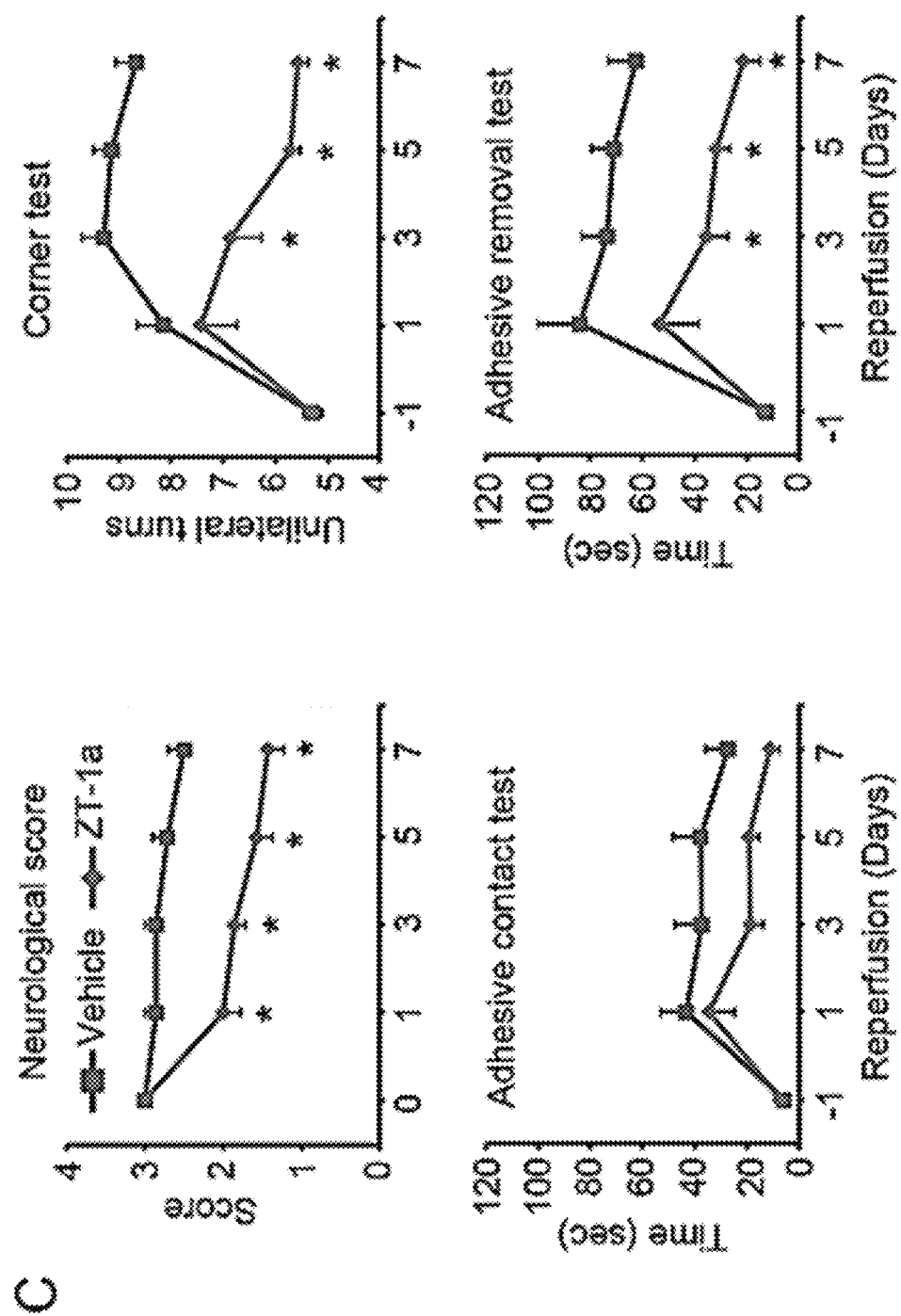
FIG. 13 shows representative data demonstrating neurological deficit scores, corner tests, and adhesive tape contact and adhesive tape removal tests of mice treated with vehicle or ZT-1a 1 day before tMCAO (−1) and at days 0, 1, 3, 5, and 7 post-tMCAO.

The impact of ZT-1a on progression of sensorimotor function deficits in the mouse model of ischemic stroke was further evaluated using an array of neurobehavioral tests. The vehicle-control mice developed persistent severe neurological deficits at days 0-7 after stroke, as reflected in elevated neurological scores of 2.5-2.9 (FIG. 13). ZT-1a-treated mice exhibited a progressive decrease in neurological deficit scores between day 1 (2.0±0.2) and day 7 (1.4±0.2, p<0.05). In the corner test (Zhao et al. (2017) Journal of cerebral blood flow and metabolism: official journal of the International Society of Cerebral Blood Flow and Metabolism 37, 550-563) evaluating post-ischemic sensory and motor deficits, vehicle-control mice exhibited behavioral asymmetries 1 day after stroke that persisted for 7 days (FIG. 13), whereas ZT-1a-treated mice showed reduced unidirectional turn preference and absence of asymmetries by day 7 post-stroke. In the adhesive contact and removal tests that evaluate fine sensorimotor function deficits (Begum et al. (2018) Glia 66, 126-144), ZT-1a-treated mice displayed a trend to faster contact response than in vehicle-control mice (although short of statistical significance; p=0.10), and significantly improved motor function (p<0.05). These data show that post-stroke treatment with ZT-1a in mice significantly improved neurological functional recovery.

Referring to FIG. 13, neurological deficit scores, corner tests, and adhesive tape contact and adhesive tape removal tests of mice treated with vehicle or ZT-1a 1 day before tMCAO (−1) and at days 0, 1, 3, 5, and 7 post-tMCAO are shown. Vehicle (DMSO, 2 ml/kg) or ZT-1a (5.0 mg/kg) were administered as described in B. Data are means±SEM, n=6 for each group (male 3, female 3). * p<0.05 vs. vehicle.

i. ZT-1a Inhibits Stroke-Induced SPAK-NKCC1 Phospho-Activation in Ischemic Brains.

Figure 14A:
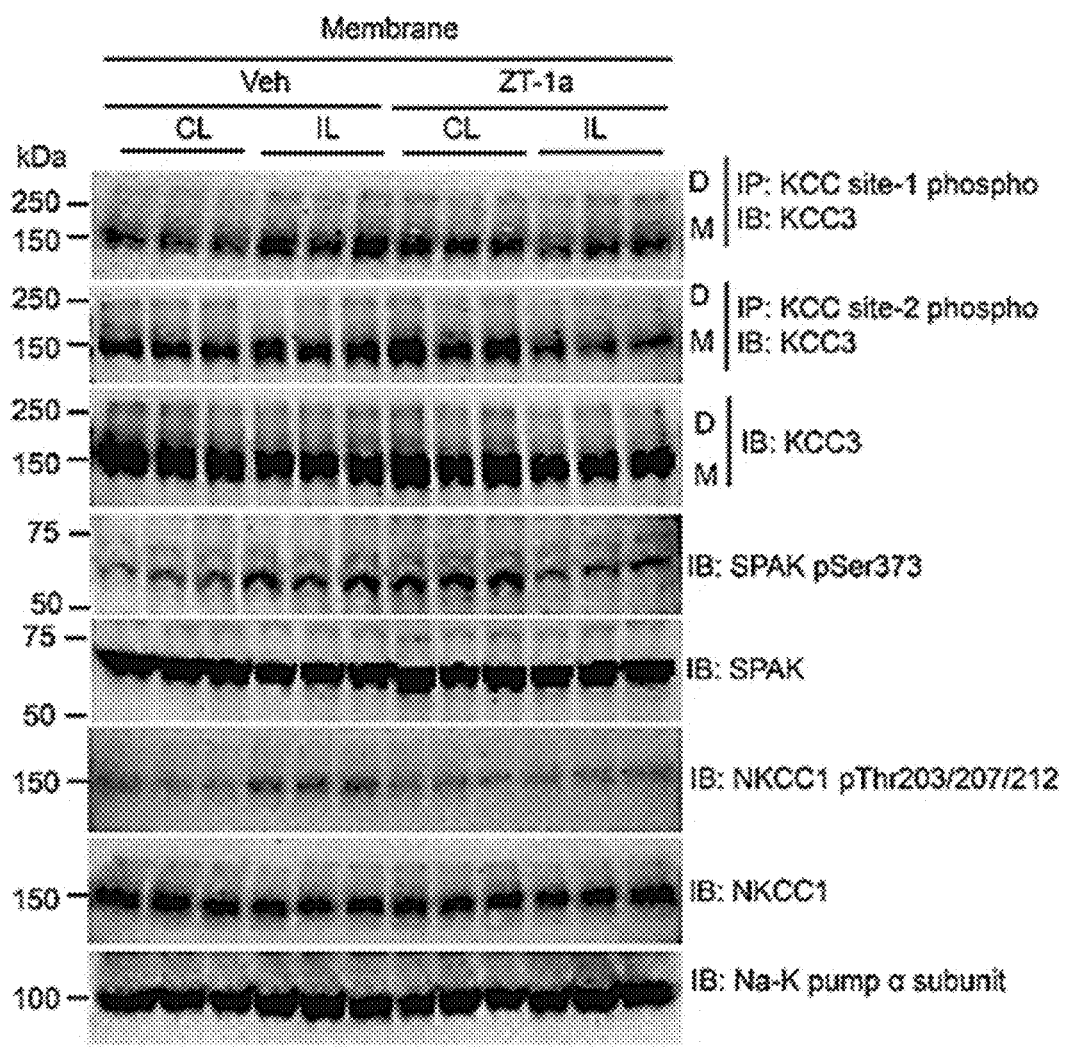
FIG. 14A and FIG. 14B show representative data demonstrating that ZT-1a decreases ischemia-induced SPAK, NKCC1, and KCC3 phosphorylation in the cerebral cortex post-stroke.
Figure 14B:
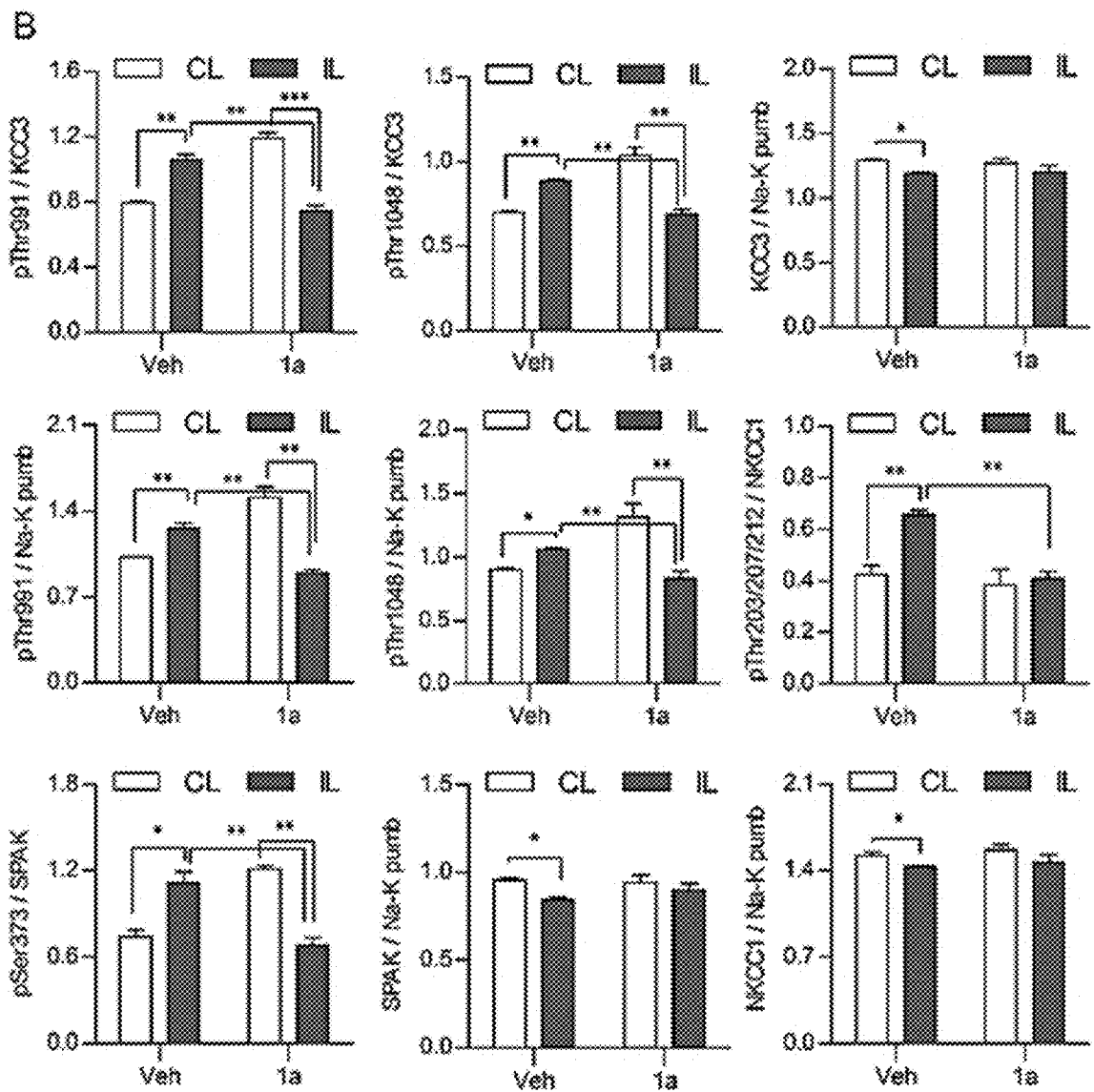

Next, the effect of ZT-1a on SPAK/OSR1, NKCC1, and KCC3 phosphorylation in ischemic mouse brains was tested. Ischemic stroke increased phosphorylation of pSPAK (pSer373)/pOSR1 (pSer325) ~1.5 fold (p<0.05), pNKCC1 (pThr203/207/212) ~1.6 fold (p<0.05), and pKCC3 pThr991 (p<0.05) and pThr1048~1.3-fold (both p<0.05) in membrane fractions from the ipsilateral (IL) cortical hemisphere at 24 hrs reperfusion in vehicle-control treated mice, without change in levels of corresponding total proteins (FIG. 14A and FIG. 14B). Post-stroke administration of ZT-1a in mice prevented ischemia-induced increases of pSPAK/pOSR1, pNKCC1, and pKCC3 without affecting corresponding total protein expression (p<0.05) (FIG. 14A and FIG. 14B). Without wishing to be bound by theory, these results indicate that ZT-1a inhibits SPAK-dependent phospho-stimulation of NKCC1 and inactivation of KCC3 in ischemic brains.

Referring to FIG. 14A, representative immunoblots (IB) of phospho-SPAK/OSR1 (pSPAK/pOSR1), phospho-KCC3 and phospho-NKCC1 (pNKCC1) in mouse brains studied 24 hrs post-reperfusion after ischemic stroke are shown. Membrane protein fractions were prepared from contralateral (CL) and ipsilateral (IL) cerebral hemispheres. Vehicle (Veh, DMSO) or ZT-1a (5 mg/kg) was administered as described in FIG. 11A, FIG. 11B, and FIG. 13. Na$^+$—K$^+$ ATPase α-subunit and GAPDH served, respectively, as loading controls for membrane and cytosol fractions.

Referring to FIG. 14B, densitometry analyses of immunoblots (similar to those in panel A) of pSPAK/pOSR1, pNKCC1, tSPAK/tOSR1, and tNKCC1 in mouse brains studied 24 hrs reperfusion after tMCAO are shown. Data are means±SEM, n=5 per group (male 3, female 2). *p<0.05.

j. ZT-1a-Treated Mice Exhibited Persistent Protection of Grey and White Matter after Ischemic Stroke.

Figure 15A:
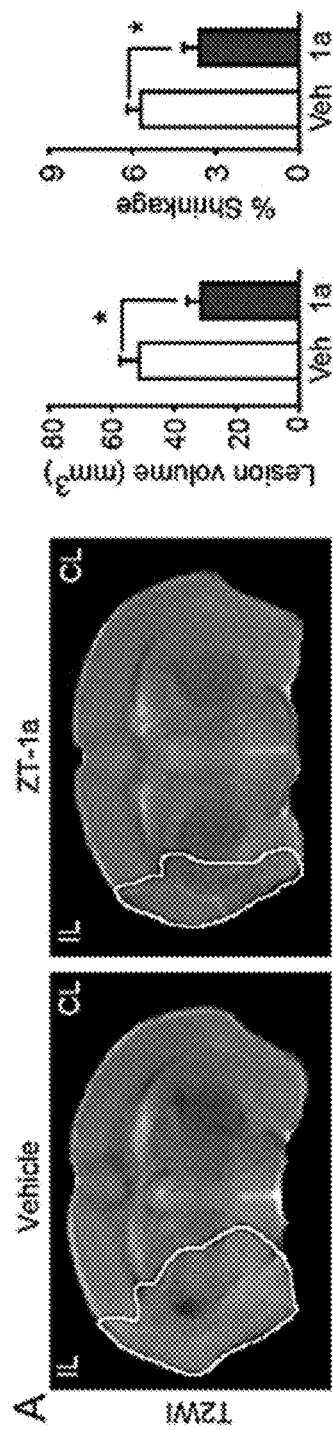
FIG. 15A and FIG. 15B show representative data demonstrating that ZT-1a reduces subacute brain gray and white matter injuries after ischemic stroke.

Ex vivo MRI studies of brains from vehicle-control and ZT-1a-treated mice at 7 days post-stroke were also conducted. T2-weighted MRI analysis further confirmed that ZT-1a treatment reduced stroke-induced lesion volume by ~40% and brain atrophy (hemisphere shrinkage) by ~41% (p<0.05; FIG. 15A). To assess the effect of ZT-1a on stroke-mediated white matter injury, we analyzed fractional anisotropy (FA), axial diffusivity (AD), radial diffusivity (RD) and mean diffusivity (MD) and directionally encoded color (DEC) maps of the corpus callosum (CC) and external capsule (EC) in vehicle-control and ZT-1a-treated brains. Representative images of DEC and FA maps (FIG. 15B) reveal intact CC and EC (arrows) in the CL hemisphere and injured EC in the IL hemisphere (arrowheads). Whereas FA values were reduced in the ipsilateral EC tract of the vehicle-control group, indicating loss of white matter integrity in subacute stroke brains. In contrast, EC tract FA values in the IL hemisphere of ZT-1a-treated mice did not change (p>0.05), reflecting preserved EC white matter microstructure. These results further suggest that post-stroke treatment with ZT-1a provides robust neuroprotection of both gray and white matter in ischemic brains.

Referring to FIG. 15A, representative T2WI images and quantitative analyses of lesion volume and atrophy (shrinkage) of ex vivo brains from vehicle (Veh) control and ZT-1a-treated mice at 7 days post-MCAO are shown. Vehicle (DMSO 2 ml/kg) or ZT-1a (5.0 mg/kg) was administered i.p. in divided doses at 3 and 8 hrs after reperfusion. Data are means±SEM, n=6 per group (male 3, female 3); * p<0.05.

Figure 15B:
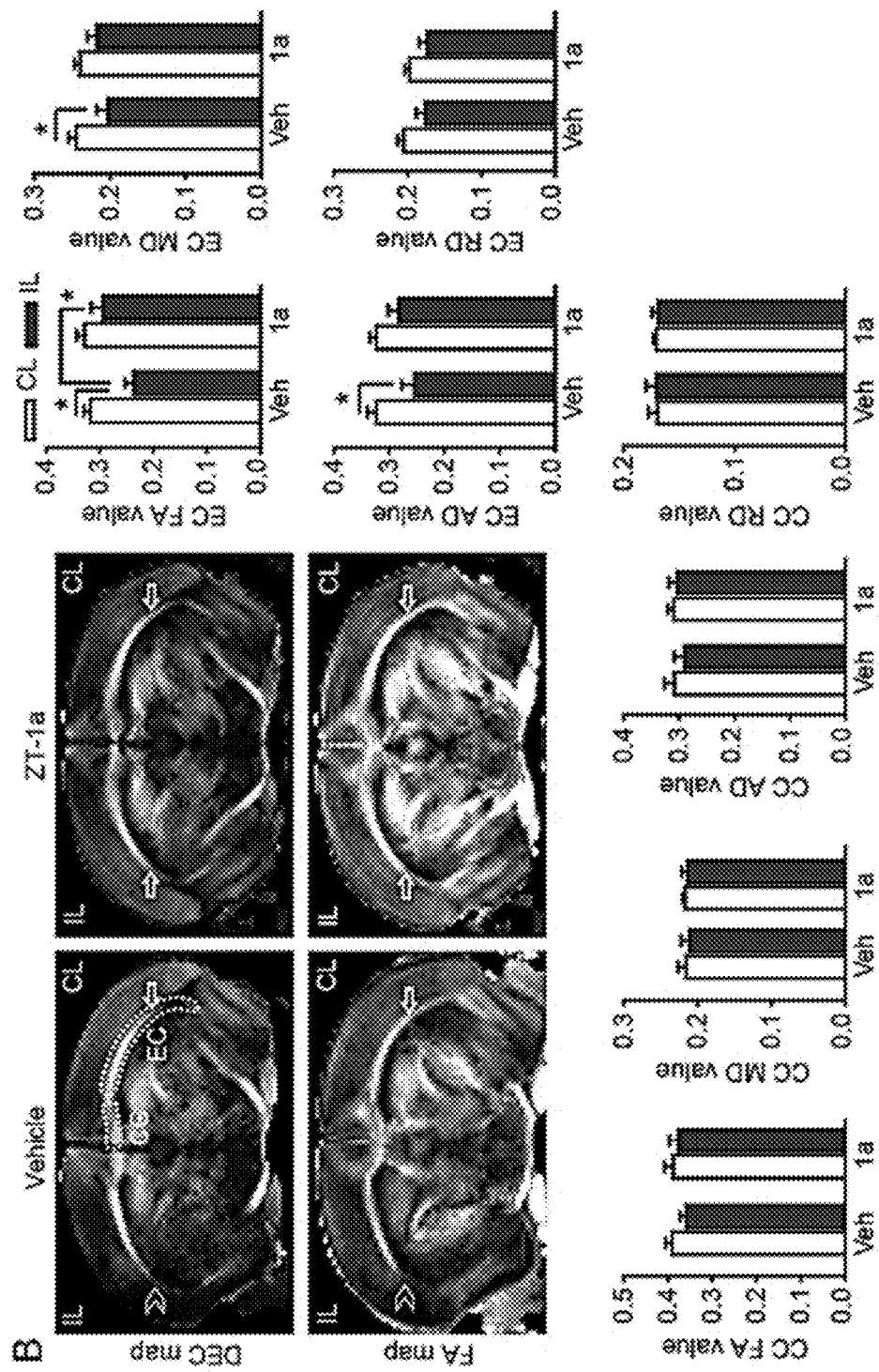

Referring to FIG. 15B, representative images of directionally encoded color (DEC) and fractional anisotropy (FA) maps are shown. Arrow: EC (external capsule); double arrowhead: damaged EC; CC: corpus callosum. Bar graphs display quantitation of mean values of FA, mean diffusivity (MD), axial diffusivity (AD) and radial diffusivity (RD) of white matter tissues (CC or EC) of ex vivo brain from vehicle control (Veh) and ZT-1a-treated mice at 7 days post-MCAO. Same cohort as A. Data are means±SEM, n=6 per group (male 3, female 3); * p<0.05.

k. ZT-1a is Superior to Closantel and to WNK463 in Reducing Ischemic Brain Injury in Mice.

Figure 16A:
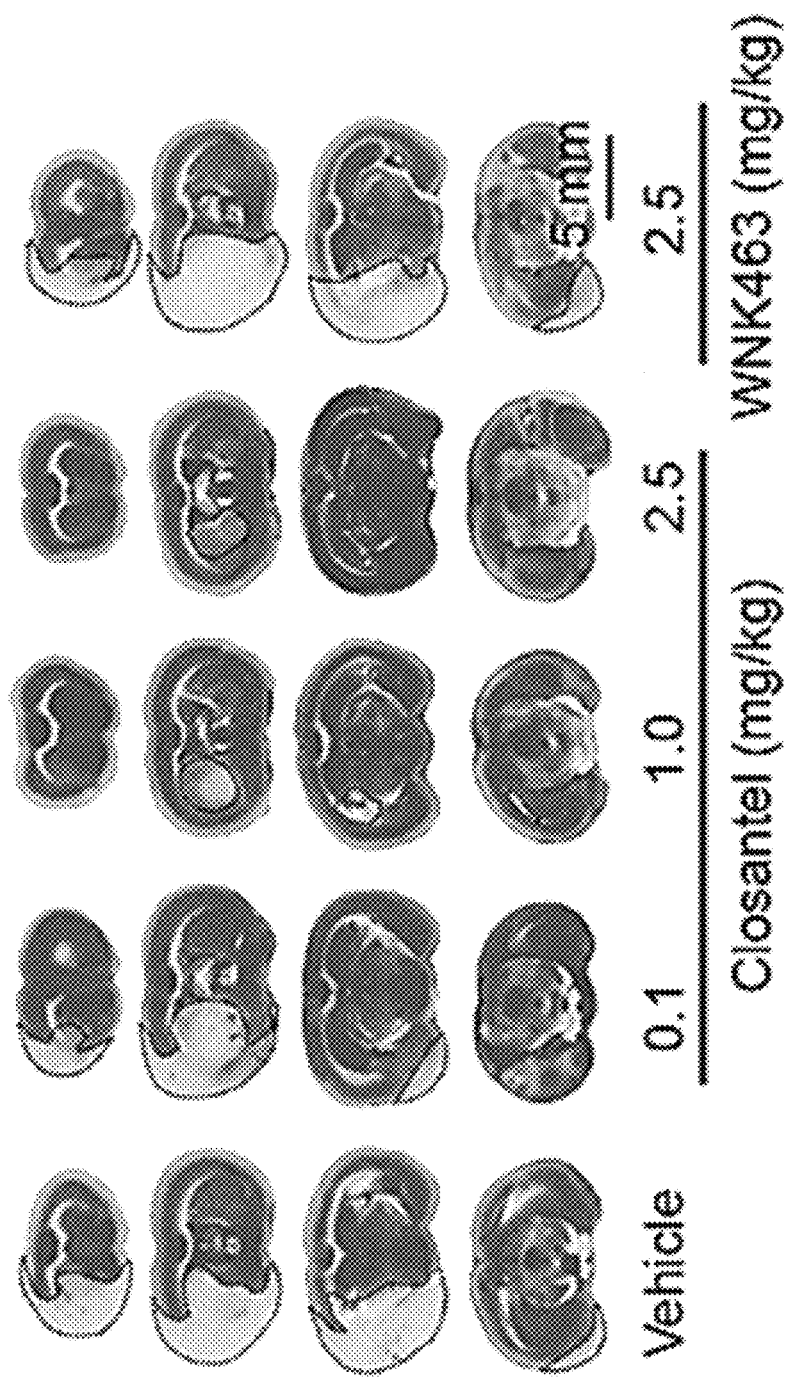
FIG. 16A-C show representative data illustrating that post-stroke administration of SPAK inhibitor Closantel exhibits dose-dependent neuroprotective effects.
Figures 16B, 16C:
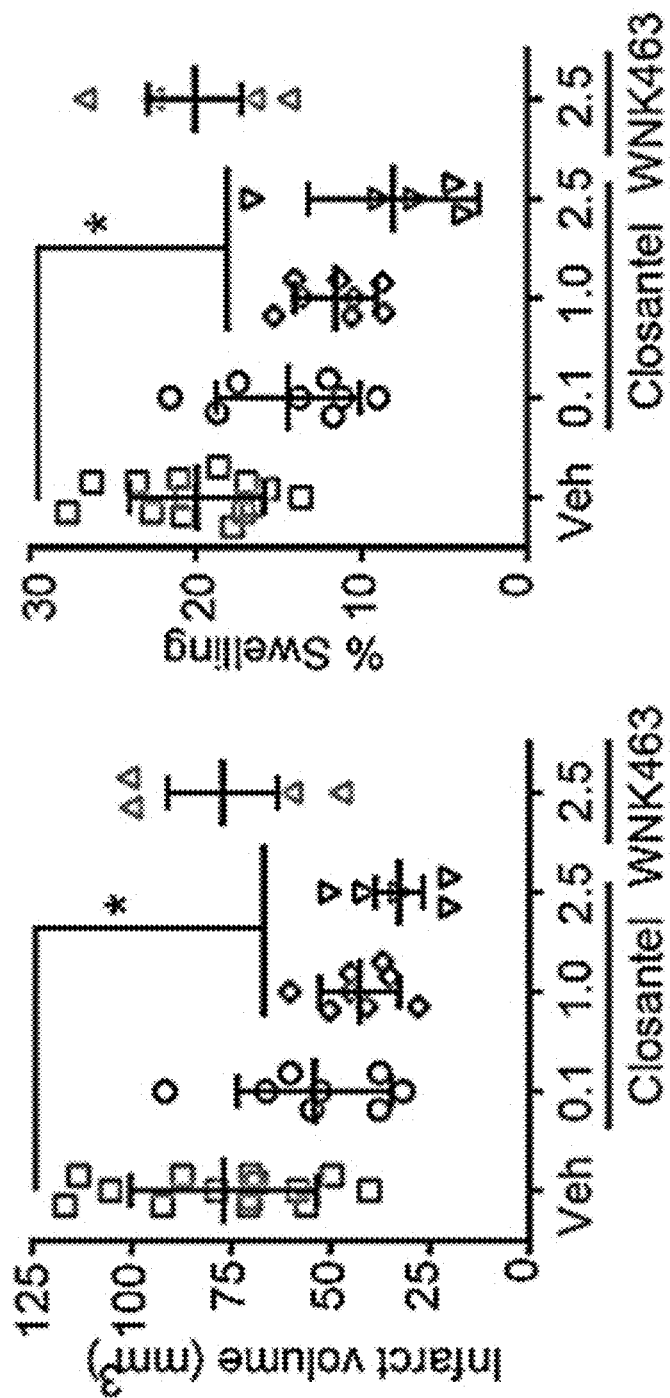
Figure 17A:
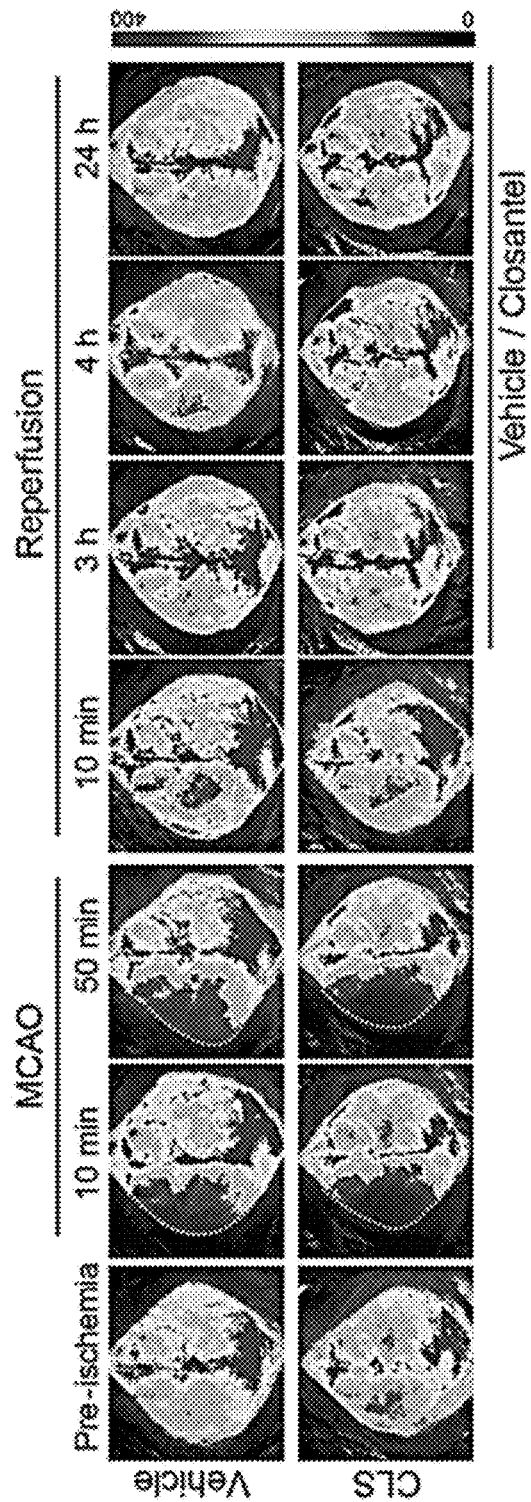
FIG. 17A-C show representative data illustrating that post-stroke administration of ZT-1a or Closantel does not affect regional cerebral blood flow (rCBF) in ischemic mice.
Figure 17C:
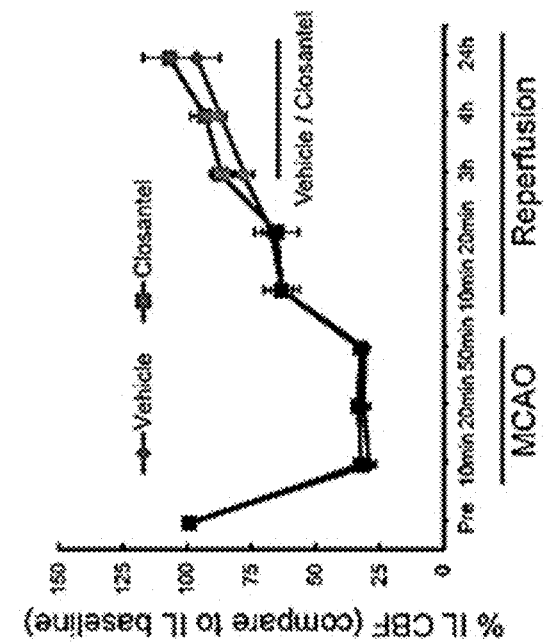
Figure 17B:
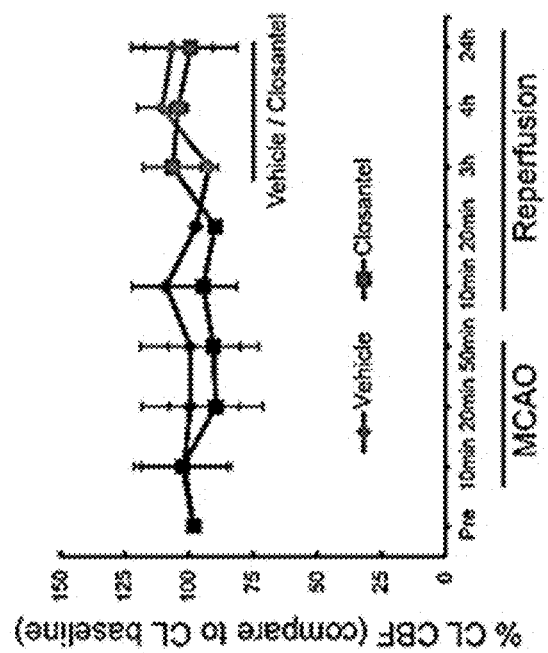

Post-stroke neuroprotective efficacy of Closantel and the pan-WNK-kinase inhibitor WNK463 were compared. Administration of Closantel (1.0 or 2.5 mg/kg) at 3 hr and at 8 hr reperfusion dose-dependently reduced infarct volume and hemispheric swelling (p<0.05, FIG. 16A-C), whereas the 0.1 mg/kg dose of Closantel was ineffective. Closantel, like ZT-1a, had no effects on rCBF (FIG. 12A-C and FIG. 17A-C). In contrast, WNK463 treatment (2.5 mg/kg) reduced neither infarct volume nor hemispheric swelling at 24 hr reperfusion (FIG. 16A-C). These data display superiority of ZT-1a to WNK463 and Closantel for in vivo inhibition of the WNK-SPAK-CCC pathway in the mouse model of ischemic brain injury.

5. Novel SPAK Kinase Inhibitor ZT 1a is Neuroprotective in Mouse Model of Malignant Ischemic Stroke In sum, a potent and selective inhibitor of SPAK kinase, ZT-1a [5-chloro-N-(5-chloro-4-((4-chlorophenyl)(cyano) methyl)-2-methylphenyl)-2-hydroxybenzamide] has been discovered and characterized through a "scaffold-hybrid" strategy. ZT-1a inhibits stimulatory phosphorylation of SPAK Ser373 and NKCC1 Thr203/207/212, and inhibitory phosphorylation of the KCCs (e.g., KCC3 Thr991/Thr1048) at a concentration of 3 µM in HEK293 cells to effectively promote cellular Cl⁻ extrusion. ICV delivery of ZT-1a in rats normalizes CSF hypersecretion in experimental hemorrhagic hydrocephalus by decreasing inflammation-dependent phosphorylation of SPAK, NKCC1, and KCC4. Systemic administration of ZT-1a in mice after ischemic stroke attenuates cerebral edema and improves neurological outcomes by reducing ischemia-induced phosphorylation of NKCC1 and KCC3. Without wishing to be bound by theory, these data suggest ZT-1a is a novel effective kinase-cotransporter modulator that restores brain water homeostasis and improves neurological function in vivo.

NKCC1 is potently inhibited by the commonly used loop diuretics bumetanide and furosemide. Furosemide has poor blood-brain barrier (BBB) penetration and significantly lowers NKCC1 affinity than bumetanide (Donovan et al. (2016) European journal of pharmacology 770, 117-125; Fischer et al. (1998) J Membrane Biol 165, 201-211; Puskarjov et al. (2014) Epilepsia 55, 806-818). Multiple studies in both animal models and humans suggest bumetanide is effective in reducing Cl⁻ influx and restoring GABAergic inhibition (Dzhala et al. (2010) The Journal of neuroscience: the official journal of the Society for Neuroscience 30, 11745-1176; Kahle et al. (2009) Journal of child neurology 24, 572-576; Liu et al. (2012) Pediatric research 71, 559-565; Mazarati et al. (2009) Epilepsia 50, 2117-2122). However, bumetanide exhibits poor CNS penetration due to its significant binding to serum albumin, and its inhibition of the renal-specific isoform NKCC2 causes potent, use-limiting diuresis, an off-target for treating brain disorders. In addition, bumetanide usage in neonates has raised concerns that altering premature $E_{GABA}$ depolarization by bumetanide may inhibit normal neurodevelopment (Wang and Kriegstein (2011) Cerebral cortex 21, 574-587). Alternatively, studies have demonstrated the potential of KCC2 activators as effective pharmacotherapies for disorders of GABAergic disinhibition (Austin and Delpire (2011) Anesth Analg 113, 1509-1515). CLP257 was reported as a direct KCC2 activator (Gagnon et al. (2013) Cell physiology 304, C693-714); however, these results have recently been challenged (Cardarelli et al. (2017) Nature medicine 23, 1394-1396).

Problems associated with directly targeting NKCC or the KCCs were circumvented by focusing on the upstream SPAK kinase that reciprocally stimulates NKCC1 and inhibits KCCs through phosphorylation at a shared motif. The strategy of targeting the ATP-binding site of SPAK/OSR1 raises concern regarding the ability to develop sufficiently selective inhibitors that do not suppress other kinases. The introduction of STOCK1S-50699 and STOCK2S-26016 (Mori et al. (2013) The Biochemical journal 455, 339-345) has highlighted the possibility of developing additional inhibitors of SPAK signaling which target the CCT domain rather than the kinase domain. In vitro studies, however, demonstrated that only STOCK1S-50699, but not STOCK2S-26016, suppressed phosphorylation of SPAK/OSR1 and NKCC1 induced by hypotonic low [Cl⁻] (de Los Heros et al. (2014) The Biochemical journal 458, 559-573), and further showed unfavorable in vivo pharmacokinetics of STOCK1S-50699 (data not shown). The anti-parasitic drug Closantel, widely used in livestock (Swan (1999) J S Afr Vet Assoc 70, 61-70), emerged as the first candidate drug for in vivo pharmacological inhibition of SPAK (Alamri et al. (2017) ChemMedChem 12, 639-645; Kikuchi et al. (2015)

Journal of the American Society of Nephrology: JASN 26, 1525-1536), but contraindicated in humans (Tabatabaei et al. (2016) BMC Ophthalmol 16, 207), The ATP-independence of SPAK inhibition by Closantel and STOCK1S-14279 has introduced the possibility of developing inhibitors of WNK signaling by binding to constitutively active or WNK-insensitive (T233E) SPAK (Kikuchi et al. (2015) Journal of the American Society of Nephrology: JASN 26, 1525-1536). Through "scaffold-hybrid" strategy (Deng et al. (2011) Nature chemical biology 7, 203-205; Deng et al. (2013) Eur J Med Chem 70, 758-767), a new focused chemical library derived from these two ATP-insensitive inhibitors was designed and synthesized (FIG. 1A). ZT-1a was screened and characterized as one of the best SPAK inhibitor compounds (Table 1) from a chemical library of ~300 compounds, through fluorescence polarization assays, in vitro SPAK kinase assays, and cell-based assays. ZT-1a was more potent as a general CCC inhibitor than the previously existing SPAK inhibitors Closantel (Kikuchi (2015) Nihon Jinzo Gakkai shi 57, 1319-1322), Rafoxanide ((Alamri et al. (2017) ChemMedChem 12, 639-645), STOCK1S-14279 (Kikuchi (2015) Nihon Jinzo Gakkai shi 57, 1319-1322), and STOCK1S-50669 (Mori et al. (2013) The Biochemical journal 455, 339-345), substantially inhibited phosphorylation of SPAK Ser373, NKCC1 Thr203/207/212, KCC2 Thr906 and Thr1007 (KCC4 Thr926 and Thr980) at a concentration of 3 µM in HEK293 cells, and effectively promoted cell Cl extrusion.

In a mouse study, post-stroke administration of Closantel reduced ischemic cerebral infarction and swelling in a dose-dependent manner. However, adverse effects in humans at higher doses (~25 mg/kg), including weakness, visual impairment and blindness (Essabar et al. (2014) Asia Pacific Journal of Medical Toxicology 3, 173-175; Tabatabaei et al. (2016) BMC Ophthalmol 16, 207) deterred further investigation of Closantel in the setting of stroke or hydrocephalus. The pan-WNK-kinase inhibitor WNK463 inhibits all four WNK kinases in the nanomolar range in vitro and was developed as an anti-hypertensive drug (Yamada et al. (2016) Nature chemical biology 12, 896-898). Oral administration of 1-10 mg/kg WNK463 reduced blood pressure and regulated body fluid and electrolyte homeostasis in normotensive and hypertensive rodent models (Yamada et al. (2016) Nature chemical biology 12, 896-898). However, WNK463 administered to mice at 2.5 mg/kg dose showed no neuroprotective effects, instead inducing ataxia and breathing difficulties which are similar to the previous report at 1-10 mg/kg doses (Yamada et al. (2016) Nature chemical biology 12, 896-898). The causes for these adverse effects remain unclear, but they, too, discouraged efficacy testing of WNK463 at higher doses.

Post-stroke administration of ZT-1a attenuated stroke-associated infarction and cerebral edema and rapidly improved neurological function in post-ischemic mice, results corroborated by brain MRI. T2-weighted MRI of ex vivo brains from ZT-1a-treated mice showed smaller lesion volumes, and reduced brain atrophy at 7 days post-stroke. DTI data analysis revealed that ZT-1a significantly reduced subacute brain white matter injury after ischemic stroke. ZT-1a thus provides neuroprotection, at least in part, by directly inhibiting SPAK kinase activity and SPAK-mediated phospho-activation of NKCC1 and inactivation of KCC3 in ischemic brains. ZT-1a reduced ischemia-induced elevations of pSPAK and pNKCC1 by 55-65%, and elevations of pKCC3 by 30% compared to vehicle-control mice. The findings that ZT-1a concurrently inhibited phosphorylation of SPAK, KCC3 and NKCC1 are consistent with this interpretation, i.e., ZT-1a-mediated allosteric inhibition of SPAK kinase activity is likely through binding to the secondary pocket of the CCT domain, preventing SPAK binding and activation by upstream WNK kinases. A similar dual mechanism of WNK-SPAK inhibitor STOCK1S-50669 has been reported in cultured cells (Alamri et al. (2017) ChemMedChem 12, 639-645; Mori et al. (2013) The Biochemical journal 455, 339-345).

Plasma half-life of ZT-1a is only ~1.8 hrs in normal naïve mice, and ZT-1a apparently fails to penetrate the healthy BBB. However, ZT-1a appeared to more effectively enter the ischemic brain across its leaky BBB in exerting its neuroprotective effects. Ischemic stroke injury increases permeability and disrupts BBB tight junctions as early as at 30 minutes of reperfusion, (Sandoval and Witt (2008) Neurobiol Dis 32, 200-219; Shi et al. (2016) Nat Commun 7, 10523), which facilitates brain access for small molecule drugs (Won et al. (2011) Exp Mol Med 43, 121-128). ZT-1a was administered with the initial dose at 3 hrs post stroke, a time is comparable to effective treatment windows for other potential neuroprotective candidates, such as glibenclamide, human albumin, and minocycline (at 2.5-4.0 hrs post-stroke) (Belayev et al. (2001) Stroke 32, 553-560; Simard et al. (2009) Lancet Neurol 6, 258-268; Yrjanheikki et al. (1999) Proc Natl Acad Sci USA 96, 13496-13500). ZT-1a is superior to the anti-parasitic drug Closantel and the novel pan-WNK inhibitor WNK463 in reducing ischemic brain damage. Future investigations are needed for examining bioavailability and pharmacokinetics of ZT-1a in ischemic brains and optimizing treatment protocols.

The CPe secretes higher volumes of fluid (CSF) per cell than any other epithelium (500 ml/day). NKCC1 expressed in the apical CPe contributes approximately half of the CSF production via its unusual outward transport direction and its unique ability to directly couple water transport to ion translocation (Steffensen et al. (2018) Nat Commun 9, 2167). In a rat model of hemorrhagic hydrocephalus, intraventricular hemorrhage causes a Toll-like receptor 4 (TLR4)- and NF-κB-dependent inflammatory response in CPe associated with ~3-fold increased bumetanide-sensitive CSF secretion (Karimy et al. (2017) Nature medicine 23, 997-1003). IVH-induced hypersecretion of CSF is mediated by TLR4-dependent activation of SPAK, which binds, phosphorylates, and stimulates NKCC1 at the CPe apical membrane (Karimy et al. (2017) Nature medicine 23, 997-1003). Genetic depletion of TLR4 or SPAK normalizes hyperactive CSF secretion rates and reduces posthemorrhagic hydrocephalus symptoms by reducing NKCC1 phosphorylation. Here, it was shown that ICV administration of ZT-1a restores CSF secretion rates to basal levels after IVH and antagonizes inflammation-induced phosphorylation of SPAK, NKCC1, and KCC4 in CPe. Without wishing to be bound by theory, this suggests that ZT-1a could be a novel pharmacological treatment for hydrocephalus, currently treatable only by the highly morbid surgical approaches of endoscopy or shunting. Further work will be required to assess the therapeutic potential of ZT-1a in other pre-clinical models of hydrocephalus.

In sum, the novel drug, ZT-1a, that potently and selectively inhibits SPAK kinase, the master regulator of CCCs, was developed. ZT-1a promotes cellular Cl⁻ extrusion by simultaneous reduction of SPAK-dependent NKCC1 stimulatory phosphorylation and KCC inhibitory phosphorylation. Intracerebroventricular delivery of ZT-1a, by decreasing inflammation-induced NKCC1/KCC4 phosphorylation in the choroid plexus, normalizes CSF hypersecretion in hemorrhagic hydrocephalus. Systemically administered ZT-1a, by reducing ischemia-induced NKCC1/KCC3 phosphorylation, attenuates cerebral edema, protects against brain damage, and improves neurological outcomes after ischemic stroke. Without wishing to be bound by theory, these results suggest ZT-1a is an effective kinase-cotransporter modulator with therapeutic potential for disorders of impaired brain water homeostasis.

6. Therapeutic Application of ZT-1a and Derivatives Thereof for Brain Disorders a. ZT-1a Penetrates Ischemic Brain of Normotensive Mice Brain penetration of ZT-1a was examined in normotensive mice after ischemic stroke due to leaky BBB. ZT-1a was administered by a single injection of 5 mg/kg ZT-1a (i.p.) in normotensive sham-control mice or in the mice at 3 hrs after tMCAO. At 2 hrs post-injection, there was no significant difference in the plasma bioavailability of ZT-1a in sham control mice and ischemic stroke mice (p=0.29; n=10-11). However, brain concentrations of ZT-1a were significantly higher (~1.8-fold; p=0.006; n=10-11) in the stroke mice than that of sham-controls. These studies suggest that ischemic stroke facilitates ZT-1a penetration into brain tissue, probably via the disrupted blood-brain barrier (BBB).

b. Both Male and Female Ang II-Mediated Hypertensive Mice are Responsive to SPAK Inhibitor ZT-1a after pdMCAO.

Ang II infusion (osmotic minipump at 1000 ng/kg/min, s.c.) for 14 days significantly elevated arterial BP in male mice. In contrast, 14-day infusion of Ang II in female mice did not increase systemic BP, which is consistent with published reports on estrogen-mediated effects (Xue et al. (2005) *Am J Physiol Heart Circ Physiol.* 288:H2177-2184). These mice were randomly subjected to pdMCAO and post-stroke administration of DMSO vehicle (Veh) control or the novel SPAK inhibitor ZT-1a (2.5 mg/kg, i.p., with an initial dose at 3 hrs and the second dose at 8 hrs after pdMCAO). Ang II-infused mice (both male and female) exhibited significantly larger infarct volume and hemispheric swelling at 24 hrs after pdMCAO, compared to saline-infused normotensive controls. Post-stroke administration of the novel SPAK inhibitor ZT-1a decreased infarct volume (~50%) and hemispheric swelling (~50%) in the Ang II-infused mice (male or female) compared to Veh control.

Figures 18A, 18B:
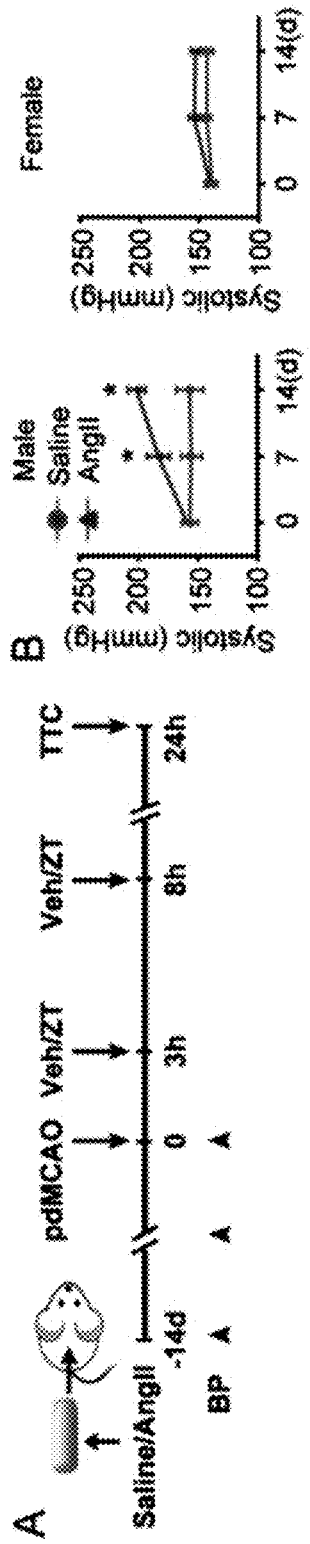
FIG. 18A-E show representative data illustrating that both male and female Angotension II-induced hypertensive mice are responsive to SPAK inhibitor ZT-1a after permanent middle cerebral artery occlusion model (pdMCAO).

Referring to FIG. 18A, Angotension II (Ang II) infusion (osmotic minipump at 1000 ng/kg/min, s.c.) for 14 days in both male or female mice significantly elevated arterial BP in male mice. In contrast, 14-day infusion of Ang II in female mice did not increase systemic BP (FIG. 18B), which is consistent with published reports on estrogen-mediated effects. These mice were randomly subjected to pdMCAO and post-stroke administration of DMSO vehicle (Veh) control or the novel SPAK inhibitor ZT-1a (2.5 mg/kg, i.p., with an initial dose at 3 hrs and the second dose at 8 hrs after pdMCAO).

Figure 18C:
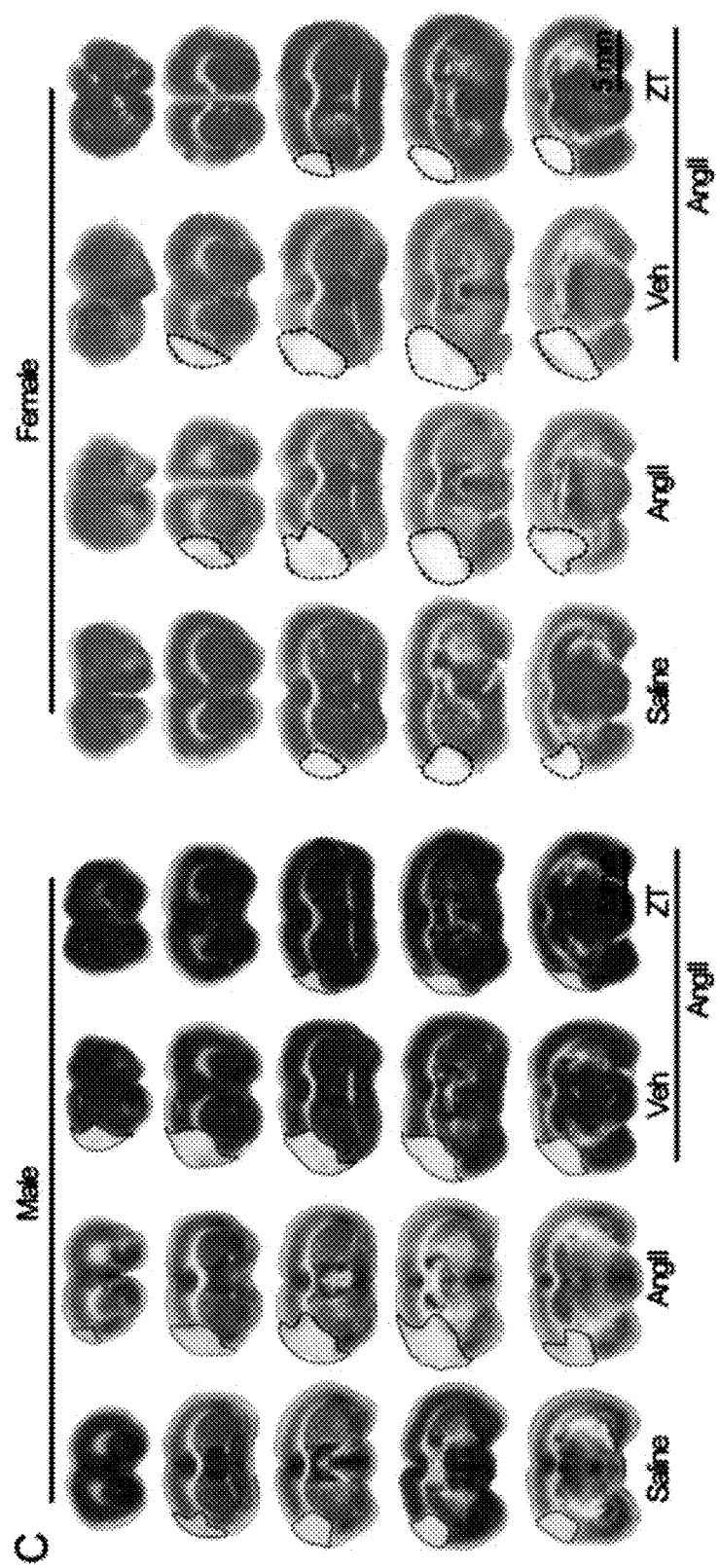
Figures 18D, 18E:
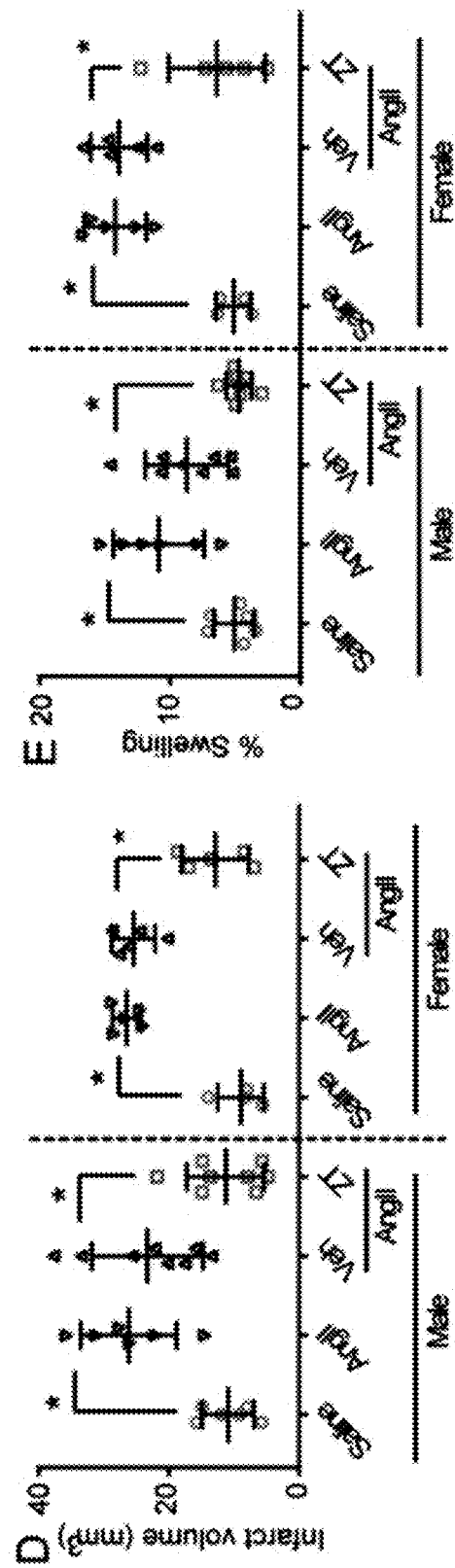

Referring to FIG. 18C-E, Ang II-infused mice (both male and female) exhibited significantly larger infarct volume and hemispheric swelling at 24 hrs after pdMCAO, compared to saline-infused normotensive controls. Post-stroke administration of the novel SPAK inhibitor ZT-1a decreased infarct volume (~50%) and hemispheric swelling (~50%) in the Ang II-infused mice (male or female, FIG. 18C-E), compared to Veh control.

These findings demonstrate that female mice are equally sensitive to ZT-1a treatment, despite the absence of elevated BP. Moreover, without wishing to be bound by theory, these findings further support the view that Ang II-mediated activation of WNK-SPAK-NKCC1 signaling occurs in the CNS of both male and female mice, and ZT-1a effects are via blocking the WNK-SPAK-NKCC1 complex in ischemic brains, unlikely through reducing systemic BP.

c. Post-Stroke Administration of SPAK Inhibitor ZT-1a Improves Neurological Deficits in the Ang II-Mediated Hypertensive Mice after pdMCAO.

Figure 19A:
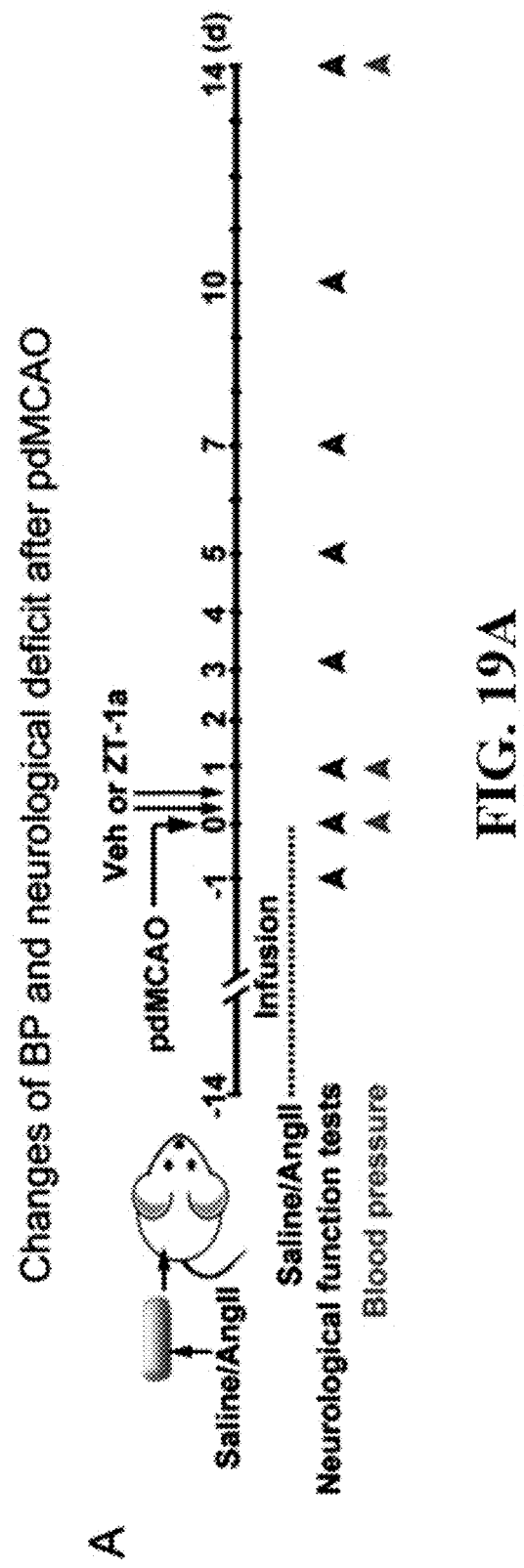
FIG. 19A-E show representative data illustrating changes in blood pressure (BP) and neurological deficit after pdMCAO.
Figures 19B, 19C, 19D:
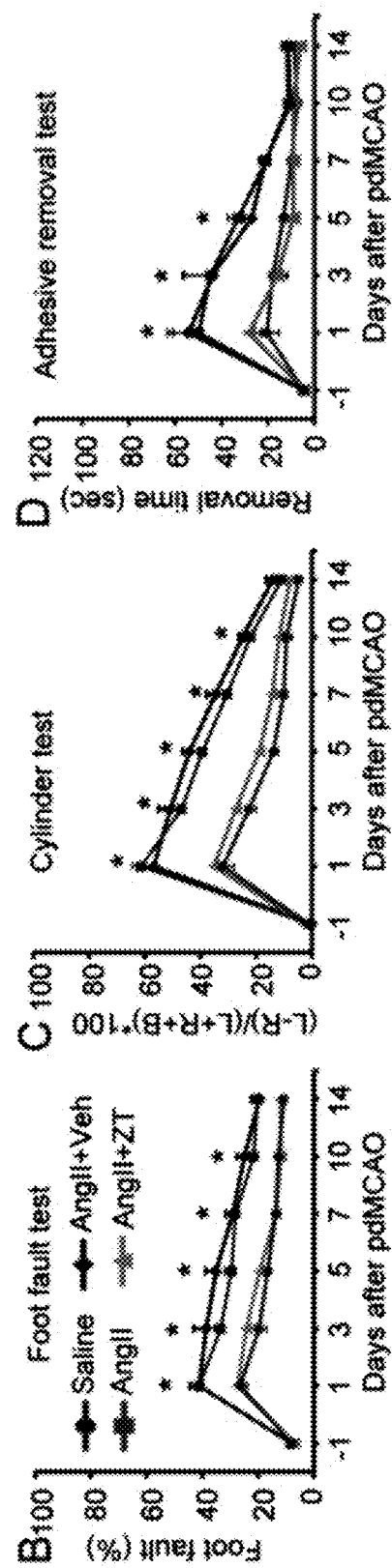

Sensory-motor function was assessed in the Ang II-mediated HTN mice (male) at 1-14 days post-pdMCAO (FIG. 19A). Ang II-mediated HTN mice (Ang II alone, or Ang II+Veh treatment) exhibited worsened neurological function following pdMCAO, compared to the saline-infused normotensive control group, in foot fault test (FIG. 19B), cylinder test (FIG. 19C), and adhesive tape removal test (FIG. 19D). In contrast, ZT-1a-treated hypertensive mice displayed less foot faults, less unilateral turns and better performance in adhesive tape removal from the injured paws (FIG. 19B-D).

Figure 19E:
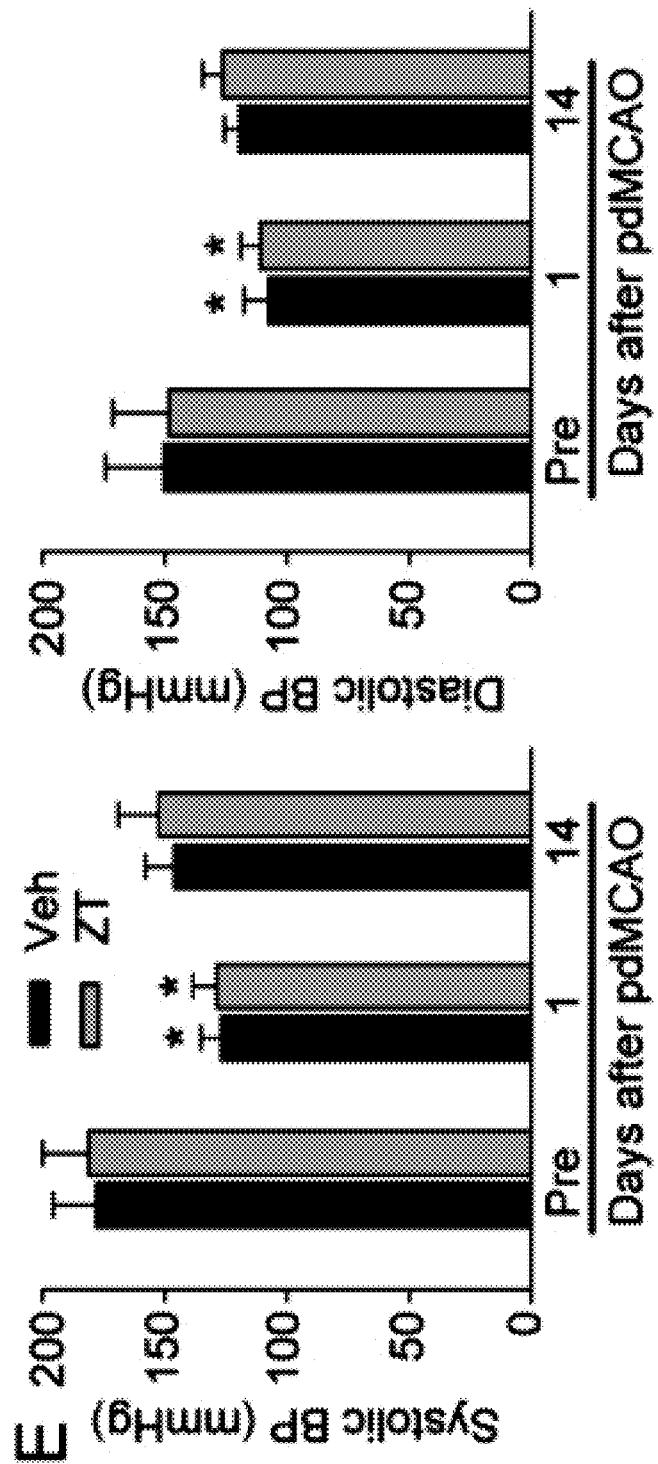

To determine whether SPAK inhibitor ZT-1a treatment affected BP, systemic BP was measured in ZT-1a-treated mice after pdMCAO. FIG. 19E shows that ischemic stroke significantly lowered BP in mice at 1 day pdMCAO. But, Veh- and ZT-1a-treated mice displayed similar systolic and diastolic BP at 1 or 14 days after pdMCAO.

These findings suggest again that neuroprotective effects conferred by ZT-1a in hypertensive mice following pdMCAO is BP-independent. These data clearly show that Ang II-mediated HTN mice exhibited worsened ischemic infarction and neurological deficits after pdMCAO. Post-stroke inhibition of SPAK kinase with a novel SPAK inhibitor ZT-1a provided robust neuroprotection against ischemic stroke-induced brain damage and accelerated neurological recovery.

Cylinder Test:

Mice are placed in a transparent cylinder (9 cm in diameter and 15 cm in height) for 10 min and all the forelimb movements of the mice will be recorded. Forepaw (left/right/both) usage on initial contact against the cylinder wall after rearing and during lateral exploration will be recorded. Prior to ischemic stroke, animals were placed in the cylinder for 5 min to establish a baseline symmetry profile.

Foot Fault Test:

Each mouse will be placed on a stainless-steel grid floor (20 cm×40 cm with a mesh size of 4 $cm^2$) elevated 1 m above the floor. The animals will first be habituated to the grid floor for 1 min and then tested for three 1-min trials. Data will be expressed as the number of foot fault errors made by the forelimbs contralateral to the injury hemisphere as a percentage of total steps.

Adhesive Contact and Removal Tests:

A piece of adhesive tape (4 mm×3 mm) will be attached to the contralateral forepaw with equal pressure by the experimenter in each trial. The time to make first contact with the tape and the time to remove the tape will be recorded as the contact time and the removal time, respectively. Each trial ends after the adhesive tape is removed or after 2 min elapse.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

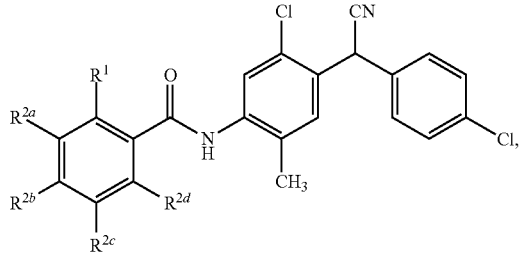

wherein $R^1$ is selected from —$SR^{20}$ and —$NR^{21a}R^{21b}$;
  wherein $R^{20}$, when present, is selected from hydrogen and C1-C4 alkyl;
  wherein each of $R^{21a}$ and $R^{21b}$, when present, is independently selected from hydrogen and C1-C4 alkyl;
wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino,
provided that when $R^1$ is —OH then $R^{2e}$ is hydrogen, and
provided that when $R^{20}$ is C1-C4 alkyl then at least two of $R^{2a}$, $R^{2b}$, $R^{2c}$, and $R^{2a}$ are not hydrogen,
or a pharmaceutically acceptable salt thereof.

2. The compound of claim 1, wherein $R^1$ is —$SR^{20}$.

3. The compound of claim 2, wherein $R^1$ is —SH.

4. The compound of claim 1, wherein $R^1$ is —$NR^{21a}R^{21b}$.

5. The compound of claim 1, wherein each of $R^{2a}$, $R^{2b}$, $R^{2c}$, and $R^{2d}$ is hydrogen.

6. The compound of claim 1, wherein each of $R^{2b}$ and $R^{2d}$ is hydrogen.

7. The compound of claim 1, wherein each of $R^{2a}$ and $R^{2c}$ is not hydrogen.

8. The compound of claim 1, wherein at least one of $R^{2a}$ and $R^{2c}$ is not hydrogen.

9. The compound of claim 1, having a structure represented by a formula:

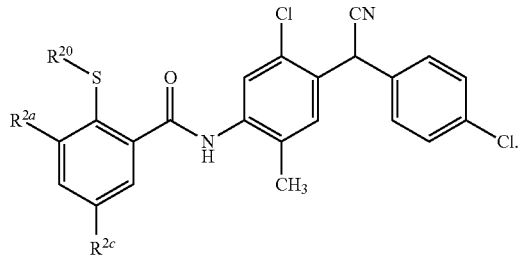

10. The compound of claim 1, having a structure represented by a formula:

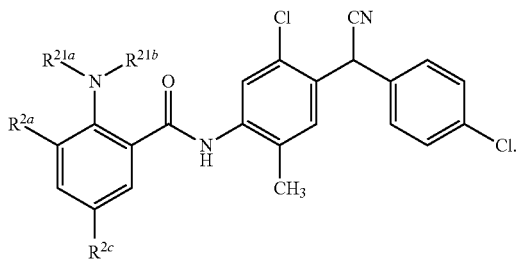

11. The compound of claim 1, selected from:

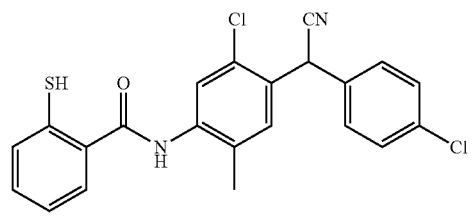

and

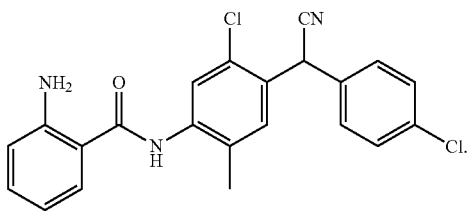

12. A compound selected from:

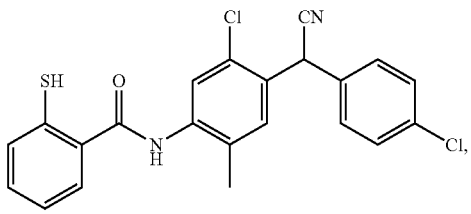

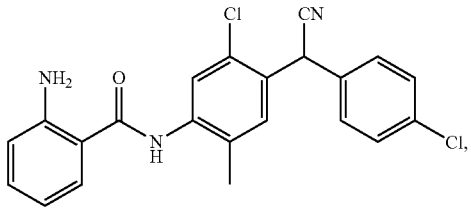

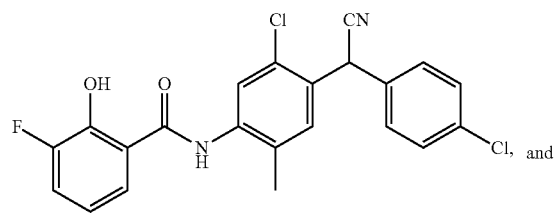

and

-continued

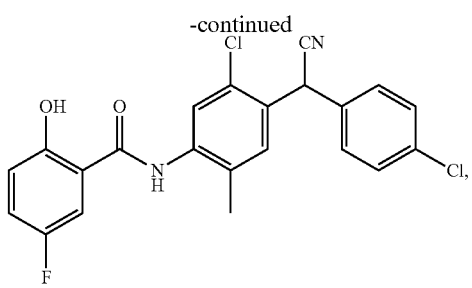

or a pharmaceutically acceptable salt thereof.

13. A pharmaceutical composition comprising a therapeutically effective amount of at least one compound of claim 1 or claim 12 and a pharmaceutically acceptable carrier.

14. A method for treating a hypoxic brain injury in a subject, the method comprising the step of administering to the subject an effective amount of at least one compound having a structure represented by a formula:

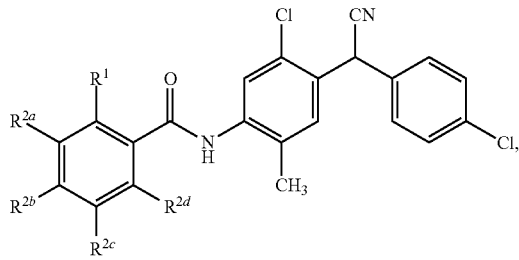

wherein $R^1$ is selected from —OH, —SR$^{20}$, and —NR$^{21a}$R$^{21b}$;

wherein $R^{20}$, when present, is selected from hydrogen and C1-C4 alkyl;

wherein each of $R^{21a}$ and $R^{21b}$, when present, is independently selected from hydrogen and C1-C4 alkyl;

wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino, provided that when $R^1$ is —OH and each of $R^{2b}$ and $R^{2d}$ is hydrogen then neither of $R^{2a}$ and $R^{2c}$ is halogen, or a pharmaceutically acceptable salt thereof.

15. The method of claim 14, wherein the subject has been diagnosed with a need for treatment of a hypoxic brain injury prior to the administering step.

16. The method of claim 14, further comprising the step of identifying a subject in need of treatment of a hypoxic brain injury.

17. The method of claim 14, wherein the hypoxic brain injury is due to traumatic brain injury, ischemic stroke, carbon monoxide poisoning, drowning, choking, suffocating, or cardiac arrest.

18. The method of claim 14, wherein the hypoxic brain injury is due to ischemic stroke.

* * * * *